United States Patent
Blumwald et al.

(10) Patent No.: US 7,041,875 B1
(45) Date of Patent: May 9, 2006

(54) GENETIC ENGINEERING SALT TOLERANCE IN CROP PLANTS

(76) Inventors: Eduardo Blumwald, 434 Roxton Road, Toronto, Ontario (CA), M6G 3R4; Maris Apse, 292 Withrow Ave., Upper Unit, Toronto, Ontario (CA), M4J 1B7; Wayne Snedden, 208 Poplar Plains, Toronto, Ontario (CA), M4V 2N4; Gilad Aharon, 69 Dewlane Drive, Willowdale, Ontario (CA), M2R 2P9

( * ) Notice: Subject to any disclaimer, the term of this patent is extended or adjusted under 35 U.S.C. 154(b) by 0 days.

(21) Appl. No.: 09/271,584

(22) Filed: Mar. 18, 1999

Related U.S. Application Data

(60) Provisional application No. 60/116,111, filed on Jan. 15, 1999, and provisional application No. 60/078,474, filed on Mar. 18, 1998.

(51) Int. Cl.
*A01H 5/00* (2006.01)
*C12N 15/82* (2006.01)
*C12N 15/29* (2006.01)

(52) U.S. Cl. ............... 800/298; 800/278; 536/23.6; 435/418

(58) Field of Classification Search ............ 800/278, 800/298, 320.1, 287, 288, 305, 306, 307, 800/308, 309, 310, 312, 314, 315, 317.1, 800/317.2, 317.3, 317.4, 318, 320, 320.2, 800/320.3, 322, 323.3; 435/419, 320.1, 430, 435/243, 254.1, 254.2, 411, 412, 415, 416, 435/417, 468; 536/23.6, 23.1

See application file for complete search history.

(56) References Cited

U.S. PATENT DOCUMENTS

| | | | | |
|---|---|---|---|---|
| 4,616,100 | A | | 10/1986 | McHughen et al. ............ 800/1 |
| 5,272,085 | A | | 12/1993 | Young et al. ............ 435/254.2 |
| 5,346,815 | A | | 9/1994 | Krulwich et al. ........... 435/69.1 |
| 5,441,875 | A | * | 8/1995 | Hediger ..................... 435/69.1 |
| 5,563,246 | A | | 10/1996 | Krulwich et al. ........... 435/69.1 |
| 5,563,324 | A | | 10/1996 | Tarczynski et al. ......... 800/205 |
| 5,639,950 | A | | 6/1997 | Verma et al. ................ 800/205 |
| 5,689,039 | A | | 11/1997 | Becker et al. ............... 800/205 |
| 5,750,848 | A | * | 5/1998 | Kruger et al. ............... 800/281 |
| 5,780,709 | A | | 7/1998 | Adams et al. ............... 800/205 |
| 5,859,337 | A | | 1/1999 | Gasser et al. ............... 800/205 |
| 2002/0083487 | A1 | | 6/2002 | Fukuda et al. |

FOREIGN PATENT DOCUMENTS

| WO | 9106651 | 5/1991 |
|---|---|---|
| WO | 9639020 | 5/1996 |
| WO | 9713843 | 10/1996 |

OTHER PUBLICATIONS

Brant, S. R. et al., Accession No. T51330, 1997, GenBank.*
Hahnnenberger, K. M. et al., "Functional expression of the *Schizosaccharomyces pombe* Na+/H+ antiporter gene, sod2, in *Saccharomyces cerevisiae*." 1996, Proc. Natl. Acad. Sci. USA, vol. 93, 5031–5036.*
Bork, P. "Powers and Pitfalls in Sequence Analysis: The 70% Hurdle." 2000, Genome Research, vol. 10, pp. 398–400.*
Bowie, J. U. et al., "Deciphering the Message in Protein Sequences: Tolerance to Amino Acid Substitutions." 1990, Science, vol. 247, pp. 1306–1310.*
Broun, P. et al., "Catalytic Plasticity of Fatty Acid Modification Enzymes Underlying Chemical Diversity of Plant Lipids." 1998, Science, vol. 282, pp. 1315–1317.*
Lazar, E. et al., "Transforming Growth Factor a: Mutation of Aspartic Acid 47 and Leucine 48 Results in Different Biological Activities." 1988, Molecular and Cellular Biology, vol. 8, pp. 1247–1252.*
Gordon–Kamm, W. J. et al., "Transformation of Maize Cells and Regeneration of Fertile Transgenic Plants." 1990, The Plant Cell, vol. 2, pp. 603–618.*
Strathmann et al, 1989, Proc. Natl. Acad. Sci. USA 86:7407–7409.*
O–Connor, Altered Tomato Thrives in Salty Soil. New York Times.*
Kaufman, A New Strain of Tomatoes, And Don't Hold the Salt. Washington Post, Jul. 31, 2001, p. A03.*
Gormat, Science News 160, Aug., 4, 2001.*
Zandonella, New Scientist.com, Jul. 2001.*
Zhang et al, 2001, Nature Biotechnol. 19:765–768.*
Jacoby, Chemical engineering News.*
Apse et al, 1999, 285:1256–1258.*
Barkla, B.J., Apse, M.P., Manolson, M.F. et al. The plant vacuolar Na+/H+ antiport, Membrane Transport in Plants and Fungi: MOlecular Mechanisms and Control. Blatt et al., ed. The Company of Biologists LTD Cambridge, UK, 141–153, 1994.
Dante, M., Wamsley, P. and Gibson, A Sequence 457 AA; 50611 MW, Embl database, 1997.

(Continued)

*Primary Examiner*—Anne Kubelik
(74) *Attorney, Agent, or Firm*—Morrison & Foerster LLP

(57) ABSTRACT

The invention is isolated nucleic acid molecules encoding Na+/H+ exchanger polypeptides for extrusion of monovalent cations (preferably lithium ions and postassium ions, most preferably sodium ions) from the cytosol of cells to provide the cell with increased salt tolerance. In a preferred embodiment, the nucleic acid is obtained from *Arabidopsis thaliana*. Crop species transformed with the nucleic acid molecule are capable of surviving in soil with high salt levels that would normally inhibit growth of the crop species.

21 Claims, 35 Drawing Sheets

(4 of 35 Drawing Sheet(s) Filed in Color)

OTHER PUBLICATIONS

Newman, T., deBruijn, F.J., Green, P. et al. Genes galore: a summary of methods for accessing results from large–scale partial sequencing of anonymous *Arabidopsis* cDNA clones, Plant Physiol. 106: 1241–1255, 1994. (Also GenBank Accession No. T75860).

Borgese, F., Sardet, C. and Cappadoro, M. et al. Cloning and expression of a cAMP–activated Na+/H+ exchanger: evidence that the cytoplasmic domain mediates hormonal regulation, Proceedings of the National Academy of Sciences of the United States of America 89: 6765–6769, 1992.

Ohki R., Oishi, M. and Kiyama, R. Preference of recombination sites involved in the formation of extrachromosomal copies of the human alphoid Sau3A repeat family, Nucleic Acids Res., 23: 4986–4991, 1995.

Barkla, B.J., Zingarelli, L., Blumwald, E. et al. Tonoplast Na+/H+ antiport activity and its energization by the vacuolar H+ –ATPase in the halophytic plant *Mesembryanthemum crystallinum* $L^1$, Plant Physiol., 109: 549–556, 1995.

Schachtman, D.P., Kumar, R., Schroeder, J.I. et al. Molecular and functional characterization of a novel low–affinity cation transporter (LCT1) in higher plants, Proceedings of the National Academy of Sciences of the United States of America, 94: 11079–11084, 1997.

Bohnert, H.J. and Jensen, R.G. Strategies for engineering water–stress tolerance in plants, Trends in Biotechnology, 14: 89–97, 1996.

Rausch, T., Kirsch, M., Low, R. et al. Salt stress responses of higher plants: the role of proton pumps and Na+/H+ – antiporters, Journal of Plant Physiology, 148: 425–433, 1996.

Gaxiola, R.A., Rao, R., Sherman, A. et al. The *Arabidopsis thaliana* proton transporters, AtNhx1 and Avp1, can function in cation detoxification in yeast, Proceedings of the National Academy of Sciences of the United States of America, 96: 1480–1485, 1999. (GenBank Accession No. AF106324 (DNA) and 4324597 (protein)).

Apse, M.P., Aharon, G.S., Snedden, W.A. et al. Salt tolerance conferred by overexpression of a vacuolar Na+/H+ antiport in *Arabidopsis*, Science, 285: 1256–1258, 1999.

Murphy, L. and Harris, D. et al., Direct submission *Schizosaccharomyces pombe* chromosome I sequencing project, Unpublished, Nov. 4, 1998, GenBank Accession No. 3850064.

Dietrich, F.S. et al., The sequence of *S. cerevisiae* lambda 3641 and cosmids 9461, 9831, and 9410, GenBank Accession No. 927695, Aug. 27, 1997.

Sasaki, T. et al., Rice cDNA from panicle, GenBank Accession No. C91832, Apr. 20, 1998.

Sasaki, T. et al., Rice cDNA from panicle, GenBank Accession No. C91861, Apr. 20, 1998.

Yamamoto, K. et al., Rice cDNA from green shoot, GenBank Accession No. AU032544, Oct. 20, 1998.

Covitz, P.A. et al., Expressed sequence tags from a root hair–enriched Medicago truncatul cDNA library, GenBank Accession No. AA660573, Nov. 10, 1997.

Kadyrzhanova, D. et al., Sequences for STS primer sets, GenBank Accession No. L44032, Jul. 27, 1995.

Blumwald, Eduardo et al., Cloning of plant sodium/proton antiports in *Arabidopsis*. Eastern Regional Meeting of the Canadian Society of Plant Physiologists, Toronto (Dec. 1998).

Blumwald, Eduardo et al., Cloning and characterization of a plant sodium/proton antiport. Annual Meeting of the American Society of Plant Physiologists, Madison, USA (Jun. 1998).

Blumwald, Eduardo et al., Cloning and characterization of a plant sodium/proton antiports. $11^{th}$ Int'l Workshop on Plant Membrane Biology, Cambridge, UK (Aug. 1998).

Blumwaldm Eduardo et al., Cloning and characterization of a plant sodium/proton antiports. Gordon Conference on Drought and Salinity Stress inj Plants, Oxford, UK (Aug. 1998).

Darley, Catherine P. et al., ANA1 a Na+/H+ antiporter from *Arabidopsis*? $11^{th}$ Int'l Workshop on Plant Membrane Biology, Cambridge, UK (Aug. 1998).

Nass, Richard et al., Intracellular sequestration of sodium by a novel Na+/H+ exchanger in yeast is enhanced by mutations in the plasma membrane H+–ATPase. Biological Chemistry, 272:26145–26152 (1997).

Apse, M., et al. "Identification of Two Putative Sodium/Proton Antiports in *Arabidopsis*" Plant Membrane Biology Workshop Aug. 1998, Cambridge, U.K. (Poster).

Apse, M. et, al. "Cloning and Characterization of Plant Sodium/Proton Antiports" 11 International Workshop on Plant Membrane Biology. Aug. 1998. Cambridge, U.K. (Abstract).

Catherine Darley presented a poster relating to the abstract listed as item "BL" on the applications information disclosure statement (Darley, Catherine P. et al., ANA1 aNa+ antiporter from *Arabidopsis*?.

Ohta, Masaru et al. (2002) "Introduction of a Na+/H+ antiporter gene from *Atriplex gmelini* confers salt tolerance to rice" *FEBS Letters* 26785: 1–4.

\* cited by examiner

Figure 1(a)-1

```
1    CCTCTCTGTTTCGTTCCTCGTAGACGAAGAAGAAGAAGAATCTCA
46   GGTTTTAGCTTTCGAAGCTTCCAAAATTTTGAATTTTGATCTTCT
91   GGGCTCTTTTGTAAATCAGACTGAAGATATTTAGATTACCCAGAA
136  GTTGTTCAAGGAATGGTTTCAGTGGACAGCACGGAAAGATAAAAG
181  AGACTTTTTTTTCCAGATTTTGCTGATCCAAAATCTGAATAGTTG
226  TTCATGTTCTTGGATCAAATCTGGAAGAGGAAGTTTGTTGGATC
271  TAGAAGAAGATAACAATGTTGGATTCTCTAGTGTCGAAACTGCCT
                    M  L  D  S  L  V  S  K  L  P      10
316  TCGTTATCGACATCTGATCACGCTTCTGTGGTTGCGTTGAATCTC
      S  L  S  T  S  D  H  A  S  V  V  A  L  N  L    25
361  TTTGTTGCACTTCTTTGTGCTTGTATTGTTCTTGGTCATCTTTTG
      F  V  A  L  L  C  A  C  I  V  L  G  H  L  L    40
406  GAAGAGAATAGATGGATGAACGAATCCATCACCGCCTTGTTGATT
      E  E  N  R  W  M  N  E  S  I  T  A  L  L  I    55
451  GGGCTAGGCACTGGTGTTACCATTTTGTTGATTAGTAAAGGAAAA
      G  L  G  T  G  V  T  I  L  L  I  S  K  G  K    70
496  AGCTCGCATCTTCTCGTCTTTAGTGAAGATCTTTTCTTCATATAT
      S  S  H  L  L  V  F  S  E  D  L  F  F  I  Y    85
541  CTTTTGCCACCCATTATATTCAATGCAGGGTTTCAAGTAAAAAAG
      L  L  P  P  I  I  F  N  A  G  F  Q  V  K  K    100
586  AAGCAGTTTTTCCGCAATTTCGTGACTATTATGCTTTTTGGTGCT
      K  Q  F  F  R  N  F  V  T  I  M  L  F  G  A    115
631  GTTGGGACTATTATTTCTTGCACAATCATATCTCTAGGTGTAACA
      V  G  T  I  I  S  C  T  I  I  S  L  G  V  T    130
676  CAGTTCTTTAAGAAGTTGGACATTGGAACCTTTGACTTGGGTGAT
      Q  F  F  K  K  L  D  I  G  T  F  D  L  G  D    145
721  TATCTTGCTATTGGTGCCATATTTGCTGCAACAGATTCAGTATGT
      Y  L  A  I  G  A  I  F  A  A  T  D  S  V  C    160
766  ACACTGCAGGTTCTGAATCAAGACGAGACACCTTTGCTTTACAGT
      T  L  Q  V  L  N  Q  D  E  T  P  L  L  Y  S    175
811  CTTGTATTCGGAGAGGGTGTTGTGAATGATGCAACGTCAGTTGTG
      L  V  F  G  E  G  V  V  N  D  A  T  S  V  V    190
856  GTCTTCAACGCGATTCAGAGCTTTGATCTCACTCACCTAAACCAC
      V  F  N  A  I  Q  S  F  D  L  T  H  L  N  H    205
901  GAAGCTGCTTTTCATCTTCTTGGAAACTTCTTGTATTTGTTTCTC
      E  A  A  F  H  L  L  G  N  F  L  Y  L  F  L    220
946  CTAAGTACCTTGCTTGGTGCTGCAACCGGTCTGATAAGTGCGTAT
```

Figure 1(a)-2

```
            L  S  T  L  L  G  A  A  T  G  L  I  S  A  Y     235
 991    GTTATCAAGAAGCTATACTTTGGAAGGCACTCAACTGACCGAGAG
            V  I  K  K  L  Y  F  G  R  H  S  T  D  R  E     250
1036    GTTGCCCTTATGATGCTTATGGCGTATCTTTCTTATATGCTTGCT
            V  A  L  M  M  L  M  A  Y  L  S  Y  M  L  A     265
1081    GAGCTTTTCGACTTGAGCGGTATCCTCACTGTGTTTTTCTGTGGT
            E  L  F  D  L  S  G  I  L  T  V  F  F  C  G     280
1126    ATTGTGATGTCCCATTACACATGGCACAATGTAACGGAGAGCTCA
            I  V  M  S  H  Y  T  W  H  N  V  T  E  S  S     295
1171    AGAATAACAACAAAGCATACCTTTGCAACTTTGTCATTTCTTGCG
            R  I  T  T  K  H  T  F  A  T  L  S  F  L  A     310
1216    GAGACATTTATTTTCTTGTATGTTGGAATGGATGCCTTGGACATT
            E  T  F  I  F  L  Y  V  G  M  D  A  L  D  I     325
1261    GACAAGTGGAGATCCGTGAGTGACACACCGGGAACATCGATCGCA
            D  K  W  R  S  V  S  D  T  P  G  T  S  I  A     340
1306    GTGAGCTCAATCCTAATGGGTCTGGTCATGGTTGGAAGAGCAGCG
            V  S  S  I  L  M  G  L  V  M  V  G  R  A  A     355
1351    TTCGTCTTTCCGTTATCGTTTCTATCTAACTTAGCCAAGAAGAAT
            F  V  F  P  L  S  F  L  S  N  L  A  K  K  N     370
1396    CAAAGCGAGAAAATCAACTTTAACATGCAGGTTGTGATTTGGTGG
            Q  S  E  K  I  N  F  N  M  Q  V  V  I  W  W     385
1441    TCTGGTCTCATGAGAGGTGCTGTATCTATGGCTCTTGCATACAAC
            S  G  L  M  R  G  A  V  S  M  A  L  A  Y  N     400
1486    AAGTTTACAAGGGCCGGGCACACAGATGTACGCGGGAATGCAATC
            K  F  T  R  A  G  H  T  D  V  R  G  N  A  I     415
1531    ATGATCACGAGTACGATAACTGTCTGTCTTTTTAGCACAGTGGTG
            M  I  T  S  T  I  T  V  C  L  F  S  T  V  V     430
1576    TTTGGTATGCTGACCAAACCACTCATAAGCTACCTATTACCGCAC
            F  G  M  L  T  K  P  L  I  S  Y  L  L  P  H     445
1621    CAGAACGCCACCACGAGCATGTTATCTGATGACAACACCCCAAAA
            Q  N  A  T  T  S  M  L  S  D  D  N  T  P  K     460
1666    TCCATACATATCCCTTTGTTGGACCAAGACTCGTTCATTGAGCCT
            S  I  H  I  P  L  L  D  Q  D  S  F  I  E  P     475
1711    TCAGGGAACCACAATGTGCCTCGGCCTGACAGTATACGTGGCTTC
            S  G  N  H  N  V  P  R  P  D  S  I  R  G  F     490
1756    TTGACACGGCCCACTCGAACCGTGCATTACTACTGGAGACAATTT
            L  T  R  P  T  R  T  V  H  Y  Y  W  R  Q  F     505
```

Figure 1(a)-3

```
1801   GATGACTCCTTCATGCGACCCGTCTTTGGAGGTCGTGGCTTTGTA
        D   D   S   F   M   R   P   V   F   G   G   R   G   F   V     520
1846   CCCTTTGTTCCAGGTTCTCCAACTGAGAGAAACCCTCCTGATCTT
        P   F   V   P   G   S   P   T   E   R   N   P   P   D   L     535
1891   AGTAAGGCTTGAGGGTAACGTGGAAGAAAAGCTTTGATTTTTTT
        S   K   A                                                     538
1936   GGTAGAAAAGGGTGATTCAAATTATGCTTTTGTGTAAATTATCCA
1981   TTTGTAATATTGTTTGTGAGGACAGAAATCTGTCCTAACGTTTTG
2026   AGAGCAGAAAGCAAAACATGGCAACTTTGAAGTGTTTGATTGATG
2071   TATGTAATTATATTCATATTTGTTTTGTTGTAACACAAACTACAC
2116   ATTTGTTTATGTTTTGAATTTGGTTTTTGCTTCGAAAAAAAAAAA
2161   AAAAAAAAAAAAAAAAAA
```

Figure 1(b)-1

```
1    TCTTCGTTTGCGATTGGTGTTTTCAAAATCGACGAAATCGAAAAC
46   ATTATCGAGTGAAAAATGAGTATCGGATTAACAGAGTTTGTGACG
                     M  S  I  G  L  T  E  F  V  T    10
91   AATAAACTAGCAGCTGAGCATCCTCAGGTGATACCAATCTCAGTG
      N  K  L  A  A  E  H  P  Q  V  I  P  I  S  V    25
     TTCATCGCCATTCTCTGTCTATGTTTAGTTATCGGCCACTTGCTT
46    F  I  A  I  L  C  L  V  I  G  H  L  L          40
181  GAAGAGAATCGATGGGTTAATGAATCTATTACCGCCATTTTAGTA
      E  E  N  R  W  V  N  E  S  I  T  A  I  L  V    55
226  GGAGCAGCATCAGGAACAGTGATCTTACTTATTAGTAAAGGAAAA
      G  A  A  S  G  T  V  I  L  L  I  S  K  G  K    70
271  AGTTCACATATTTTGGTGTTTGATGAAGAACTCTTCTTCATTTAC
      S  S  H  I  L  V  F  D  E  E  L  F  F  I  Y    85
316  CTTCTTCCTCCAATAATCTTCAATGCTGGGTTCCAAGTTAAGAAA
      L  L  P  P  I  I  F  N  A  G  F  Q  V  K  K   100
361  AAGAAGTTTTTTCACAACTTTTTAACCATCATGTCCTTTGGTGTG
      K  K  F  F  H  N  F  L  T  I  M  S  F  G  V   115
406  ATTGGAGTTTTCATCTCCACTGTCATTATCTCGTTTGGGACTTGG
      I  G  V  F  I  S  T  V  I  I  S  F  G  T  W   130
451  TGGCTGTTTCCCAAGTTGGGATTTAAGGGGTTGAGTGCTAGAGAC
      W  L  F  P  K  L  G  F  K  G  L  S  A  R  D   145
496  TATCTTGCCATAGGAACGATTTTCTCATCAACTGATACTGTTTGC
      Y  L  A  I  G  T  I  F  S  S  T  D  T  V  C   160
541  ACTCTACAGATTCTCCATCAAGATGAAACACCATTGCTATACAGC
      T  L  Q  I  L  H  Q  D  E  T  P  L  L  Y  S   185
586  TTAGTCTTTGGAGAAGGAGTGGTGAATGATGCAACCTCAGTTGTA
      L  V  F  G  E  G  V  V  N  D  A  T  S  V  V   195
631  CTGTTCAACGCCGTGCAAAAGATTCAATTTGAAAGCCTAACCGGT
      L  F  N  A  V  Q  K  I  Q  F  E  S  L  T  G   205
676  TGGACGGCGCTGCAAGTATTTGGGAACTTTTTGTACCTCTTCTCA
      W  T  A  L  Q  V  F  G  N  F  L  Y  L  F  S   220
721  ACAAGCACACTTCTCGGAATTGGTGTGGGGCTAATAACATCTTTT
      T  S  T  L  L  G  I  G  V  G  L  I  T  S  F   235
766  GTTCTTAAAACCTTGTATTTTGGAAGACATTCTACTACACGCGAA
      V  L  K  T  L  Y  F  G  R  H  S  T  T  R  E   250
811  CTCGCCATCATGGTTCTAATGGCTTACCTTTCATATATGTTGGCT
      L  A  I  M  V  L  M  A  Y  L  S  Y  M  L  A   265
```

Figure 1(b)-2

```
856   GAGCTCTTCTCATTAAGTGGAATTCTTACTGTTTTCTTCTGTGGT
      E   L   F   S   L   S   G   I   L   T   V   F   F   C   G    280
901   GTTTTAATGTCGCATTATGCATCATATAACGTGACAGAGAGCTCA
      V   L   M   S   H   Y   A   S   Y   N   V   T   E   S   S    295
946   AGAATCACTTCCAGGCATGTATTTGCAATGTTGTCCTTTATTGCG
      R   I   T   S   R   H   V   F   A   M   L   S   F   I   A    310
991   GAGACATTCATATTTCTGTATGTTGGAACAGATGCTCTTGATTTT
      E   T   F   I   F   L   Y   V   G   T   D   A   L   D   F    325
1036  ACAAAGTGGAAGACAAGCAGCTTAAGCTTTGGGGGTACTCTGGGT
      T   K   W   K   T   S   S   L   S   F   G   G   T   L   G    340
1081  GTCTCCGGTGTCATAACCGCATTAGTATTGCTTGGACGAGCAGCA
      V   S   G   V   I   T   A   L   V   L   L   G   R   A   A    355
1126  TTTGTCTTTCCACTCTCGGTCTTAACAAATTTCATGAACAGGCAC
      F   V   F   P   L   S   V   L   T   N   F   M   N   R   H    370
1171  ACTGAAAGAAACGAGTCTATCACATTTAAGCATCAGGTGATCATT
      T   E   R   N   E   S   I   T   F   K   H   Q   V   I   I    385
1216  TGGTGGGCAGGTCTAATGCGAGGTGCTGTCTCAATTGCTCTGGCT
      W   W   A   G   L   M   R   G   A   V   S   I   A   L   A    400
1261  TTCAAGCAGTTCACATACTCCGGTGTTACATTGGATCCTGTGAAT
      F   K   Q   F   T   Y   S   G   V   T   L   D   P   V   N    415
1306  GCTGCCATGGTCACCAACACCACTATCGTTGTTCTCTTTACTACA
      A   A   M   V   T   N   T   T   I   V   V   L   F   T   T    430
1351  CTGGTCTTTGGTTTCCTCACAAAACCACTTGTGAATTATCTCCTT
      L   V   F   G   F   L   T   K   P   L   V   N   Y   L   L    445
1396  CCTCAAGATGCAAGTCACAACACCGGAAATAGAGGTAAACGCACT
      P   Q   D   A   S   H   N   T   G   N   R   G   K   R   T    460
1441  GAGCCAGGTTCTCCGAAAGAAGATGCGACACTTCCTCTTCTTTCC
      E   P   G   S   P   K   E   D   A   T   L   P   L   L   S    475
1486  TTTGACGAGTCTGCTTCCACCAACTTCAATAGAGCTAGAGATAGT
      F   D   E   S   A   S   T   N   F   N   R   A   R   D   S    490
1531  ATTTCCCTTCTGATGGAACAACCTGTGTACACCATCCACCGCTAC
      I   S   L   L   M   E   Q   P   V   Y   T   I   H   R   Y    505
1576  TGGAGAAAGTTTGACGACACATACATGAGGCCTATCTTCGGTGGA
      W   R   K   F   D   D   T   Y   M   R   P   I   F   G   G    520
1621  CCTCGTCGAGAAAACCAACCAGAATGCTAGAATTGATCCGGGTTC
      P   R   R   E   N   Q   P   E   C                            529
1666  TCCGCGGGGAAATCATGATGAGTTAGTTTTTTTTATAGTCAAGAA
```

Figure 1(b)-3

1711 AGTAGGATAGTTGGTTTAGCTAAAACAGTTTCTTAAAGTTTTTGT
1756 TAAATGTATACAACAAGGTTCTTCTATATACGC

```
1    ACAAAAGCTGGAGCTCCACCGCGGTGGCGGCCGCTCTAGAACTAG
46   TGGATCCCCCGGGCTGCAGGAATTCGCGGCCGCCTCGGCCATGTC
                  R  A  A  G  I  R  G  R  L  G  H  V      12
91   CTCCGCCGTCATCGATTCCACTATCTTCCTGAAGCCAGCGGTTCG
      L  R  R  H  R  F  H  Y  L  P  E  A  S  G  S       27
136  CTTCTCATTGGTTTAATCGTCGGTATACTTGCTAATATCTCCGAC
      L  L  I  G  L  I  V  G  I  L  A  N  I  S  D       42
181  ACTGAGACTAGCATTAGGACGTGGTTTAATTTCCACGAAGAGTTC
      T  E  T  S  I  R  T  W  F  N  F  H  E  E  F       57
226  TTCTTCTTGTTTTTGTTGCCTCCCATCATATTCCAGTCAGGTTTC
      F  F  L  F  L  L  P  P  I  I  F  Q  S  G  F       72
271  AGTCTTCAACCTAAACCATTCTTTTCTAACTTTGGAGCCATTGTT
      S  L  Q  P  K  P  F  F  S  N  F  G  A  I  V       87
316  ACCTTTGCTATCATCGGAACTTTTGTCGCTTCAGTTGTTACTGGT
      T  F  A  I  I  G  T  F  V  A  S  V  V  T  G      102
361  GGTCTGGTTTATCTTGGCGGCTCTATGTATCTCATGTATAAACTT
      G  L  V  Y  L  G  G  S  M  Y  L  M  Y  K  L      117
406  CCCTTTGTTGAGTGTCTTATGTTTGGTGCACTTATATCAGCTACG
      P  F  V  E  C  L  M  F  G  A  L  I  S  A  T      132
451  GACCCTGTCACTGTACTCTCTATATTCCAGGATGTGGGCACCGAT
      D  P  V  T  V  L  S  I  F  Q  D  V  G  T  D      147
496  GTTAACCTGTATGCTTTGGTCTTTGGAGAATCAGTTCTGAATGAT
      V  N  L  Y  A  L  V  F  G  E  S  V  L  N  D      162
541  GCTATGGCAATATCATTGTACAGAACAATGTCCTTAGTAAACCGC
      A  M  A  I  S  L  Y  R  T  M  S  L  V  N  R      177
586  CAGTCCTCGTCTGGGGAACATTTTTCATGGTGGTGATCAGGTTTT
      Q  S  S  S  G  E  H  F  S                        186
631  TTGAGACTTTGCTGGCTCAATGTCGCAGGGGTTGGGGTTGGATTC
676  ACTTCAGCTTAATATCCTCCTCGATCCTCCTATTTCCTA
```

```
1    GGACTTCGAGGGCCATGGCATTTGCACTTGCACTTCAATACTTCA
46   TGATCTACCAGAGGTCACGGCCCAATCATCTTTTACTGCACCACA
          T  R  G  H  G  P  I  I  F  Y  C  T  T      13
91   ACTATTGTTGTTGTCACGGTTTTACTAATAGGAGGTTCGACAGGT
     T  I  V  V  V  T  V  L  L  I  G  G  S  T  G    28
136  AAAATGTTGGAAGCTTTGGAAGTTGTAGGTGACGATCTTGATGAC
     K  M  L  E  A  L  E  V  V  G  D  D  L  D  D    43
181  TCCATGTCTGAAGGCTTTGAAGAGAGCGATCATCAGTATGTCCCT
     S  M  S  E  G  F  E  E  S  D  H  Q  Y  V  P    58
226  CCTCCTTTTAGCATTGGAGCTTCATCTGACGAGGATACATCATCA
     P  P  F  S  I  G  A  S  S  D  E  D  T  S  S    73
271  TCAGGAAGCAGGTTCAAGATGAAGCTGAAGGAGTTTCACAAAACC
     S  G  S  R  F  K  M  K  L  K  E  F  H  K  T    88
316  ACTACATCATTCACCGCGTTGGACAAAAACTTTCTGACTCCGTTC
     T  T  S  F  T  A  L  D  K  N  F  L  T  P  F   103
361  TTCACAACTAATAGTGGAGGTGGAGATGGAGATGGGGAGTAGCAT
     F  T  T  N  S  G  G  G  D  G  D                114
406  GGAAAAGATGTGGAT
```

Figure 1(d)-1

```
1    CGCCACGACCCTCAGGGCCAGGTTAAGCAGCAGCAAGCGGCCGGC
46   GTTGGTATACTGCTTCAGATTATGATGCTCGTGCTTTCCTTCGTT
                             M  M  L  V  L  S  F  V      8
91   CTCGGCCATGTCCTCCGCCGTCATCGATTCCACTATCTTCCTGAA
     L  G  H  V  L  R  R  H  R  F  H  Y  L  P  E    23
136  GCCAGCGGTTCGCTTCTCATTGGTTTAATCGTCGGTATACTTGCT
     A  S  G  S  L  L  I  G  L  I  V  G  I  L  A    38
181  AATATCTCCGATACTGAGACTAGCATTAGGACGTGGTTTAATTTC
     N  I  S  D  T  E  T  S  I  R  T  W  F  N  F    53
226  CACGAAGAGTTCTTCTTCTTGTTTTTGTTGCCTCCCATCATATTC
     H  E  E  F  F  F  L  F  L  L  P  P  I  I  F    68
271  CAGTCAGGTTTCAGTCTTCAACCTAAACCATTCTTTTCTAACTTT
     Q  S  G  F  S  L  Q  P  K  P  F  F  S  N  F    83
316  GGAGCCATTGTTACCTTTGCTATCATCGGAACTTTTGTCGCTTCA
     G  A  I  V  T  F  A  I  I  G  T  F  V  A  S    98
361  GTTGTTACTGGTGGTCTGGTTTATCTTGGCGGCTCTATGTATCTC
     V  V  T  G  G  L  V  Y  L  G  G  S  M  Y  L   113
406  ATGTATAAACTTCCCTTTGTTGAGTGTCTTATGTTTGGTGCACTT
     M  Y  K  L  P  F  V  E  C  L  M  F  G  A  L   128
451  ATATCAGCTACGGACCCTGTCACTGTACTCTCTATATTCCAGGAT
     I  S  A  T  D  P  V  T  V  L  S  I  F  Q  D   143
496  GTGGGCACCGATGTTAACCTGTATGCTTTGGTCTTTGGAGAATCA
     V  G  T  D  V  N  L  Y  A  L  V  F  G  E  S   158
541  GTTCTGAATGATGCTATGGCAATATCATTGTACAGAACAATGTCC
     V  L  N  D  A  M  A  I  S  L  Y  R  T  M  S   173
586  TTAGTAAACCGCCAGTCCTCGTCTGGGGAACATTTTTTCATGGTG
     L  V  N  R  Q  S  S  S  G  E  H  F  F  M  V   188
631  GTGATCAGGTTTTTTGAGACTTTTGCTGGCTCAATGTCTGCAGGG
     V  I  R  F  F  E  T  F  A  G  S  M  S  A  G   203
676  GTTGGGGTTGGATTCACTTCAGCTTTACTCTTTAAGTATGCAGGA
     V  G  V  G  F  T  S  A  L  L  F  K  Y  A  G   218
721  TTGGACACCGAGAATCTTCAGAACTTGGAGTGTTGTCTCTTTGTA
     L  D  T  E  N  L  Q  N  L  E  C  C  L  F  V   233
766  CTTTTCCCGTATTTTTCATACATGCTTGCAGAAGGTGTTGGTCTC
     L  F  P  Y  F  S  Y  M  L  A  E  G  V  G  L   248
811  TCCGGCATTGTTTCTATACTCTTCACAGGAATTGTTATGAAGCGC
     S  G  I  V  S  I  L  F  T  G  I  V  M  K  R   263
```

Figure 1(d)-2

```
 856 TACACTTTCTCAAATCTCTCAGAAGCTTCACAGAGTTTCGTATCT
      Y  T  F  S  N  L  S  E  A  S  Q  S  F  V  S  278
 901 TCTTTTTTTCACTTGATATCTTCGCTAGCAGAAACTTTCACGTTC
      S  F  F  H  L  I  S  S  L  A  E  T  F  T  F  293
 946 ATTTACATGGATTTGATATTGCCATGGAGCAGCATAGCTGGTCC
      I  Y  M  G  F  D  I  A  M  E  Q  H  S  W  S  308
 991 CATGTTGGGTTTATCCTTTTCTCTATTGTATCCTCATTTACTGAT
      H  V  G  F  I  L  F  S  I  V  S  S  F  T  D  323
1036 CGTCAGTGATTGTATGCAGTGGCTGTCAATGTATTTGGTGTGCA
      R  Q                                           325
1081 TATTTGGTCAACCTATTTAGACAGGAGAACCAGAAGATACCTATG
1126 AAGCACCAAAAAGCCCTTTGGTATAGTGGACTTCGAGGGGCAATG
1171 GCATTTGCACTTGCACTTCAATCACTTCATGATCTACCAGAGGGT
1216 CACGGCCAAATCATCTTTACTGCAAACCACAACTATTGTTGTTGT
1261 CACGGTTTTACTAATAGGAGGTTCGACAGGTAAAATGTTGGAAGC
1306 TTTGGAAGTTGTAGGTGACGATCTTGATGACTCCATGTCTGAAGG
1351 CTTTGAAGAGAGCGATCATCAGTATGTCCCTCCTCCTTTTAGCAT
1396 TGGAGCTTCATCTGACGAGGATACATCATCATCAGGAAGCAGGTT
1441 CAAGATGAAGCTGAAGGAGTTTCACAAAACCACTACATCATTCAC
1486 CGCGTTGGACAAAAACTTTCTGACTCCGTTCTTCACAACTAATAG
1531 TGGAGATGGAGATGGAGATGGGGAGTAGCATGGAAAGATGTGTA
1576 TTTGTGGTCCAGGCCAAGCTATAATTAGAGTACACATATGTCTAT
1621 GTAAGATTAACACTGGTTGATTTTACCTCTCGCAAAATGCCCACT
1666 ATAAAGTTGACGATTTCC
```

Figure 1(e)-1

```
1    CAGGGCCAGGTTAAGCAGCAGCAAGCGGCCGGCGTTGGTATACTG
46   CTTCAGATTATGATGCTCGTGCTTTCCTTCGTTCTCGGCCATGTC
              M  M  L  V  L  S  F  V  L  G  H  V    12
91   CTCCGCCGTCATCGATTCCACTATCTTCCTGAAGCCAGCGGTCG
        L  R  R  H  R  F  H  Y  L  P  E  A  S  G  S  27
136  CTTCTCATTGGTTTAATCGTCGGTATACTTGCTAATATCTCCGAT
        L  L  I  G  L  I  V  G  I  L  A  N  I  S  D  42
181  ACTGAGACTAGCATTAGGACGTGGTTTAATTTCCACGAAGAGTTC
        T  E  T  S  I  R  T  W  F  N  F  H  E  E  F  75
226  TTCTTCTTGTTTTGTTGCCTCCCATCATATTCCAGTCAGGTTTC
        F  F  L  F  L  L  P  P  I  I  F  Q  S  G  F  90
271  AGTCTTCAACCTAAACCATTCTTTTCTAACTTTGGAGCCATTGTT
        S  L  Q  P  K  P  F  F  S  N  F  G  A  I  V  105
316  ACCTTTGCTATCATCGGAACTTTTGTCGCTTCAGTTGTTACTGGT
        T  F  A  I  I  G  T  F  V  A  S  V  V  T  G  120
361  GGTCTGGTTTATCTTGGCGGCTCTATGTATCTCATGTATAAACTT
        G  L  V  Y  L  G  G  S  M  Y  L  M  Y  K  L  135
406  CCCTTTGTTGAGTGTCTTATGTTTGGTGCACTTATATCAGCTACG
        P  F  V  E  C  L  M  F  G  A  L  I  S  A  T  150
451  GACCCTGTCACTGTACTCTCTATATTCCAGGATGTGGGCACCGAT
        D  P  V  T  V  L  S  I  F  Q  D  V  G  T  D  165
496  GTTAACCTGTATGCTTTGGTCTTTGGAGAATCAGTTCTGAATGAT
        V  N  L  Y  A  L  V  F  G  E  S  V  L  N  D  180
541  GCTATGGCAATATCATTGTACAGAACAATGTCCTTAGTAAACCGC
        A  M  A  I  S  L  Y  R  T  M  S  L  V  N  R  195
586  CAGTCCTCGTCTGGGGAACATTTTTTCATGGTGGTGATCAGGTTT
        Q  S  S  S  G  E  H  F  F  M  V  V  I  R  F  210
631  TTTGAGACTTTTGCTGGCTCAATGTCTGCAGGGGTTGGGGTTGGA
        F  E  T  F  A  G  S  M  S  A  G  V  G  V  G  225
676  TTCACTTCAGCTTTAATATCCTTCCTCGAATCCTCTATTTTTCTT
        F  T  S  A  L  I  S  F  L  E  S  S  I  F  L  240
721  ATTAGATGTCACATGGCCAAAAATGTATTGTAAAATCTTAACTCA
        I  R  C  H  M  A  K  N  V  L             255
766  GAACACCTCTTTAAGTATGCAGGATTGGACACCGAGAATCTTCAG
811  AACTTGGAGTGTTGTCTCTTTGTACTTTTCCCGTATTTTTCGTAA
856  GTAGACAAAACAACTCTCCTCCTGTCTCTTCGTATTTATGACAAC
901  ACTTCTTCCCCTAATGTATTCTGGTTATTCTGTAAGATACATGC
```

Figure 1(e)-2

```
946   TTGCAGAAGGTGTTGGTCTCTCCGGCATTGTTTCTATACTCTTCA
991   CAGGAATTGTAATCGCCGAGTCATTGTAGCTTTTACATCTTAGTT
1036  GATGTTAATATCTTGGAAAGACATATTTAGGCTGCCTAATATAGT
1081  GCTACTGTAGGTTATGAAGCGCTACACTTTCTCAAATCTCTCAGA
1126  AGCTTCACAGAGTTTCGTATCTTCTTTTTTTCACTTGATATCTTC
1171  GCTAGCAGAAACTTTCACGTTCATTTACATGGGATTTGATATTGC
1216  CATGGAGCAGCATAGCTGGTCCCATGTTGGGTTTATCCTTTTCTC
1261  TATTGTATCCTCATTTACTGATCGTCAGTGATTGTATGCAGTGTT
1306  AGTCAGTGTTGTAAATCCTTGACTTTACCTTTTGCTTCTGCGTTT
1351  CATGACTGACATCAGTTGTTTATTGGCGTGGCTAGGTGACTAAAT
1396  GCTTTTTATCCTGGCTGATCGCTTCATTATCACCATGGTTTTCG
1441  ATTCGGATTTACCTATATGTTCTGCAATGCTTTTCTCACGCAGGG
1486  CTGTCAATGTATTTGGGTGTGCATATTTGGTCAACCTATTTAGAC
1531  AGGAGAACCAGAAGATACCTATGAAGCACCAAAAAGCCCTTTGGT
1576  ATAGTGGACTTCGAGGGCAATGGCATTTGCACTTGCACTTCAAT
1621  CACTTCATGATCTACCAGAGGGTCACGGCCAAATCATCTTTACTG
1666  CAACCACAACTATTGTTGTTGTCACGGTTTTACTAATAGGAGGTT
1711  CGACAGGTAAAATGTTGGAAGCTTTGGAAGTTGTAGGTGACGATC
1756  TTGATGACTCCATGTCTGAAGGCTTTGAAGAGAGCGATCATCAGT
1801  ATGTCCTCCTCCTTTTAGCATTGGAGCTTCATCTGACGAGGATA
1846  CATCATCATCAGGAAGCAGGTTCAAGATGAAGCTGAAGGAGTTTC
1891  ACAAAACCACTACATCATTCACCGCGTTGGACAAAAACTTTCTGA
1936  CTCCGTTCTTCACAACTAATAGTGGAGATGGAGATGGAGATGGGG
1981  AGTAGCATGGAAAGATGTGTATTTGTGGTCCAGGCCAAGCTATA
2026  ATTAGAGTACACATATGTCTATGTAAGATTAACACTGGTTGATTT
2071  TACCTCTCGCAAAATGCCCACTATAAAGTTGACGATTTCCAAGAC
2116  ATTTCGA
```

Figure 2(a)-1

| | | | | | |
|---|---|---|---|---|---|
| AtNHX1 | - - - - - - - - - | - - - - - - - - | - - - - - - - - | - - - - - - M L D S L | V S K L P S L S T S | 15 |
| ScNHX | M L S K V L L N I A | F K V L L T T - - - | - - - - - M L D S L | D E L L P S P D L P | 37 |
| HsNHE6 | M A R R G W R R A P | L R R G V G S S P R | A K R A V D P D D D | L L A V G V F D W A | 40 |
| CeNHE1 | - - - - - - - - - - | - - - - - - - - - - | A R R L M R P L W L | F F M S Q T F D V I | 16 |
| | | | | | |
| AtNHX1 | D H A - - - - - - - | - - - S V M A L N | - - - - - - - - - - | - - - L F V A L | 29 |
| ScNHX | G S D D P I A G - - | - - - D P D V D L N | - - - - P V T E E M F S - - | S W A L F I M L L | 70 |
| HsNHE6 | G A S D G G G G E A | R A M D E E I V S E | K Q A E E S H R Q D | S A N L L I F I L L | 80 |
| CeNHE1 | T K N - - - - - - - | - - - K T I V K E | P P D - - - - - - - | - - - - - Y L M | 31 |
| | | | | | |
| AtNHX1 | L C A C I V L G H L | L E E N R - - - W M | N E S I T A L L I G | L G T G V T I L L I | 66 |
| ScNHX | L I S A L W S S Y Y | L T Q K R I R A V H | E T I V L S I F Y G M | V I G L I I R M S P | 110 |
| HsNHE6 | L T L T J T I W L | F K H R R A R F L H | E T G L A M I V G L | L V G L V L R Y G I | 120 |
| CeNHE1 | L E V K P E - - - - | - - - - - - - - - G | G S R V S F H Y E L | L E G F F A D K R K | 58 |
| | | | | | |
| AtNHX1 | S - K G K S S - - - | - - - - - - - - - - | - - H L L V F S E D | L F F I Y L L P P I | 90 |
| ScNHX | G H Y I Q D T V - - | - - - - - - - - - - | - - - - - T F N S S | Y F F N V L L P P I | 133 |
| HsNHE6 | - H V P S D V N N V | T L S C E V Q S S P | T T L L V T F D P E | V F F N I L L P P I | 159 |
| CeNHE1 | - K I E Q Q I E Q K | S - - - - - - - - - | - - - - - V F S P E | V F F N M L I P P I | 83 |
| | | | | | |
| AtNHX1 | I F N A G F Q V K K | K Q F F R N F V T I | M L F G A V G T I I | S C T I I S L G V T | 130 |
| ScNHX | I L N S G Y E L N Q | V N F F N M L S I | L I F A I P G T F | S A V V I G I I L Y | 173 |
| HsNHE6 | I F Y A G Y S L K R | R H F F R N L G S I | L A Y A F L G T A I | S C F V I G S I M Y | 199 |
| CeNHE1 | I F N A G Y S L K R | R H F F R N I G S I | L A I V F J G T T I | S C F G T G C L M F | 123 |
| | | | | | |
| AtNHX1 | Q F F K K L D I G - | - - T F D L G D | Y L A I G A I F A A | T D S V C T L Q V L | 165 |
| ScNHX | I W T F L G L E S - | - - - I D I S F A D | A M S V G A T L S A | T D P V T I L S I F | 209 |
| HsNHE6 | G C V T L M K V T G | Q L A G D F Y T D | C L F G A I V S A | T D P V T V L A I F | 239 |
| CeNHE1 | V F T S I F Q M G - | - - - - - Y S F K E | L L F F G A L I S A | T D P V T I I S V F | 157 |
| | | | | | |
| AtNHX1 | N Q D E T P - L L Y | S L V F G E G V N | D A I S V V F N A | I Q S F D L T - - - | 201 |
| ScNHX | N A Y K V D P K L Y | T I I F G E S L L N | D A I S I V M F E T | C Q K F H G Q - - - | 246 |
| HsNHE6 | H E L Q V D V E L Y | A L L F G E S V L N | D A V A I V L S S S | I V A Y Q P A G D N | 279 |
| CeNHE1 | N D M N V E A D L F | A L I F G E S A L N | D A V A I V L S E V | I E N F S T S - - - | 194 |

| | | | | | |
|---|---|---|---|---|---|
| AtNHX1 | LFSTVVFGML | TKPLISYLLP | HQNATTSMLS | D----DNTPKS | 461 |
| ScNHX1 | VLTVIIFGGT | TAGMLEVLNI | KTGCISEEDT | S----DDEFD | 504 |
| HsNHE6 | FFTWVFGGT | TAMLSCLHI | RVGVDSDQEH | LGVPENERRT | 526 |
| CeNHE1 | IVTVLVNGGL | TSWMIDYLQI | KHGKDAIEEG | Q-RLENSMSS | 440 |
| | | | | | |
| AtNHX1 | IHIP----- | -------- | DSFIEPSG- | -------- | 477 |
| ScNHX1 | IEAP----- | -RAINLLNG | SSIQTDLG- | -------- | 525 |
| HsNHE6 | TKAESAWLFR | MWYNFDHNYL | KPLLTHSGPP | ----P---- | 566 |
| CeNHE1 | SPAD----- | --QHSDLDES | VPVTMSPG- | LTTTLPACCG | 462 |
| | | | | | |
| AtNHX1 | -NHNVPRPDS | IRGFLTRPTR | TVHYYWRQFD | DSFMRPVFGG | 516 |
| ScNHX1 | YSDNNSPDIS | IDQFAVSSNK | NLPNNISTTG | GNTFGGLNET | 565 |
| HsNHE6 | PIARCLTSPQ | AYENQEQLKD | DDSDLILNDG | DISLTYGDST | 606 |
| CeNHE1 | PWDKAFLPRK | WYHFDARWQL | LK--LVFQFH | ETSTDPCDAI | 500 |
| | | | | | |
| AtNHX1 | RGFVPFVPGS | PTERNPPDLS | KA------ | WFQNFDEQVL | 538 |
| ScNHX1 | ENTSPNPARS | SMDKRNLRDK | LGTIFNSDSQ | DHELVIRGTR | 605 |
| HsNHE6 | VNTEPATSSA | PRRFMGNSSE | DALDRELAFG | QYNCTIRDSI | 646 |
| CeNHE1 | FGTNTPTVLS | SIDFLVDFKP | STRVRQCRAL | | 540 |
| | | | | | |
| AtNHX1 | -------- | -------- | -------- | | 538 |
| ScNHX1 | KPVFLDNVSP | SLQDSATQSP | ADFSSQNH- | | 633 |
| HsNHE6 | LVLPMDDSEP | PLNLLDNTRH | GPA----- | | 669 |
| CeNHE1 | D-------- | -------- | -------- | | 541 |

Figure 2(b)-1

| | | | | | |
|---|---|---|---|---|---|
| AtNHX1 | MLDS LVSK LP | SLSTS DHAS V | VALNLF VAL L | CAC IVLGHLL | 40 |
| AtNHX2 | - - - - TEFVT | NKLAAEHPQ - | IP ISVF IAI L | CLCL VIGHLL | 40 |
| AtNHX3 | - - - - - - - - | - - - - - - - - - | - - - - - - MML | VLS FVLGHVL | 13 |
| AtNHX1 | EENR - - WMNE | SITALLIGLG | TGV TILLISK | GKSS - HLLVF | 77 |
| AtNHX2 | EENR - - WVNE | SITAILVGAA | SGI VILLISK | GKSS - HILVF | 77 |
| AtNHX3 | RR HR F HYLPE | AISGSLLIGLI | VGI LANLSDT | ETS IRTWFNF | 53 |
| AtNHX1 | SE DLFF IYLL | PP IIFNAGFQ | VKKK QF FRNF | VTIMLFGAVG | 117 |
| AtNHX2 | DE ELFF IYLL | PP IIFNAGFQ | VKKKKF FHNF | LTIMSFGVIG | 117 |
| AtNHX3 | HE EF FLFLL | PPIIF QSGFS | LQPKPF FSNF | GAJVTFALIG | 93 |
| AtNHX1 | T IISCI IISL | GVTQFFKKLD | FKGL SARDYL | AIGAIFAATD | 157 |
| AtNHX2 | VF ISTV IISF | GTWWLFPRLG | FKGL SARDYL | AIGT IFSSTD | 157 |
| AtNHX3 | TF VASVVTGG | LVYLGGSMYL | MYKLPF VECL | MFGALISATD | 133 |
| AtNHX1 | SVCTLQVLNQ | DETPL - LYSL | VFGEGVVNDA | TSVVVFNAIQ | 196 |
| AtNHX2 | TVCTLQI LHQ | DETPL - LYSL | VFGEGVVNDA | TSVVLFNAVQ | 196 |
| AtNHX3 | PVTVLS IFQD | VGTDVN LYAL | VFGES VLNDA | MAIS LYRTMS | 173 |
| AtNHX1 | SF DLTHL NHE | AAF HLLGNFL | YLF LLS TLLG | AATGL ISAY V | 236 |
| AtNHX2 | KIQFES LTGW | TALQ VFGNFL | YLF STS TLLG | IGVGLITSFV | 236 |
| AtNHX3 | LVNRQS SSGE | HFFMV IRFF | ETFAGSMSAG | VGVGFTSALL | 213 |
| AtNHX1 | IKKLYFG - RH | STDREVALMM | LMAYLS YMLA | ELFDLSGILT | 275 |
| AtNHX2 | LKTLYFG - RH | STTRELAIMV | LMAYLS YMLA | ELFSLSGILT | 275 |
| AtNHX3 | FR YAGLDTEN | LQNLECCLFV | LF PYFS YMLA | EGVGLSGIVS | 253 |

Figure 2(b)-2

| | | | | | |
|---|---|---|---|---|---|
| AtNHX1 | VFFCGIVMSH | YTWHNVTESS | RITTKHTFAT | LSFLAETFIF | 315 |
| AtNHX2 | VFFCGVLMSH | YASYNVTESS | RITSRHVFAM | LSFIAETFIF | 315 |
| AtNHX3 | ILFTGIVMKR | YTFSNLSEAS | QSFVSSFFHL | ISSLAETFTF | 293 |
| | | | | | |
| AtNHX1 | LYVGMD-ALD | IDKWRSVSDT | PGTSIAVSSJ | LMGLVMVGRA | 354 |
| AtNHX2 | LYVGTD-ALD | FTKWKTSSLS | FGGTLGVSGM | ITALVLLGRA | 354 |
| AtNHX3 | IYMGFDIAME | QHSWSHVG-- | ILFSIVSSF | TDRQ------ | 325 |
| | | | | | |
| AtNHX1 | AFVFPLSFLS | NLAKNQ--S | EKINFNMQVV | IWWSGLMRGA | 392 |
| AtNHX2 | AFVFPLSVLT | NFMNRHTERN | ESITFKHQVI | IWWAGLMRGA | 394 |
| AtNHX3 | ---------- | ---------- | ---------- | ---------- | 325 |
| | | | | | |
| AtNHX1 | VSMALAYNKF | TRAGHTDVRG | NAIMITSTIT | VCLFSTVVFG | 432 |
| AtNHX2 | VSIALAFKQF | TYSGVTLDPV | NAAMVTNTTI | VLFTTLVFG | 434 |
| AtNHX3 | ---------- | ---------- | ---------- | ---------- | 325 |
| | | | | | |
| AtNHX1 | MLTKPLISYL | LPHQNATTSM | LSDDNTPKSI | HIP--LDQD | 470 |
| AtNHX2 | FLTKPLVNYL | LPQDAISHNTG | NRGKRTEPGS | PKEDATLPLL | 474 |
| AtNHX3 | ---------- | ---------- | ---------- | ---------- | 325 |
| | | | | | |
| AtNHX1 | SFIEPSGNHN | VPRPDSIRGF | LTRPTRTVHY | YWRQFDDSFM | 510 |
| AtNHX2 | SFDESASTNF | NRARDSISLL | MEQPVYTLR | YWRKFDDTYM | 514 |
| AtNHX3 | ---------- | ---------- | ---------- | ---------- | 325 |
| | | | | | |
| AtNHX1 | RPVFGGRGFV | PFVPGSPTER | NPPDLSKA | | 538 |
| AtNHX2 | RPIFGGPRRE | NQPEC----- | -------- | | 529 |
| AtNHX3 | ---------- | ---------- | -------- | | 325 |

Figure 2(c)

|  |  |  |  |  |  |
|---|---|---|---|---|---|
| AtNHX3 | MMLVLSFVLG | HVLRRHRFHY | LPEASGSLLI | GLIVGILANI | 40 |
| AtNHX4 | MMLVLSFVLG | HVLRRHRFHY | LPEASGSLLI | GLIVGILANI | 40 |
| AtNHX3 | SDTETSIRTW | FNFHEEFFFL | FLLPPIFQS | GFSLQPKPFF | 80 |
| AtNHX4 | SDTETSIRTW | FNFHEEFFFL | FLLPPIFQS | GFSLQPKPFF | 80 |
| AtNHX3 | SNFGAIVTFA | IIGTFVASVV | TGGLVYLGGS | MYLMYKLPFV | 120 |
| AtNHX4 | SNFGAIVTFA | IIGTFVASVV | TGGLVYLGGS | MYLMYKLPFV | 120 |
| AtNHX3 | ECLMFGALIS | ATDPVTVLSI | FQDVGTDVNL | YALVFGESVL | 160 |
| AtNHX4 | ECLMFGALIS | ATDPVTVLSI | FQDVGTDVNL | YALVFGESVL | 160 |
| AtNHX3 | NDAMAISLYR | TMSLVNRQSS | SGEHFFMVVI | RFFETFAGSM | 200 |
| AtNHX4 | NDAMAISLYR | TMSLVNRQSS | SGEHFFMVVI | RFFETFAGSM | 200 |
| AtNHX3 | SAGVGVGFTS | ALFKYAGLD | TENLQNLECC | LFVLFPYFSY | 240 |
| AtNHX4 | SAGVGVGFTS | ALISFLESSI | FLIRCHMAKN | VL-------- | 232 |
| AtNHX3 | MLAEGVGLSG | IVSILFTGIV | MKRYTFSNLS | EASQSFVSSF | 280 |
| AtNHX4 | ---------- | ---------- | ---------- | ---------- | 232 |
| AtNHX3 | FHLISSLAET | FTFIYMGFDI | AMEQHSWSHV | GFILFSIVSS | 320 |
| AtNHX4 | ---------- | ---------- | ---------- | ---------- | 232 |
| AtNHX3 | FTDRQ | 325 | | | |
| AtNHX4 | ----- | 232 | | | |

Figure 5(a)-1

```
ATGTTGGATTCTCTAGTGTCGAAACTGCCTTCGTTATCGACATCTGATCAC
GCTTCTGTGGTTGCGTTGAATCTCTTTGTTGCACTTCTTTGTGCTTGTATT
GTTCTTGGTCATCTTTTGGAAGAGAATAGATGGATGAACGAATCCATCACC
GCCTTGTTGATTGGGCTAGGCACTGGTGTTACCATTTTGTTGATTAGTAAA
GGAAAAAGCTCGCATCTTCTCGTCTTTAGTGAAGATCTTTTCTTCATATAT
CTTTTGCCACCCATTATATTCAATGCAGGGTTTCAAGTAAAAAGAAGCAG
TTTTTCCGCAATTTCGTGACTATTATGCTTTTTGGTGCTGTTGGGACTATT
ATTTCTTGCACAATCATATCTCAGGTGTAACACAGTTCTTTAAGAAGTTG
GACATTGGAACCTTTGACTTGGGTGATTATCTTGCTATTGGTGCCATATTT
GCTGCAACAGATTCAGTATGTACACTGCAGGTTCTGAATCAAGACGAGACA
CCTTTGCTTTACAGTCTTGTATTCGGAGAGGGTGTTGTGAATGATGCAACG
TCAGTTGTGGTCTTCAACGCGATTCAGAGCTTTGATCTCACTCACCTAAAC
CACGAAGCTGCTTTTCATCTTCTTGGAAACTTCTTGTATTTGTTTCTCCTA
AGTACCTTGCTTGGTGCTGCAACCGGTCTGATAAGTGCGTATGTTATCAAG
AAGCTATACTTTGGAAGGCACTCAACTGACCGAGAGGTTGCCCTTATGATG
CTTATGGCGTATCTTCTTATATGCTTGCTGAGCTTTTCGACTTGAGCGGT
ATCCTCACTGTGTTTTCTGTGGTATTGTGATGTCCCATTACACATGGCAC
AATGTAACGGAGAGCTCAAGAATAACAACAAAGCATACCTTTGCAACTTTG
TCATTTCTTGCGGAGACATTTATTTTCTTGTATGTTGGAATGGATGCCTTG
GACATTGACAAGTGGAGATCCGTGAGTGACACACCGGGAACATCGATCGCA
GTGAGCTCAATCCTAATGGGTCTGGTCATGGTTGGAAGAGCAGCGTTCGTC
TTTCCGTTATCGTTTCTATCTAACTTAGCCAAGAAGAATCAAAGCGAGAAA
ATCAACTTTAACATGCAGGTTGTGATTTGGTGGTCTGGTCTCATGAGAGGT
GCTGTATCTATGGCTCTTGCATACAACAAGTTTACAAGGGCCGGGCACACA
GATGTACGCGGGAATGCAATCATGATCACGAGTACGATAACTGTCTGTCTT
TTTAGCACAGTGGTGTTTGGTATGCTGACCAAACCACTCATAAGCTACCTA
TTACCGCACCAGAACGCCACCACGAGCATGTTATCTGATGACAACACCCCA
AAATCCATACATATCCCTTTGTTGGACCAAGACTCGTTCATTGAGCCTTCA
GGGAACCACAATGTGCCTCGGCCTGACAGTATACGTGGCTTCTTGACACGG
CCCACTCGGAACCGTGCATTACTAACTGGAGACAATTTGATGACTCTTTCA
TGCGACCCGTCTTTGGAGGTCGTGGCTTTGTACCCTTTGTTCCAGGTTCTC
CAACTGAGAGAAACCCTCCTGATCTTAGTAAGGCTTGAGGGTAACGTGGAA
GAAAAGCTTTGATTTTTTTGGTAGAAAGGGTGATTCAAATTATGCTTTT
GTGTAAATTATCCATTTGTAATATTGTTTGTGAGGACAGAAATCTGTCCTA
ACGTTTGAGAGCAGAAAGCAAACATGGCAACTTTGAAGTGTTTGATTGA
TGTATGTAATTATATTCATATTTGTTTTGTTGTAACACAAACTACACATTT
GTTTATGTTTTGAATTTGGTTTTTGCTTCGAAAAAAAAAAAAAAAAA
```

Figure 5(a)-2

```
MLDSLVSKLPSLSTSDHASVVALNLFVALLCACIVLGHLLEENRWMNESIT
ALLIGLGTGVTILLISKGKSSHLLVFSEDLFFIYLLPPIIFNAGFQVKKKQ
FFRNFVTIMLFGAVGTIISCTIISLGVTQFFKKLDIGTFDLGDYLAIGAIF
AATDSVCTLQVLNQDETPLLYSLVFGEGVVNDATSVVVFNAIQSFDLTHLN
HEAAFHLLGNFLYLFLLSTLLGAATGLISAYVIKKLYFGRHSTDREVALMM
LMAYLSYMLAELFDLSGILTVFFCGIVMSHYTWHNVTESSRITTKHTFATL
SFLAETFIFLYVGMDALDIDKWRSVSDTPGTSIAVSSILMGLVMVGRAAFV
FPLSFLSNLAKKNQSEKINFNMQVVIWWSGLMRGAVSMALAYNKFTRAGHT
DVRGNAIMITSTITVCLFSTVVFGMLTKPLISYLLPHQNATTSMLSDDNTP
KSIHIPLLDQDSFIEPSGNHNVPRPDSIRGFLTRPTRNRALLTGDNLMTLS
CDPSLEVVALYPLFQVLQLRETLLILVRLEGNVEEKL
```

Figure 5(b)-1

```
1    TTCGCGGCCGCGTCTCTCTCTATTTCCAGTAAAAAATCGAAATTTC
47   GTATAATTTCCTCAGTCCCGTAATTTTCTCCTTTTTTTCTTCCC
92   CAATTCCTTCAATTTTCGAATTCGCCTCTCTGTTTCGTTCCTCGT
137  AGACGAAGAAGAAGAAGAATCTCAGGTTTTAGCTTTCGAAGCTTC
182  CAAAATTTTGAATTTTGATCTTCTGGGCTCTTTTGTAAATCAGAC
227  TGAAGATATTTAGATTACCCAGAAGTTGTTCAAGGAATGGTTTCA
272  GTGGACAGCACGGAAAGATAAAAGAGACTTTTTTTTCCAGATTTT
317  GCTGATCCAAAATCTGAATAGTTGTTCATGTTCTTGGATCAAATC
362  TGGAAGAGGAAGTTTGTTGGATCTAGAAGAAGATAACAATGTTG
                                               M   L         2
407  GATTCTCTAGTGTCGAAACTGCCTTCGTTATCGACATCTGATCAC
     D   S   L   V   S   K   L   P   S   L   S   T   S   D   H    17
452  GCTTCTGTGGTTGCGTTGAATCTCTTTGTTGCACTTCTTTGTGCT
     A   S   V   V   A   L   N   L   F   V   A   L   L   C   A    32
497  TGTATTGTTCTTGGTCATCTTTTGGAAGAGAATAGATGGATGAAC
     C   I   V   L   G   H   L   L   E   E   N   R   W   M   N    47
542  GAATCCATCACCGCCTTGTTGATTGGGCTAGGCACTGGTGTTACC
     E   S   I   T   A   L   L   I   G   L   G   T   G   V   T    62
587  ATTTTGTTGATTAGTAAAGGAAAAAGCTCGCATCTTCTCGTCTTT
     I   L   L   I   S   K   G   K   S   S   H   L   L   V   F    77
632  AGTGAAGATCTTTTCTTCATATATCTTTTGCCACCCATTATATTC
     S   E   D   L   F   F   I   Y   L   L   P   P   I   I   F    92
677  AATGCAGGGTTTCAAGTAAAAAAGAAGCAGTTTTTCCGCAATTTC
     N   A   G   F   Q   V   K   K   Q   F   F   R   N   F        107
722  GTGACTATTATGCTTTTTGGTGCTGTTGGGACTATTATTTCTTGC
     V   T   I   M   L   F   G   A   V   G   T   I   I   S   C    122
767  ACAATCATATCTCTAGGTGTAACACAGTTCTTTAAGAAGTTGGAC
     T   I   I   S   L   G   V   T   Q   F   F   K   K   L   D    137
812  ATTGGAACCTTTGACTTGGGTGATTATCTTGCTATTGGTGCCATA
     I   G   T   F   D   L   G   D   Y   L   A   I   G   A   I    152
857  TTTGCTGCAACAGATTCAGTATGTACACTGCAGGTTCTGAATCAA
     F   A   A   T   D   S   V   C   T   L   Q   V   L   N   Q    167
902  GACGAGACACCTTTGCTTTACAGTCTTGTATTCGGAGAGGGTGTT
     D   E   T   P   L   L   Y   S   L   V   F   G   E   G   V    182
947  GTGAATGATGCAACGTCAGTTGTGGTCTTCAACGCGATTCAGAGC
     V   N   D   A   T   S   V   V   V   F   N   A   I   Q   S    197
```

Figure 5(b)-2

```
992   TTTGATCTCACTCACCTAAACCACGAAGCTGCTTTTCATCTTCTT
       F  D  L  T  H  L  N  H  E  A  A  F  H  L  L      212
1037  GGAAACTTCTTGTATTTGTTTCTCCTAAGTACCTTGCTTGGTGCT
       G  N  F  L  Y  L  F  L  L  S  T  L  L  G  A      227
1082  GCAACCGGTCTGATAAGTGCGTATGTTATCAAGAAGCTATACTTT
       A  T  G  L  I  S  A  Y  V  I  K  K  L  Y  F      242
1127  GGAAGGCACTCAACTGACCGAGAGGTTGCCCTTATGATGCTTATG
       G  R  H  S  T  D  R  E  V  A  L  M  M  L  M      257
1172  GCGTATCTTTCTTATATGCTTGCTGAGCTTTTCGACTTGAGCGGT
       A  Y  L  S  Y  M  L  A  E  L  F  D  L  S  G      272
1217  ATCCTCACTGTGTTTTTCTGTGGTATTGTGATGTCCCATTACACA
       I  L  T  V  F  F  C  G  I  V  M  S  H  Y  T      287
1262  TGGCACAATGTAACGGAGAGCTCAAGAATAACAACAAAGCATACC
       W  H  N  V  T  E  S  S  R  I  T  T  K  H  T      302
1307  TTTGCAACTTTGTCATTTCTTGCGGAGACATTTATTTTCTTGTAT
       F  A  T  L  S  F  L  A  E  T  F  I  F  L  Y      317
1352  GTTGGAATGGATGCCTTGGACATTGACAAGTGGAGATCCGTGAGT
       V  G  M  D  A  L  D  I  D  K  W  R  S  V  S      332
1397  GACACACCGGGAACATCGATCGCAGTGAGCTCAATCCTAATGGGT
       D  T  P  G  T  S  I  A  V  S  S  I  L  M  G      347
1442  CTGGTCATGGTTGGAAGAGCAGCGTTCGTCTTTCCGTTATCGTTT
       L  V  M  V  G  R  A  A  F  V  F  P  L  S  F      362
1487  CTATCTAACTTAGCCAAGAAGAATCAAAGCGAGAAAATCAACTTT
       L  S  N  L  A  K  K  N  Q  S  E  K  I  N  F      377
1532  AACATGCAGGTTGTGATTTGGTGGTCTGGTCTCATGAGAGGTGCT
       N  M  Q  V  V  I  W  W  S  G  L  M  R  G  A      392
1577  GTATCTATGGCTCTTGCATACAACAAGTTTACAAGGGCCGGGCAC
       V  S  M  A  L  A  Y  N  K  F  T  R  A  G  H      407
1622  ACAGATGTACGCGGGAATGCAATCATGATCACGAGTACGATAACT
       T  D  V  R  G  N  A  I  M  I  T  S  T  I  T      422
1667  GTCTGTCTTTTTAGCACAGTGGTGTTTGGTATGCTGACCAAACCA
       V  C  L  F  S  T  V  V  F  G  M  L  T  K  P      437
1712  CTCATAAGCTACCTATTACCGCACCAGAACGCCACCACGAGCATG
       L  I  S  Y  L  L  P  H  Q  N  A  T  T  S  M      452
1757  TTATCTGATGACAACACCCCAAAATCCATACATATCCCTTTGTTG
       L  S  D  D  N  T  P  K  S  I  H  I  P  L  L      467
```

Figure 5(b)-3

```
1802  GACCAAGACTCGTTCATTGAGCCTTCAGGGAACCACAATGTGCCT
       D   Q   D   S   F   I   E   P   S   G   N   H   N   V   P      482
1847  CGGCCTGACAGTATACGTGGCTTCTTGACACGGCCCACTCGGAAC
       R   P   D   S   I   R   G   F   L   T   R   P   T   R   N      497
1892  CGTGCATTACTAACTGGAGACAATTTGATGACTCTTTCATGCGAC
       R   A   L   L   T   G   D   N   L   M   T   L   S   C   D      512
1937  CCGTCTTTGGAGGTCGTGGCTTTGTACCCTTTGTTCCAGGTTCTC
       P   S   L   E   V   V   A   L   Y   P   L   F   Q   V   L      527
1982  CAACTGAGAGAAACCCTCCTGATCTTAGTAAGGCTTGAGGGTAAC
       Q   L   R   E   T   L   L   I   L   V   R   L   E   G   N      542
2027  GTGGAAGAAAAGCTTTGA
       V   E   E   K   L                                               547
```

Figure 8 (a)

[SEQ ID NO:21]

```
1    mpdskhwvil lfrrdgdddd ddgqdpalqe lysswalfil lvlligallt
51   syyvqskkir aihetvisvf vgmvvgliir vspgliiqnm vsfhstyffn
101  vllppiilns gyelhqsnff rnigtiltfa fagtfisavt lgvlvyifsf
151  lnfenlsmtf vealsmgatl satdpvtvla ifnsykvdqk lytiifgesi
201  lndavaivmf etlqqfqgkt lhfftlfsgi gifiitffis lligvsigli
251  talllkysyl rrypsiesci illmaytsyf fsngchmsgv vsllfcgitl
301  khyaffnmsy kaklstkyvf rvlaqlsenf ifiylgmslf tqvdlvykpi
351  filittvavt asrymnvfpl snllnkfhrq rngnlidhip ysyqmmlfwa
401  glrgavgval aagfegenaq tlrattlvvv vltliifggt tarmleilhi
451  etgvaadvds dteigmlpwq qspefdlens amelsdasae pvvvdqqftt
501  ehfdegniap tlskkvsstf eqyqraagaf nqffhssrdd qaqwltrfde
551  evikpvller dnlkngtkk
```

Figure 8 (b)

[SEQ ID NO:22]

```
1   mlskvllnia fkvllttakr avdpddddel lpspdlpgsd dpiagdpdvd
51  lnpvteemfs swalfimlll lisalwssyy ltqkriravh etvlsifygm
101 vigliirmsp ghyiqdtvtf nssyffnvll ppiilnsgye lnqvnffnnm
151 lsilifaipg tfisavvigi ilyiwtflgl esidisfada msvgatlsat
201 dpvtilsifn aykvdpklyt iifgeslInd aisivmfetc qkfhgqpatf
251 ssvfegaglf lmtfsvslli gvligilval llkhthirry pqiesclill
301 iayesyffsn gchmsgivsl lfcgitlkhy ayynmsrrsq itikyifqll
351 arlsenfifi ylglelftev elvykpllii vaaisicvar wcavfplsqf
401 vnwiyrvkti rsmsgitgen isvpdeipyn yqmmtfwagl rgavgvalal
451 giqgeykftl latvlvvvvl tviifggtta gmlevlnikt gciseedtsd
501 defdieapra inllngssiq tdlgpysdnn spdisidqfa vssnknlpnn
551 isttggntfg glnetentsp nparssmdkr nlrdklgtif nsdsqwfqnf
601 deqvlkpvfl dnvspslqds atqspadfss qnh
```

Figure 8 (c)

[SEQ ID NO:23]

```
1    caagaagcta tacattggaa ggcattctac tgaccgtgag gttgcccttag
51   tgatgctcat ggcttacctt tcatatatgc tggctgagtt gctagatttg
101  agcggcattc tcaccgtatt cttctgtggt attgtaatgt cacattacac
151  ttggcataac gtcacagaga gttcaagagt tacaacaaag cacgcatttg
201  caactctgtc cttcattgct gagactttc tcttcctgta tgttgggatg
251  gatgcattgg atattgaaaa atgggagntt nccagtgaca gacctggnaa
301  atccattngg gtaagctcaa ttttgctagg gattggttcc tgattggaag
351  ngctgctttt gnaattcccc tggtggtc
```

Figure 8 (d)

[SEQ ID NO:24]

```
1    gtttggtaat tggaggaggt ggagtaatgg agctcgggtt ggggatgggg
51   atggggctgg gcgacccgnc tgcggactac ggctcgatcg cggcggtggg
101  gatgttcgtg gcgctcatct gcgtctgcat cgtcgtcggc cacctcctcg
151  aggagagccg atggatgaac gagtccatca ccgcgctaat catcgggttg
201  ggtacttgga ggagtgnttt tgnatggtgt cgagctggaa gcactcggna
251  tactggtgtt cagcgagg
```

Figure 8 (e)

[SEQ ID NO:25]

```
1    acattccctg aaagnactgc tggacntttg agggctcgga tgcctgtaga
51   tccaggactc aaaggatgnt gagctagagg ttgttgggat ggtgaagttt
101  gcttaccaag ggccatttac attgtctggc atcaaactat gcccagccac
151  tgatggcacg gctcagttta atgaggctgg ccacaccttc tccagtggga
201  gttatctgtg catctaattg gtaccttctt tgtattgtag ttgttacttt
251  acccttgatt tgttcggttt gcttctaaag caggttgtga aattcctatt
301  gtatgtngtg acgcttgttt gtttttgag gctggaaatt acatcatgtt
351  tttgatttgt ctattaaaaa aaaaaaaaa
```

Figure 8 (f)

[SEQ ID NO:26]

```
1    gtcaaaactc atccctcctc ttccatttgc atattcttct ttatcatctt
51   ttcttcccta aattagagtc tatccttccg cccatagtct ttgacaccct
101  tttcaaaatt ctagaacaag aattttattc ttcatatata tatatatata
151  tatccaatta accatctcaa tctcatattc acatacct cataaccat
201  ccataacatc cttaaaaacc ctctaagccc tttcaaactt tgatttgtaa
251  ttgtttctct tataagtctt aacctgcaca aatcaatttt aatttcttat
301  gttcatatag ttatgaatga ttgaaaaaaa cacaaatgac tccagttatc
351  tgtgagatct ctatgataaa ctctactctc cagacgcagg acacatttag
401  ttcaatcttt ctctgttgtt ttcctctact ggttctatat tttctcatga
451  attattaatt aatcctatat tctttctttt caatacaaat ttagtttcat
501  taattctatc aacataatca attaaactac atagttagaa aaatagtact
551  attaccacga tcactcaaag ttttttagtt tttaacaaac antctg
```

Figure 8 (g)

[SEQ ID NO:27]

```
1    atttacatgg ttataccagt tatcttgagc acttatgcat catccagtga
51   tcagttttgc ttccattcag actgatgggt ctggcagaag taatgtattc
101  tggtggactt acatctatca gcgatgatga aacttgatga tcagtttttt
151  tagttgaaaa attctgcaag aacagctact taatgctcta ttgtgtatcg
201  caggcacaca tcagctgctg atgtctgcta tacttctgta ctctcactat
251  agctcatcta tgacgtctag acatgctagc gtatgtgtan nnnacatcgc
301  gctagtatgt atactctcac atcatatgct actgttctat atagaactat
351  gtgatagcta ctgctatact gctgtcatac agagtcccgt taatatcaat
401  gctatttgc tttcctcaaa gaaaaaagga aatgactttc cttttgatta
451  tatatttgat ccaggttttc ggcttgctga ctaagcctct gattaatctc
501  ctcgtcccac caagacctgg ca
```

Figure 8 (h)

[SEQ ID NO:28]

```
1    tttccgttat cgtttctatc taacttagcc aagaagaatc aaagcgagaa
51   aatcaacttt aacatgcagg ttgtgatttg gtggtctggt ctcatgagag
101  gtgctgtatc tatggctctt gcatacaaca agtttacaag ggccgggcac
151  acagatgtac gngggaatgc aatcatgatc acgngtacgn taactgtctg
201  tnttttagc acagtggtgt ttggtatgct gaccaaacca ntcataagct
251  acctatttac cgnaccanga accgtcatca acgnggcatg tttatcttgn
301  attncaaata acccnaanaa tccnatacca
```

GENETIC ENGINEERING SALT TOLERANCE IN CROP PLANTS

CROSS REFERENCE TO RELATED APPLICATIONS

This application claims priority from U.S. application Nos. 60/078,474 filed Mar. 18, 1998 and 60/116,111 filed Jan. 15, 1999, which are incorporated by reference herein in their entirety.

BACKGROUND OF THE INVENTION

Environmental stress due to salinity is one of the most serious factors limiting the productivity of agricultural crops, which are predominantly sensitive to the presence of high concentrations of salts in the soil. Large terrestrial areas of the world are affected by levels of salt inimical to plant growth. It is estimated that 35–45% of the 279 million hectares of land under irrigation is presently affected by salinity. This is exclusive of the regions classified as arid and desert lands, (which comprises 25% of the total land of our planet). Salinity has been an important factor in human history and in the life spans of agricultural systems. Salt impinging on agricultural soils has created instability and has frequently destroyed ancient and recent agrarian societies. The Sumerian culture faded as a power in the ancient world due to salt accumulation in the valleys of the Euphrates and Tigris rivers. Large areas of the Indian subcontinent have been rendered unproductive through salt accumulation and poor irrigation practices. In this century, other areas, including vast regions of Australia, Europe, southwest USA, the Canadian prairies and others have seen considerable declines in crop productivity.

Although there is engineering technology available to combat this problem, though drainage and supply of high quality water, these measures are extremely costly. In most of the cases, due to the increased need for extensive agriculture, neither improved irrigation efficiency nor the installation of drainage systems is applicable. Moreover, in the arid and semi-arid regions of the world water evaporation exceeds precipitation. These soils are inherently high in salt and require vast amounts of irrigation to become productive. Since irrigation water contains dissolved salts and minerals, an application of water is also an application of salt that compounds the salinity problem.

Increasing emphasis is being given to modify plants to fit the restrictive growing conditions imposed by salinity. If economically important crops could be manipulated and made salt resistant, this land could be farmed resulting in greater sales of seed and greater yield of useful crops. Conventional breeding for salt tolerance has been attempted for a long time. These breeding practices have been based mainly on the following strategies: a) the use of wide crosses between crop plants and their more salt-tolerant wild relatives (1), b) screening and selecting for variation within a particular phenotype (2), c) designing new phenotypes through recurrent selection (3). The lack of success in generating tolerant varieties (given the low number of varieties released and their limited salt tolerance) (4) would suggest that conventional breeding practices are not enough and that in order to succeed a breeding program should include the engineering of transgenic crops (5).

Several biochemical pathways associated with stress tolerance have been characterized in different plants and a few of the genes involved in these processes have been identified and in some cases the possible role of proteins has been investigated in transgenic/overexpression experiments. Several compatible solutes have been proposed to play a role in osmoregulation under stress. Such compatible solutes, including carbohydrates (6), amino acids (7) and quaternary N-compounds (8) have been shown to increase osmoregulation under stress. Also, proteins that are normally expressed during seed maturation (LEAs, Late Embriogenesis Abundant proteins) have been suggested to play a role in water retention and in the protection of other proteins during stress. The overexpression of LEA in rice provided a moderate benefit to the plants during water stress (9, 10). A single gene (sod2) coding for a $Na^+/H^+$ antiport has been shown to confer sodium tolerance in fission yeast (11, 12), although the role of this plasma membrane-bound protein appears to be only limited to yeast. One of the main disadvantages of using this gene for transformation of plants is associated with the typical problems encountered in heterologous gene expression, i.e. incorrect folding of the gene product, targeting of the protein to the target membrane and regulation of the protein function.

Plants that tolerate and grow in saline environments have high intracellular salt levels. A major component of the osmotic adjustment in these cells is accomplished by ion uptake. The utilization of inorganic ions for osmotic adjustment suggests that salt-tolerant plants must be able to tolerate high levels of salts within their cells. However, enzymes extracted from these plants show high sensitivity to salt. The sensitivity of the cytosolic enzymes to salt would suggest that the maintenance of low cytosolic sodium concentration, either by compartmentation in cell organelles or by exclusion through the plasma membrane, must be necessary if the enzymes in the cell are to be protected from the inimical effects of salt.

Plant cells are structurally well suited to the compartmentation of ions. Large membrane-bound vacuoles are the site for a considerable amount of sequestration of ions and other osmotically active substances. A comparison of ion distribution in cells and tissues of various plant species indicates that a primary characteristic of salt tolerant plants is their ability to exclude sodium out of the cell and to take up sodium and to sequester it in the cell vacuoles. Transport mechanisms could actively move ions into the vacuole, removing the potentially harmful ions from the cytosol. These ions, in turn, could act as an osmoticum within the vacuole, which would then be responsible for maintaining water flow into the cell. Thus, at the cellular level both specific transport systems for sodium accumulation in the vacuole and sodium extrusion out of the cell are correlated with salt tolerance.

SUMMARY OF THE INVENTION

We have isolated the first such system of intracellular salt management. We identified the presence of a functional vacuolar $Na^+/H+$ antiport in the vacuolar membrane of higher plants (13, 14, 15, 16, 17, 18).

We have demonstrated the $Na^+/H^+$ antiport function in isolated tonoplast membranes and in intact vesicles and we showed that the activity of antiport molecules was salt dependent. Neither a protein sequence nor a gene encoding the antiport were identified in previously published work. We have now identified nucleic acid molecules coding for plant $Na^+/H^+$ antiports, the nucleic acid molecules and polypeptides produced by the nucleic acid molecules being the subject of the present invention. These polypeptides are useful for the extrusion of sodium ions from the cytosol, either through the accumulation of sodium ions into the vacuoles or into the extracellular space, thus providing the most important trait for salt tolerance in plants. These nucleic acid molecules, preferably genes, are useful for the engineering of salt tolerant plants by transformation of salt-sensitive crops overexpressing one or more of these nucleic acid molecules under the control of constitutively active promoters or under the control of conditionally-induced promoters. *Agrobacterium tumefaciens*-mediated transformation or particle-bombardment-mediated transformation are useful for depending upon the plant species.

The invention includes an isolated nucleic acid molecule encoding a PNHX transporter polypeptide, or a fragment of a polypeptide having $Na^+/H^+$ transporter activity and capable of increasing salt tolerance in a cell.

The invention also relates to an isolated nucleic acid molecule encoding a THX transporter polypeptide, PNHX transporter polypeptide, or a fragment of a polypeptide having $Na^+/H^+$ transporter activity and capable of increasing salt tolerance in a cell, comprising a nucleic acid molecule selected from the group consisting of:
(a) a nucleic acid molecule that hybridizes to all or part of a nucleic molecule in SEQ ID NO:1, SEQ ID NO:3, SEQ ID NO:17, SEQ ID NO:19, or a complement thereof under moderate or high stringency hybridization conditions, wherein the nucleic acid molecule encodes a TNHX transporter polypeptide, a PNHX transporter polypeptide or a polypeptide having $Na^+/H^+$ transporter activity and capable of increasing salt tolerance in a cell;
(b) a nucleic acid molecule degenerate with respect to (a), wherein the nucleic molecule encodes a TNHX transporter polypeptide, a PNHX transporter polypeptide or a polypeptide having $Na^+/H^+$ transporter activity and capable of increasing salt tolerance in a cell.

The hybridization conditions preferably comprise moderate (also called intermediate) or high stringency conditions selected from the conditions in Table 4.

The invention also includes an isolated nucleic acid molecule encoding a THX transporter polypeptide or a PNHX transporter polypeptide, or a fragment of a polypeptide having $Na^+/H^+$ transporter activity and capable of increasing salt tolerances in a cell, comprising a nucleic acid molecule selected from the group consisting of:
(a) the nucleic acid molecule of the coding strand shown in SEQ ID NO:1, SEQ ID NO:3, SEQ ID NO:17, SEQ ID NO:19 or a complement thereof;
(b) a nucleic acid molecule encoding the same amino acid sequence as a nucleotide sequence of (a); and
(c) a nucleic acid molecule having at least 17% identity with the nucleotide sequence of (a) and which encodes a THX transporter polypeptide or the PNHX transporter polypeptide or a polypeptide having $Na^+/H^+$ transporter activity.

The THX transporter polypeptide or the PNHX transporter polypeptide preferably comprises an AtNHX transporter polypeptide having $Na^+/H^+$ transporter activity and capable of increasing salt tolerance in a cell. The nucleic acid molecule may comprise all or part of a nucleotide sequence in SEQ ID NO:1, SEQ ID NO:3, SEQ ID NO:17 or SEQ ID NO:19 (or the coding region therof).

The invention also includes an AtNHX nucleic acid molecule isolated from *Arabidopsis thaliana*, or a fragment thereof encoding a transporter polypeptide having $Na^+/H^+$ transporter activity and capable of increasing salt tolerance in a cell.

Another aspect of the invention relates to a recombinant nucleic acid molecule comprising a nucleic acid molecule and a constitutive promoter sequence or an inducible promoter sequence, operatively linked so that the promoter enhances transcription of the nucleic acid molecule in a host cell.

The nucleic acid molecule preferably comprises genomic DNA, cDNA or RNA. In another aspect, the nucleic acid molecule is chemically synthesized. The nucleic acid molecule is preferably isolated from *Arabidopsis thaliana*.

The nucleic acid molecule preferably encodes a TNHX transporter polypeptide or PNHX transporter polypeptide that is capable of extruding monovalent cations out of the cytosol of a cell to provide the cell with increased salt tolerance, wherein the monovalent cations are selected from at least one of the group consisting of sodium, lithium and potassium. The cell preferably comprises a plant cell. The monovalent cations are preferably extruded into a vacuole or into the extracellular space.

The invention also includes an isolated nucleic acid molecule comprising a nucleic acid molecule selected from the group consisting of 8 to 10 nucleotides of the nucleic acid molecules described above, 11 to 25 nucleotides of the nucleic acid molecules described above, and 26 to 50 nucleotides of the nucleic acid molecules described above.

The invention also includes an isolated oligonucleotide comprising at least about 10 nucleotides from a sequence selected from the group consisting of 5'-GCCATGTTGGATTCTCTAGTGTCG-3 SEQ ID NO:11, 5'-CCGAATTCTCAAAGCTTTTCTTCCACG-3' SEQ ID NO:12), 5'-CGGAATTCACAGAAAAACACAGTGAGGAT-3' SEQ ID NO:13), 5'-GCCATGTTGGATTCTCTAGTGTCG-3 SEQ ID NO:14), 5'-CCGAATTCTCAAAGCTTTTCTTCCACG-3' SEQ ID NO:15), 5'CGGAATTCACAGAAAAACACAGTGAGGAT-3' SEQ ID NO:16) or another oligonucleotide described in this application.

Another aspect of the invention relates to a vector comprising a nucleic acid molecule of the invention. The vector preferably comprises a promoter selected from the group consisting of a super promoter, a 35S promoter of cauliflower mosaic virus, a drought-inducible promoter, an ABA-inducible promoter, a heat shock-inducible promoter, a salt-inducible promoter, a copper-inducible promoter, a steroid-inducible promoter and a tissue-specific promoter.

The invention also includes a host cell comprising a recombinant nucleic acid molecule of the invention, or progeny of the host cell.

The host cell is preferably selected from the group consisting of a fungal cell, a yeast cell, a bacterial cell, a microorganism cell and a plant cell. The plant, a plant part, a seed, a plant cell or progeny thereof preferably comprises the recombinant nucleic acid molecule of the invention. The plant part preferably comprises all or part of a leaf, a flower, a stem, a root or a tuber. The plant, plant part, seed or plant cell is preferably of a species selected from the group consisting of potato, tomato, *brassica*, cotton, sunflower, strawberries, spinach, lettuce, rice, soybean, corn, wheat, rye, barley, *atriplex*, sorgum, alfalfa, salicornia and the plant species or types in Table 5.

The plant, plant part, seed or plant cell preferably comprises a dicot plant or a monocot plant.

The invention also relates to a method for producing a recombinant host cell capable of expressing the nucleic acid molecule of the invention, the method comprising introducing into the host cell a vector of the invention. The invention also includes a method of producing a genetically transformed plant which expresses TNHX or PNHX transporter polypeptide, comprising regenerating a genetically transformed plant from a plant cell, seed or plant part of the invention. In one method, the genome of the host cell also includes a functional TNHX or PNHX gene. In another method, the genome of the host cell does not include a functional TNHX or PNHX gene. The invention also includes a transgenic plant produced according to a method of the invention.

Another aspect of the invention relates to a method for expressing a TNHX or PNHX transporter polypeptide in the host cell of the invention, a the plant, plant part, seed or plant cell of the invention, the method comprising culturing the host cell under conditions suitable for gene expression. A method for producing a transgenic plant that expresses elevated levels of PNHX transporter polypeptide relative to a non-transgenic plant, comprising transforming a plant with the vector of the invention. The invention also relates to an isolated polypeptide encoded by and/or produced from a nucleic acid molecule of the invention, or the vector of the invention.

The invention also relates to an isolated PNHX transporter polypeptide or a fragment thereof having $Na^+/H^+$ transporter activity and capable of increasing salt tolerance in a cell. The polypeptide of the invention preferably comprises an AtNHX transporter polypeptide. The polypeptide of the invention preferably comprises all or part of an amino acid sequence in SEQ ID NOS: 2, 4, 6, 8, 18, or 20 (FIG. 1). The invention also includes a polypeptide fragment of the AtNHX transporter polypeptide of the invention, or a peptide mimetic of the AtNHX transporter polypeptide, having $Na^+/H^+$ transporter activity and capable of increasing salt tolerance in a cell. The polypeptide fragment of the invention, preferably consists of at least 20 amino acids, which fragment has $Na^+/H^+$ transporter activity and is capable of increasing salt tolerance in a cell. The fragment or peptide mimetic of the invention is preferably capable of being bound by an antibody to a polypeptide of the invention. In one embodiment, the polypeptide of the invention is recombinantly produced.

The invention also includes an isolated and purified transporter polypeptide comprising the amino acid sequence of a TNHX transporter polypeptide or a PNHX transporter polypeptide, wherein the transporter polypeptide is encoded by a nucleic acid molecule that hybridizes under moderate or stringent conditions to a nucleic acid molecule in SEQ ID NOS: 1, 3, 5, 7, 17, or 19 (FIG. 1), a degenerate form thereof or a complement. The invention also includes a polypeptide comprising a sequence having greater than 28% sequence identity to a polypeptide of the invention (preferably a polypeptide in FIG. 1, such as SEQ ID NOS: 2, 4, 6, 8, 18, or 20).

The polypeptide of the invention, preferably comprises a $Na^+/H^+$ transporter polypeptide. The polypeptide is preferably isolated from *Arabidopsis thaliana*.

The invention also includes an isolated nucleic acid molecule encoding polypeptide of the invention (preferably a polypeptide in FIG. 1: SEQ ID NOS: 2, 4, 6, 8, 18, or 20).

Another aspect of the invention relates to an antibody directed against a polypeptide of the invention. The antibody of the invention, preferably comprises a monoclonal antibody or a polyclonal antibody.

The invention also relates to an isolated nucleic acid molecule encoding a TNHX transporter polypeptide or a PNHX transporter polypeptide, or a fragment of a polypeptide having $Na^+/H^+$ transporter activity and capable of increasing salt tolerance in a cell, comprising a nucleic acid molecule selected from the group consisting of:

(a) a nucleic acid molecule that hybridizes to all or part of a nucleic molecule in SEQ ID NO:5, SEQ ID NO:7, SEQ ID NO:9 or to a nucleic acid molecule comprising about nucleotides 1–1487 of SEQ ID NO:9, or a complement thereof under moderate or high stringency hybridization conditions, wherein the nucleic acid molecule encodes a TNHX transporter polypeptide, a PNHX transporter polypeptide or a polypeptide having $Na^+/H^+$ transporter activity and capable of increasing salt tolerance in a cell;

(b) a nucleic acid molecule degenerate with respect to (a), wherein the nucleic molecule encodes a TNHX polypeptide, a PNHX polypeptide or a polypeptide having $Na^+/H^+$ transporter activity and capable of increasing salt tolerance in a cell;

(c) the nucleic acid molecule of the coding strand shown in SEQ ID NO:5, SEQ ID NO:7), SEQ ID NO:9, nucleotides 1–1487 of SEQ ID NO:9, or an isolated nucleic acid molecule including about 1614 nucleic acids including SEQ ID NO:5, SEQ ID NO:7), nucleotides 1 to 1487 of the nucleic acid molecule in SEQ ID NO:9) or the complement thereof;

(d) a nucleic acid molecule encoding the same amino acid sequence as a nucleotide sequence of (c); and (e) a nucleic acid molecule having at least 17% sequence identity with the nucleotide sequence of (c) and which encodes a TNHX transporter polypeptide, a PNHX transporter polypeptide or a polypeptide having $Na^+/H^+$ transporter activity and capable of increasing salt tolerance in a cell.

The invention also includes a polypeptide produced from a nucleic acid molecule of the invention. The invention includes a polypeptide comprising (a) the amino acid sequence in SEQ ID NO:6, SEQ ID NO:8, SEQ ID NO:10; (b) amino acids 1 to 496 of SEQ ID NO:10; and (c) a sequence having greater than 28% homology to the polypeptide in (a) or (b). The invention includes a polypeptide comprising a $Na^+/H^+$ transporter polypeptide capable of increasing salt tolerance in a cell. The invention also includes a DNA molecule encoding the polypeptides of the invention.

The invention relates to a method of producing a genetically transformed plant which expresses or overexpresses a TNHX transporter polypeptide, a PNHX transporter polypeptide or a polypeptide having $Na^+/H^+$ transporter activity and capable of increasing salt tolerance in a cell and wherein the plant has increased salt tolerance, comprising:

a) cloning or synthesizing a TNHX nucleic acid molecule, a PNHX nucleic acid molecule or a nucleic acid molecule which codes for a $Na^+/H^+$ transporter polypeptide, wherein the polypeptide is capable of providing salt tolerance to a plant;

b) inserting the nucleic acid molecule in a vector so that the nucleic acid molecule is operably linked to a promoter;

c) inserting the vector into a plant cell or plant seed;

d) regenerating the plant from the plant cell or plant seed, wherein salt tolerance in the plant is increased compared to a wild type plant.

The invention includes a transgenic plant produced according to a method of the invention.

The nucleic acid molecules have several uses which will be discussed in more detail below. The nucleic acid molecules and the polypeptides are used in a method for protecting a plant from the adverse affects of a saline environment by incorporating a nucleic acid molecule for salt tolerance and/or the polypeptide of the invention into a plant. The nucleic acid molecules of the invention are also useful for the identification of homologous nucleic acid molecules from plant species, preferably salt tolerant species and genetically engineering salt tolerant plants of agricultural and commercial interest.

The invention relates to isolated nucleic acid molecules encoding a polypeptide for extrusion of sodium ions from the cytosol of a cell to provide the cell with salt tolerance. The nucleic acid molecules preferably comprise the nucleotide sequence in FIG. 1(a) or (b). The nucleic acid molecules may be DNA or RNA. The nucleic acid molecules may be used to transform a cell selected from the group consisting of a plant cell, a yeast cell and a bacterial cell. The sodium ions are extruded into a vacuole or out of the cell. The nucleic acid molecules encode a $Na^+/H^+$ exchanger polypeptide.

In a preferred embodiment, the nucleic acid molecules are isolated from *Arabidopsis thaliana*.

The invention includes an isolated nucleic acid molecule, comprising the DNA sequence in FIG. 1(a), (b), (c)(i), (c)(ii), (d) or (e). The invention also relates to an isolated nucleic acid molecule, comprising a sequence having greater than 17% homology to the sequences of the invention described in the preceding paragraphs.

In an alternate embodiment, the nucleic acid molecule consists of a sequence selected from the group consisting of 8 to 10 nucleotides of the nucleic acid molecules of the invention, 11 to 25 nucleotides of the nucleic acid molecule and 26 to 50 nucleotides of the nucleic acid molecules. These nucleic acid molecules hybridize to nucleic acid molecules described in the preceding paragraphs.

The nucleic acid molecule of the invention may have a sense or an antisense sequence.

In another embodiment, the invention is an isolated oligonucleotide consisting of a sequence selected from the group consisting of 5'-GCCATGTTGGATTCTCTAGTGTCG-3 SEQ ID NO:11, 5'-CCGAATTCTCAAAGCTTTTCTTCCACG-3' SEQ ID NO:12, 5'-CGGAATTCACAGAAAAACACAGTGAGGAT-3' SEQ ID NO:13, an oligonucleotide with an antisense sequence of 5'-GCCATGTTGGATTCTCTAGTGTCG-3 SEQ ID NO:14, an oligonucleotide with an antisense sequence of 5'-CCGAATTCTCAAAGCTTTTCTTCCACG-3' SEQ ID NO:15 and an oligonucleotide with an antisense sequence of 5'-CGGAATTCACAGAAAAACACAGTGAGGAT-3' SEQ ID NO:16. The invention includes an isolated oligonucleotide consisting of 5 to 15 nucleotides of these oligonucleotides. The invention includes an isolated oligonucleotide consisting of a sequence homologous to the oligonucleotide of claim 15 or claim 16.

In an alternate embodiment, the invention is an expression vector comprising a nucleic acid molecule of the invention. The expression vector preferably consists of a promoter selected from the group consisting of a super promoter, a $^{35}S$ promoter of cauliflower mosaic virus, a drought-inducible promoter, an ABA-inducible promoter, a heat shock-inducible promoter, a salt-inducible promoter, a copper-inducible promoter, a steroid-inducible promoter and a tissue-specific promoter.

The invention is a polypeptide produced from the nucleic acid molecules of the invention. The invention is also a polypeptide produced from the expression vector. The polypeptide is used for extrusion of sodium ions from the cytosol of a cell to provide the cell with salt tolerance.

In a preferred embodiment, the polypeptide has the amino acid sequence in FIGS. 1(a)–(e). The polypeptides may be homologous to the polypeptide in FIGS. 1(a)–(e). In an alternate embodiment, the polypeptides comprise a sequence having greater than 28% homology to the polypeptide in FIGS. 1(a)–(e). The polypeptides are $Na^+/H^{30}$ exchanger polypeptides.

The polypeptides are preferably isolated from *Arabidopsis thaliana*.

The invention includes peptides consisting of at least 5 amino acids of the polypeptides described in the preceding paragraphs. In another embodiment, the peptides consist of 41 to 75 amino acids of the polypeptides described in the preceding paragraphs.

The invention also includes isolated nucleic acid molecules encoding the polypeptides of the invention. The isolated nucleic acid molecule preferably encodes the polypeptide of FIGS. 1(a)–(e).

The polypeptides of the invention that extrude sodium ions from the cytosol of a cell to provide the cell with salt tolerance, preferably consist of an amiloride binding domain. The amiloride binding domain is between amino acids 82 to 90 in both AtNHX1 and AtNHX2. in FIGS. 1(a)–(e) and between amino acids 58 to 66 in both AtNHX3 and AtNHX4 in figures (d) and (e).

The invention also includes a monoclonal antibody or polyclonal antibody directed against a polypeptide of the invention.

Another embodiment of the invention includes a transformed microorganism comprising an isolated nucleic acid molecule of the invention. The invention also includes a transformed microorganism including an expression vector.

The invention includes a plant cell transformed with a nucleic acid molecule of the invention. The invention also includes a yeast cell transformed with the nucleic acid molecule of the invention. In another embodiment, the invention is a plant, plant part or seed, generated from a plant cell transformed with a nucleic acid molecule of the invention. The invention also relates to a plant, plant part, seed or plant cell transfected with a nucleic acid molecule of the invention. The plant, plant part, seed or plant cell is preferably selected from a species selected from the group consisting of potato, tomato, *brassica*, cotton, sunflower, strawberries, spinach, lettuce, rice, soybean, corn, wheat, rye, barley, *atriplex*, sorgum, alfalfa and salicornia and other plants in Table 5.

The invention also includes a method for producing a polypeptide of the invention by culturing a plant, plant part, seed or plant cell of the invention and recovering the expressed polypeptide from the culture.

The invention includes an isolated nucleic acid molecule encoding a polypeptide capable of extruding monovalent cations from the cytosol of a cell to provide the cell with increased salt tolerance. The nucleic acid molecule preferably includes the nucleotide sequence in FIGS. 1(a)–(e). The nucleic acid molecule is preferably DNA or RNA. The cell is preferably a plant cell, a yeast cell or a bacterial cell. The monovalent cations are preferably sodium, lithium or potassium. The monovalent cations are preferably extruded into a vacuole or out of the cell. The nucleic acid molecules preferably encode a $Na^+/H^+$ exchanger polypeptide. The nucleic acid molecule is preferably isolated from *Arabidopsis thaliana*.

The invention also includes an isolated nucleic acid molecule, including a sequence having greater than 17% homology to a sequence referred to in the preceding paragraph.

The invention also includes a nucleic acid molecule of 8 to 10 nucleotides, 11 to 25 or 26 to 50 nucleotides of a nucleic acid molecule of the invention.

The invention also includes a nucleic acid molecule which nucleic acid molecule hybridizes a nucleic acid molecule of the invention. The nucleic acid molecule comprises a sense or an antisense sequence.

The invention also includes an isolated oligonucleotide including a sequence selected from the group consisting of 5'-GCCATGTTGGATTCTCTAGTGTCG-3 SEQ ID NO:11, 5'-CCGAATTCTCAAAGCTTTTCTTCCACG-3' SEQ ID NO:12, 5'-CGGAATTCACAGAAAAACACAGTGAGGAT-3' SEQ ID NO:13, 5'-GCCATGTTGGATTCTCTAGTGTCG-3 SEQ ID NO:14, 5'-CCGAATTCTCAAAGCTTTTCTTCCACG-3' SEQ ID NO:15 and 5'-CGGAATTCACAGAAAAACACAGTGAGGAT-3' SEQ ID NO:16 or 5 to 15 nucleotides of one of these oligonucleotides. The invention also includes an isolated oligonucleotide having a sequence homologous to one of these oligonucleotides.

The invention also includes an expression vector including a nucleic acid molecule of the invention. The expression vector preferably comprises a promoter selected from the group consisting of a super promoter, a 35S promoter of cauliflower mosaic virus, a drought-inducible promoter, an ABA-inducible promoter, a heat shock-inducible promoter, a salt-inducible promoter, a copper-inducible promoter, a steroid-inducible promoter and a tissue-specific promoter.

The invention also includes a polypeptide produced from a nucleic acid molecule or expression vector of the invention. The invention also includes a polypeptide for extrusion of monovalent cations ions from the cytosol of a cell to provide the cell with salt tolerance. The invention also includes a polypeptide including the amino acid sequence in FIGS. 1(a)–(e) or a polypeptide homologous to one of these sequences. The invention also includes a polypeptide including a sequence having greater than 28% homology to one of these polypeptides. The polypeptide is preferably a $Na^+/H^+$ exchanger polypeptide isolated from *Arabidopsis thaliana*. The invention also includes a peptide including at least 5 amino acids or 41 to 75 amino acids of the polypeptide of the invention. The invention also includes nucleic acid molecules these polypeptides.

The invention includes a polypeptide for extrusion of monovalent cations ions from the cytosol of a cell to provide the cell with salt tolerance, including, but not necessarily having, an amiloride binding domain.

Another aspect of the invention relates to a monoclonal or polyclonal antibody directed against a polypeptide of the invention.

Another variation includes a transformed microorganism including an isolated nucleic acid molecule of the invention. The transformed microorganism preferably includes an expression vector of the invention.

A plant cell, yeast cell transformed or transfected with a nucleic acid molecule or a plant, plant part or seed, generated from the plant cell. The plant, plant part, seed or plant cell is preferably from a species selected from the group consisting of potato, tomato, *brassica*, cotton, sunflower, strawberries, spinach, lettuce, rice, soybean, corn, wheat, rye, barley, *atriplex*, sorgum, alfalfa, salicornia and other plants in Table 5. The invention also includes a method for producing a peptide, by culturing the plant, plant part, seed or plant cell and recovering the expressed peptide from the culture.

The invention includes a nucleic acid molecule that encodes all or part of a polypeptide capable of extruding monovalent cations from the cytosol of a cell to provide the cell with salt tolerance, wherein the sequence hybridizes to the nucleic acid molecule of all or part of SEQ ID NO:1 or SEQ ID NO:3, SEQ ID NO:17, SEQ ID NO:19, FIG. 5(b) or a nucleic acid molecule including nucleotides 1–1487 of FIG. 5(b) under low, medium and high stringency conditions. The high stringency conditions preferably comprise a wash stringency of selected from the group of hybridization and wash stringencies in Table 4.

The invention includes an isolated nucleic acid molecule encoding a polypeptide capable of extruding monovalent cations from the cytosol of a cell to provide the cell with salt tolerance, including the nucleic acid molecule in FIG. 5(b). The invention also includes an isolated nucleic acid molecule encoding a polypeptide capable of extruding monovalent cations from the cytosol of a cell to provide the cell with salt tolerance, including nucleotides 1 to 1487 of the nucleic acid molecule in FIG. 5(b).

Another aspect of the invention relates to an isolated nucleic acid molecule including about 1640 (or preferably about 1600 or 1700) nucleic acids encoding a polypeptide capable of extruding monovalent cations from the cytosol of a cell to provide the cell with salt tolerance, the nucleic acid molecule including nucleotides 1 to 1487 (or preferably about nucleotides 1 to 1470, 1480, 1490 or 1500) of the nucleic acid molecule in FIG. 5(b). The molecule is preferably DNA or RNA. The cell is preferably selected from the group consisting of a plant cell, a yeast cell and a bacterial cell. The molecule preferably encodes a $Na^+/H^+$ exchanger polypeptide. The nucleic acid molecule is preferably isolated from *Arabidopsis thaliana*.

The invention also includes the nucleic acid molecule in FIG. 5(b) or a nucleic acid molecule having greater than 17% homology to the sequence in 5(b). The invention includes polypeptides produced from this one of these nucleic acid molecules. The invention also relates to a polypeptide including the amino acid sequence in FIG. 5(b) or amino acids 1 to 496 of FIG. 5(b). (note: polypeptide including 1 to 496 is preferably about 530, 540 or 550 amino acids, most preferably about 538 amino acids) or a homologous polypeptide, preferably having greater than 28% homology. The polypeptide is preferably a $Na^+/H^+$ exchanger polypeptide, isolated from *Arabidopsis thaliana*. The invention also includes a DNA molecule encoding one of these polypeptides.

The invention includes an isolated nucleic acid molecule encoding a polypeptide capable of extruding monovalent cations from the cytosol of a cell to provide the cell with salt tolerance, including at least one of the nucleic acid molecules in FIG. 1(c). The molecule is preferably DNA or RNA. The cell is preferably selected from the group consisting of a plant cell, a yeast cell and a bacterial cell and encodes a $Na^+/H^+$ exchanger polypeptide isolated from *Arabidopsis thaliana*.

The invention includes an isolated nucleic acid molecule, including the nucleic acid molecule in FIG. 1(c)(i) or 1(c)(ii) or a polypeptide produced from a nucleic acid molecule of the invention. The invention also includes a polypeptide including the amino acid sequence in FIG. 1(c)(i) or 1(c)(ii) or homologous to this polypeptide, preferably having greater than 28% homology. The polypeptide is preferably a $Na^+/H^+$ exchanger polypeptide, isolated from *Arabidopsis thaliana*. The invention includes a DNA molecule encoding one of these polypeptides.

It will be clear to one skilled in the art that the sequences in FIGS. 1(c) and 5 are useful in isolating other salt tolerant nucleic acid molecules (for example probes may be made from the sequences in FIGS. 1(c) and 5), preparing transgenic plants and performing many of the other methods of the invention that are described with respect to sequences in FIGS. 1(a), (b), (d) and (e). Variants and modifications of FIG. 1(c) and FIG. 5 sequences are also included within the invention as are methods using varied or modified sequences (the same preferred percentages of identity and sequence described with respect to FIGS. 1(a), (b), (d) and (e) also apply to FIGS. 1(c) and 5). Nucleic acid molecules including a portion of the nucleic acid molecule in FIG. 5 preferably include about nucleotides 1–1487 (or a partial sequence thereof, preferably starting from the coding region, which will be apparent to a skilled person, at about nucleotide 286). The nucleotide sequence including all or part of sequence in FIG. 1(c) or FIG. (5) will be preferably about 1614 nucleotides in length (or the 1614 nucleotides minus part or all of the 5' untranslated region nucleotides). The nucleic acid molecules are most preferably 1600 to 1620 nucleotides in length. Polypeptides including a portion of the nucleic acid molecule in FIG. 5 preferably include about amino acids 1 to 496 (or a partial sequence thereof in FIG. 5. The sequences encoding all or part of the polypeptide in FIG. 5 or encoding a polypeptide corresponding to either of the nucleic acid molecule sequences in FIG. 1(c) are preferably about 538 amino acids in length and preferably about 60 kda in length. Preferred polypeptides are about 530–550 amino acids in length.

BRIEF DESCRIPTION OF THE DRAWINGS

The patent or application on file contains at least one drawing executed in color. Copies of this patent or patent apllication publication with color drawing(s) will be provided by the Office upon request and payment of the necessary fee.

Preferred embodiments of the invention are described in relation to the drawings in which:

FIG. 1. (a) Shows the nucleic acid molecule that is SEQ ID NO:1 and the polypeptide that is SEQ ID NO:2.

Figure 3:
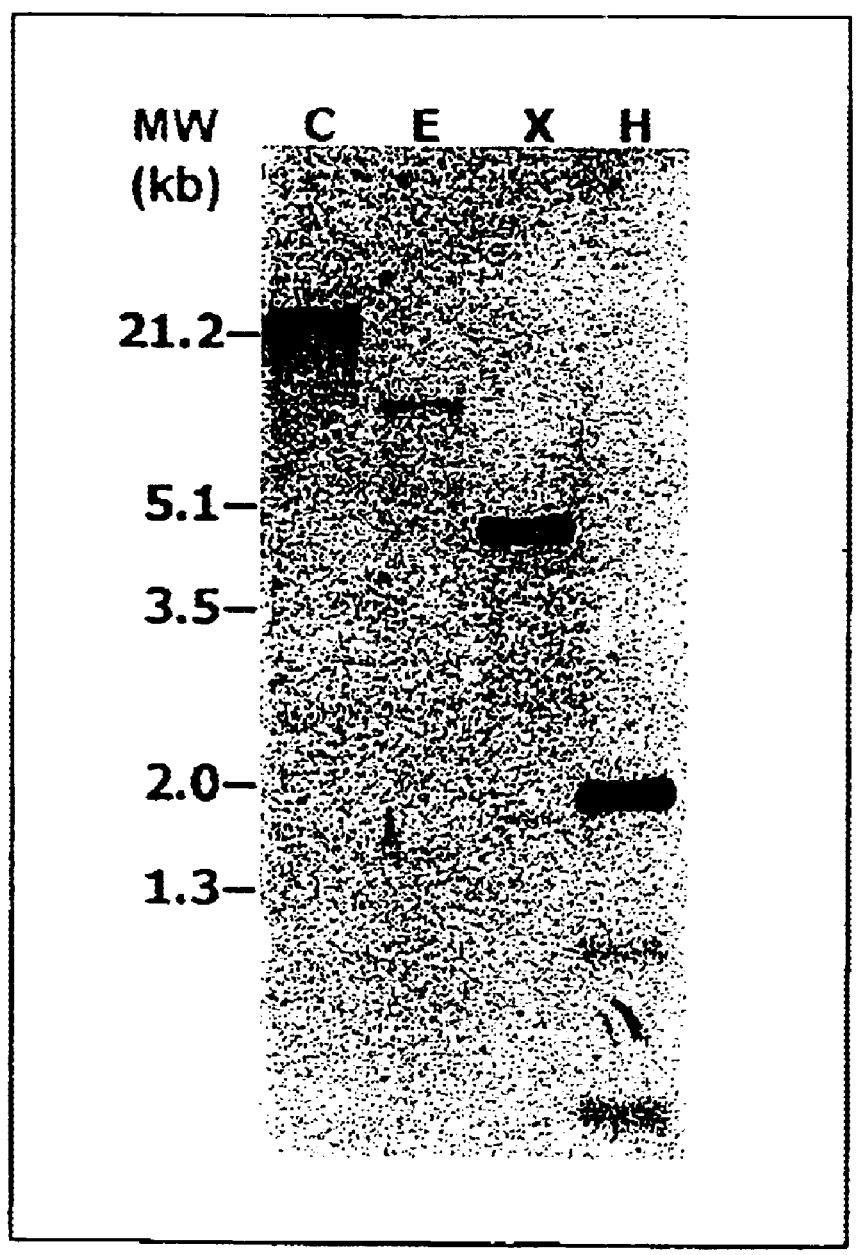

In a preferred embodiment, the figure shows isolated AtNHX1 cDNA encoding a $Na^+/H^+$ exchanger from *Arabidopsis thaliana* showing cDNA sequence and the corresponding amino acid sequence for AtNHX1. Twelve transmembrane domains are present, a conserved amiloride-binding domain is present, and a relatively hydrophilic C-terminal region is also present. The predicted open reading frame begins at nucleotide 286. The amino acids are centred below the corresponding codon and are numbered on the left;

(b) Shows the nucleic acid molecule that is SEQ ID NO:3 and the polypeptide that is SEQ ID NO:4.

In a preferred embodiment, the figure shows isolated AtNHX2 cDNA encoding a $Na^+/H^+$ exchanger from *Arabidopsis thaliana* showing cDNA sequence and the corresponding predicted amino acid sequence for AtNHX2. The predicted open reading frame begins at nucleotide 61. The amino acids are centred below the corresponding codon and are numbered on the left;

(c) (i) Shows the nucleic acid molecule that is SEQ ID NO:5 and the polypeptide that is SEQ ID NO:6. (ii) Shows the nucleic acid molecule that is SEQ ID NO:7 and the polypeptide that is SEQ ID NO:8.

In a preferred embodiment, the figure shows AtNHX3 partial cDNA sequences. The amino acids are centred below the corresponding codon and are numbered on the left (i) 5' sequence of the partial AtNHX3 cDNA and amino acid sequence; (ii) In a preferred embodiment, the figure shows 3' sequence of the partial AtNHX3 cDNA and amino sequence;

(d) Shows the nucleic acid molecule that is SEQ ID NO:17 and the polypeptide that is SEQ ID NO:18.

In a preferred embodiment, the figure shows isolated AtNHX3 cDNA encoding a $Na^+/H^+$ exchanger from *Arabidopsis thaliana* showing cDNA sequence and the corresponding predicted amino acid sequence for AtNHX3. The predicted open reading frame begins at nucleotide 67. The amino acids are centred below the corresponding codon and are numbered on the left. (e) Isolated AtNHX4 cDNA encoding a $Na^+/H^+$ exchanger from *Arabidopsis thaliana* showing cDNA sequence SEQ ID NO:19 and the corresponding predicted amino acid sequence SEQ ID NO:20 for AtNHX4. The predicted open reading frame begins at nucleotide 55. The amino acids are centred below the corresponding codon and are numbered on the left.

(e) Shows the nucleic acid molecule that is SEQ ID NO:19 and the polypeptide that is SEQ ID NO:20.

In a preferred embodiment, the figure shows isolated AtNHX4 cDNA encoding a $Na^+/H^+$ exchanger from *Arabidopsis thaliana*.

Figure 2A-2:
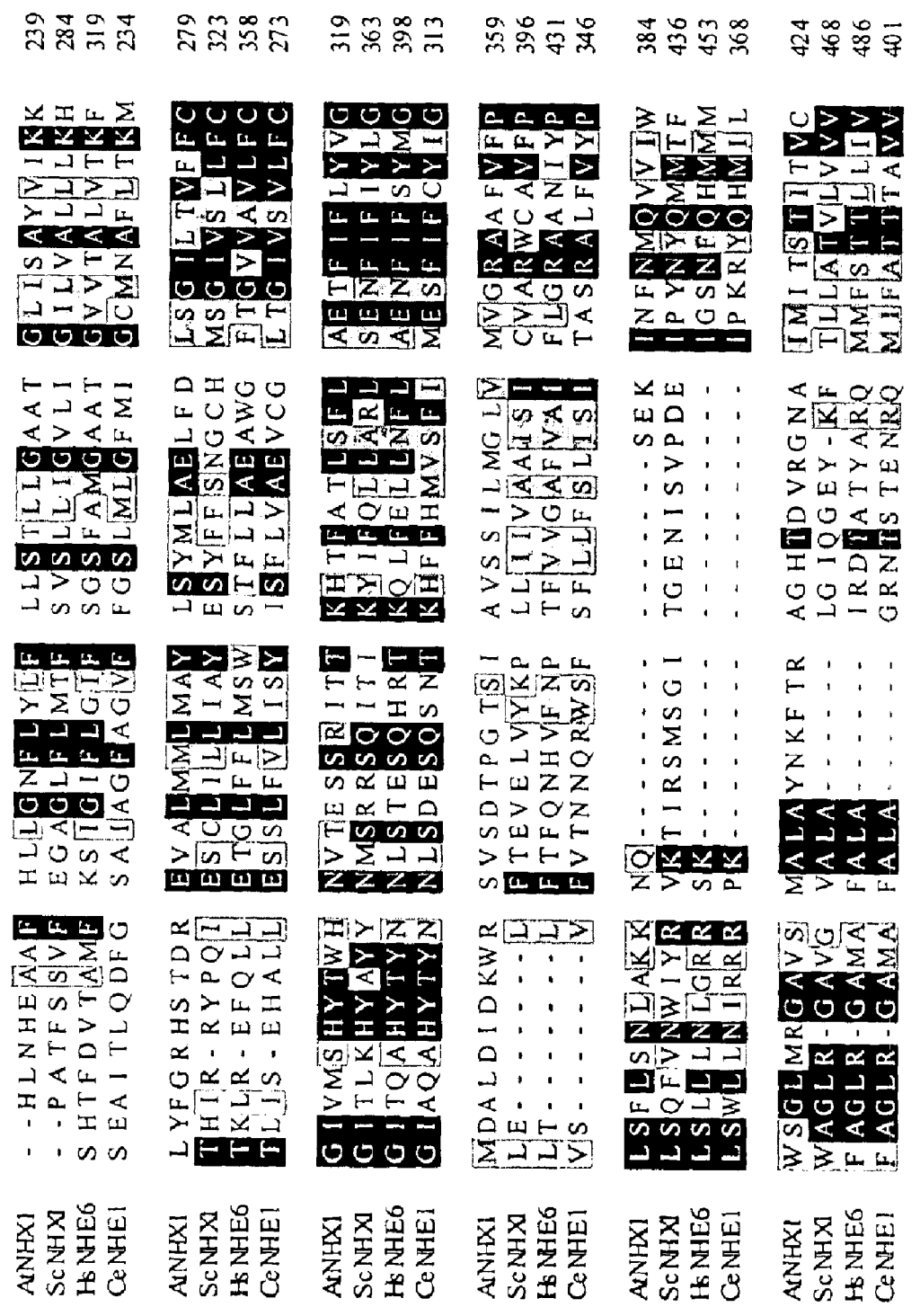

FIG. 2. (a) Alignment of the predicted amino acid sequences of *Arabidopsis* AtNHX1 SEQ ID NO:2, from *Arabidopsis thaliana* with other $Na^+/H^+$ exchangers from other organisms. Sequences were aligned using the Clustal W program (19) using default parameters (fixed gap penalty=10, floating gap penalty=10, protein weight matrix BLOSUM62). Sequences and GenBank accession numbers are: ScNHX1, late endosomal $Na^+/H^+$ exchanger *S. cerevisiae*, SEQ ID NO:29 (GenBank accession #927695); CeNHE1, *C. elegans*, SEQ ID NO:31 (GenBank accession # 3877723; HsNHE6, *Homo sapiens* mitochondrial $Na^+/H^+$ exchanger, SEQ ID NO:30 (GenBank accession # 2944237); (b) Alignment of the predicted amino acid sequences of AtNHX1 SEQ ID NO:2, AtNHX2 SEQ ID NO:4 and AtNHX3 SEQ ID NO:18 cDNAs from *Arabidopsis thaliana*. Sequences were aligned using the Clustal W program using default parameters (fixed gap penalty=10, floating gap penalty=10, protein weight matrix BLOSUM62); (c) Alignment of the predicted amino acid sequences of AtNHX3 SEQ ID NO:18 and AtNHX4 SEQ ID NO:20 cDNAs from *Arabidopsis thaliana*. Sequences were aligned using the Clustal W program using default parameters (fixed gap penalty=10, floating gap penalty=10, protein weight matrix BLOSUM62).

FIG. 3. A Southern blot of *Arabidopsis* genomic DNA. Genomic DNA (10 μg per lane) was digested with various restriction enzymes, separated on a 1.0% agarose gel, transferred onto a GeneScreen Plus membrane (Amersham), and hybridized to a radiolabelled AtNHX1 cDNA as described in Materials and Methods. Restriction enzymes used were; C, ClaI; E, ECoRI; X, XbaI; H, HindIII.

Figure 4:
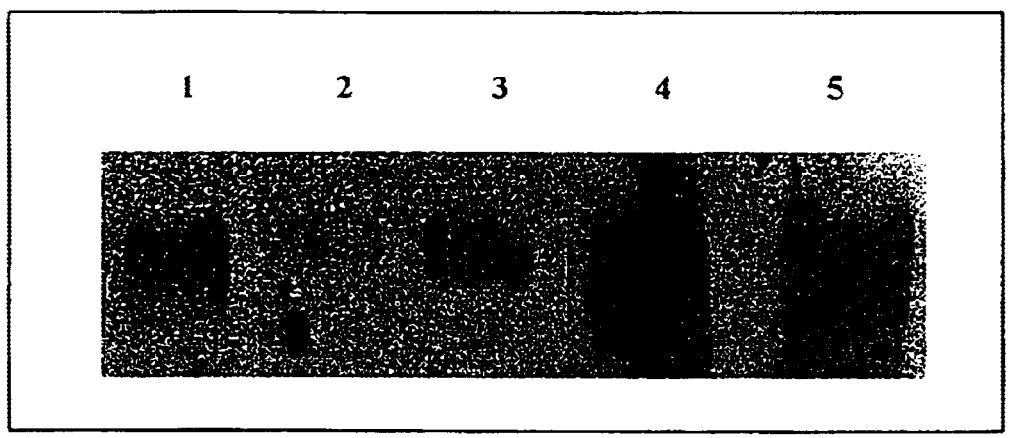

FIG. 4. RNA blot of AtNHX1 expression in different tissues. Total RNA (40 μg) was separated on a 1.0% agarose gel, transferred to a GeneScreen Plus membrane (Amersham) and hybridized to a radiolabelled AtNHX1 cDNA probe as described in Materials and Methods. Tissues in each lane were as follows: 1, mature leaf; 2, flower (including sepals); 3, infloresence stem; 4, seedling shoot; 5, seedling root.

FIGS. 5. (a) and (b) show the nucleic acid molecule that is SEQ ID NO:9 and the polypeptide that is SEQ ID NO:10.

In a preferred embodiment, (a) and (b) show modified *arabidopsis* sodium/proton antiporter cDNA and polypeptide sequence.

Figure 6:
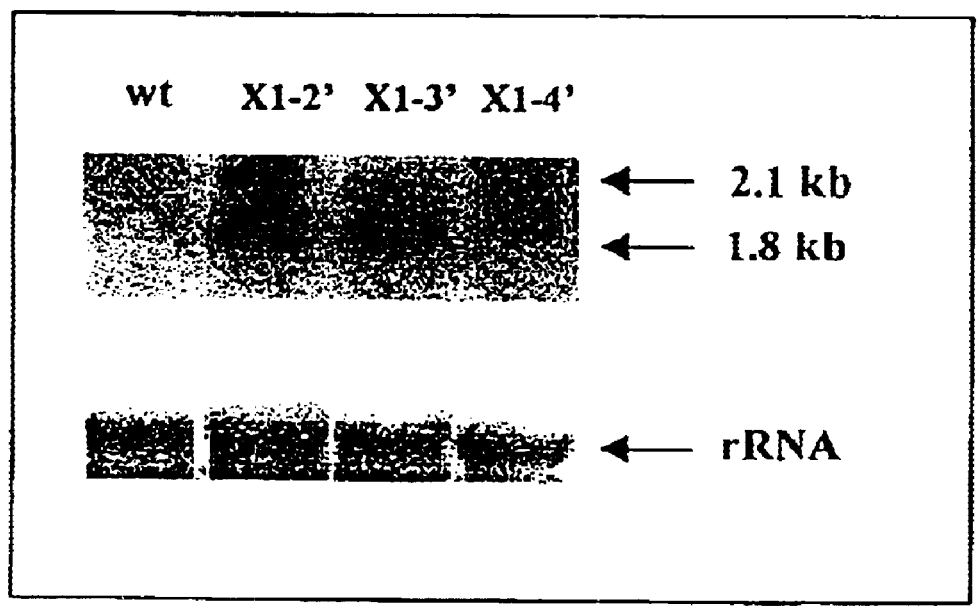
Figure 7A:
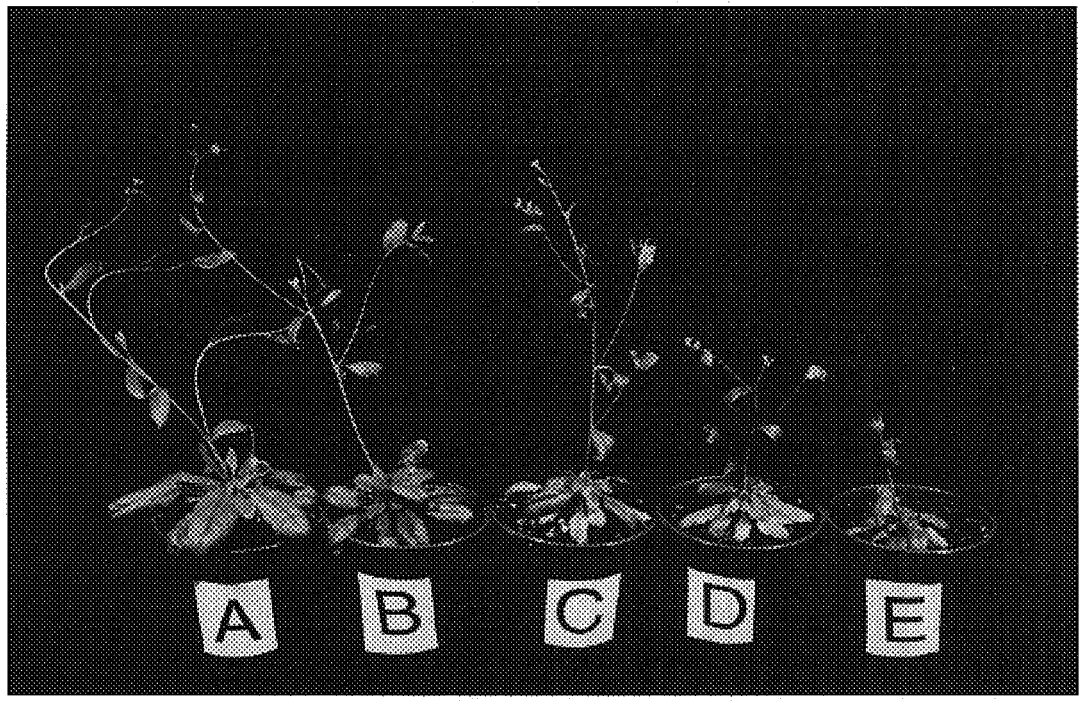
Figure 7B:
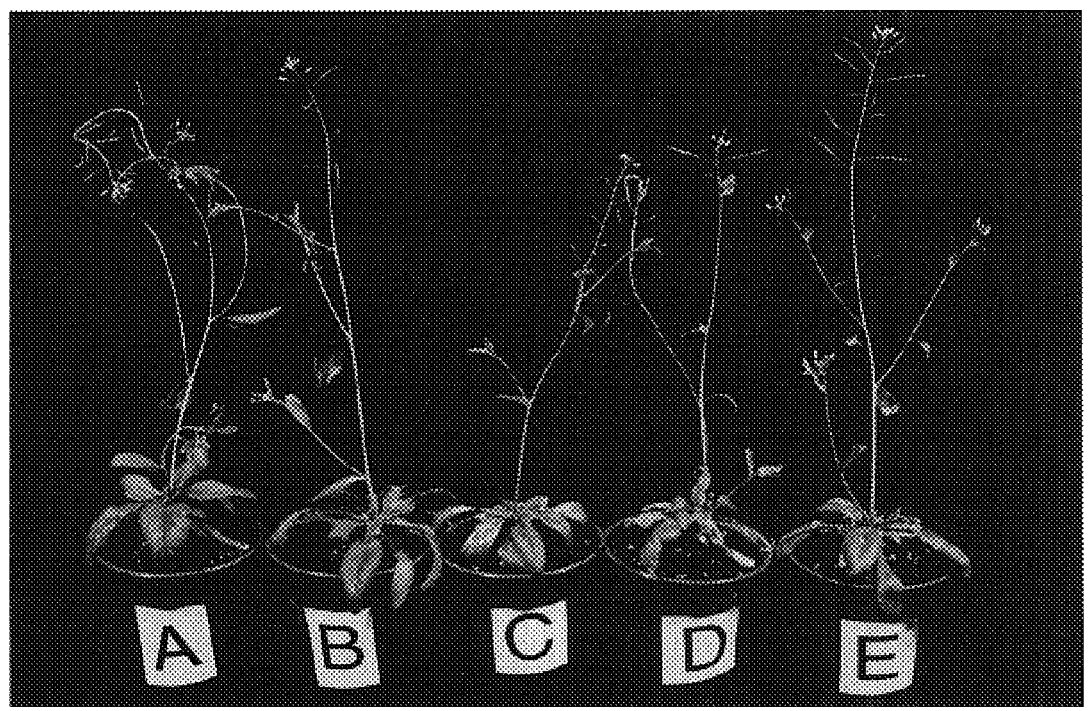
Figure 7C:
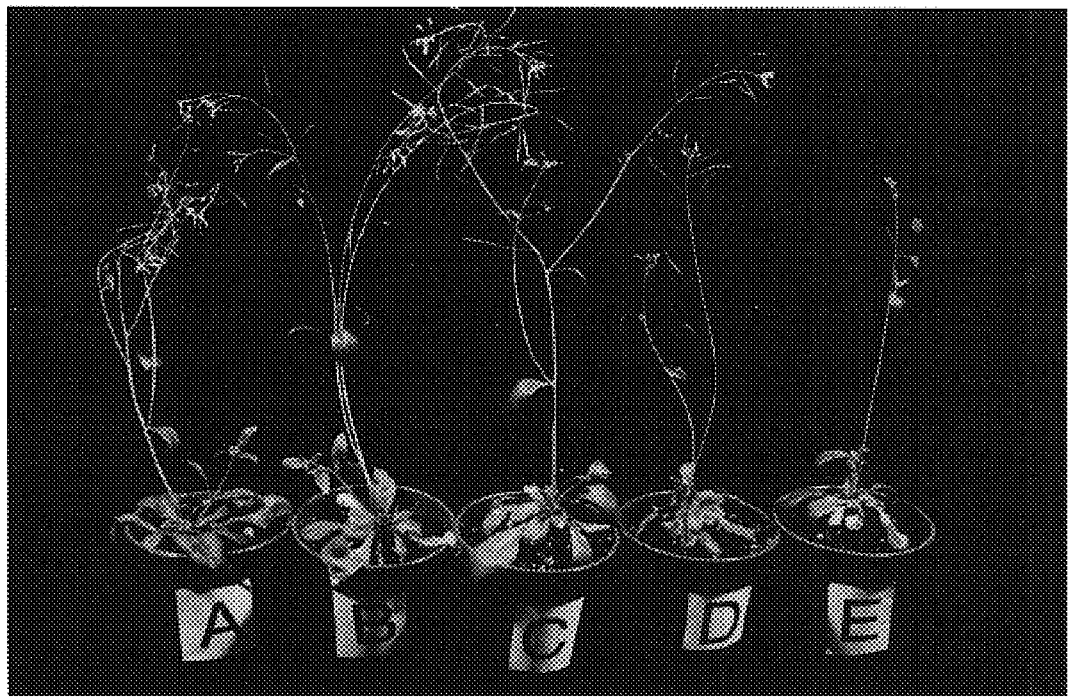
Figure 7D:
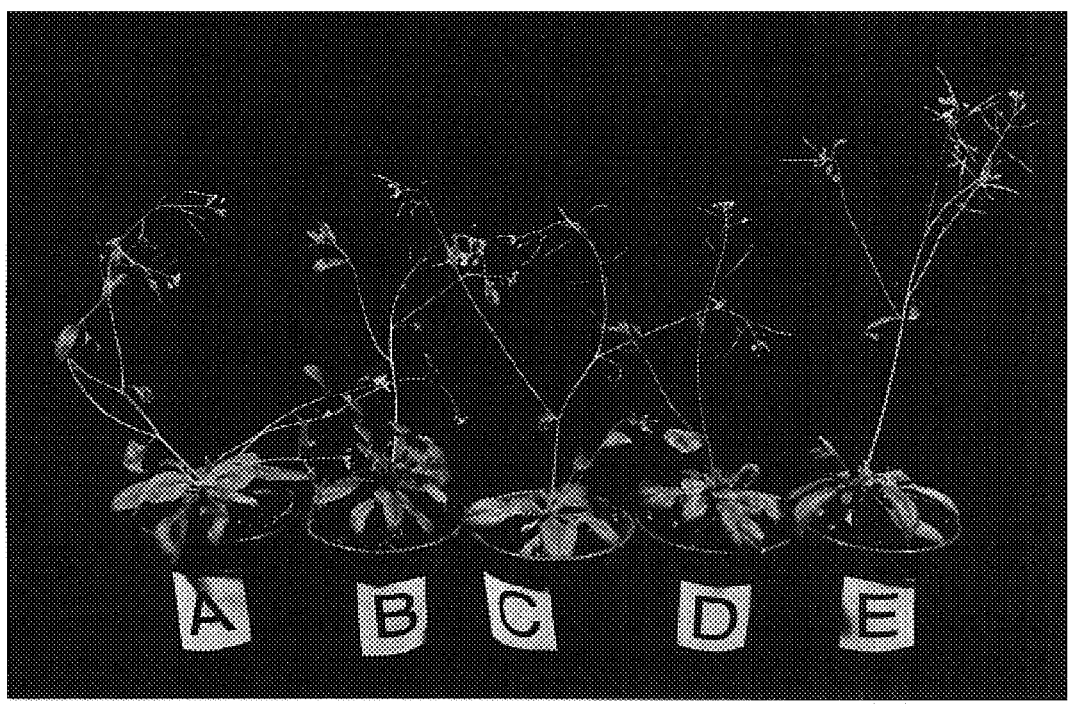
Figure 7E:
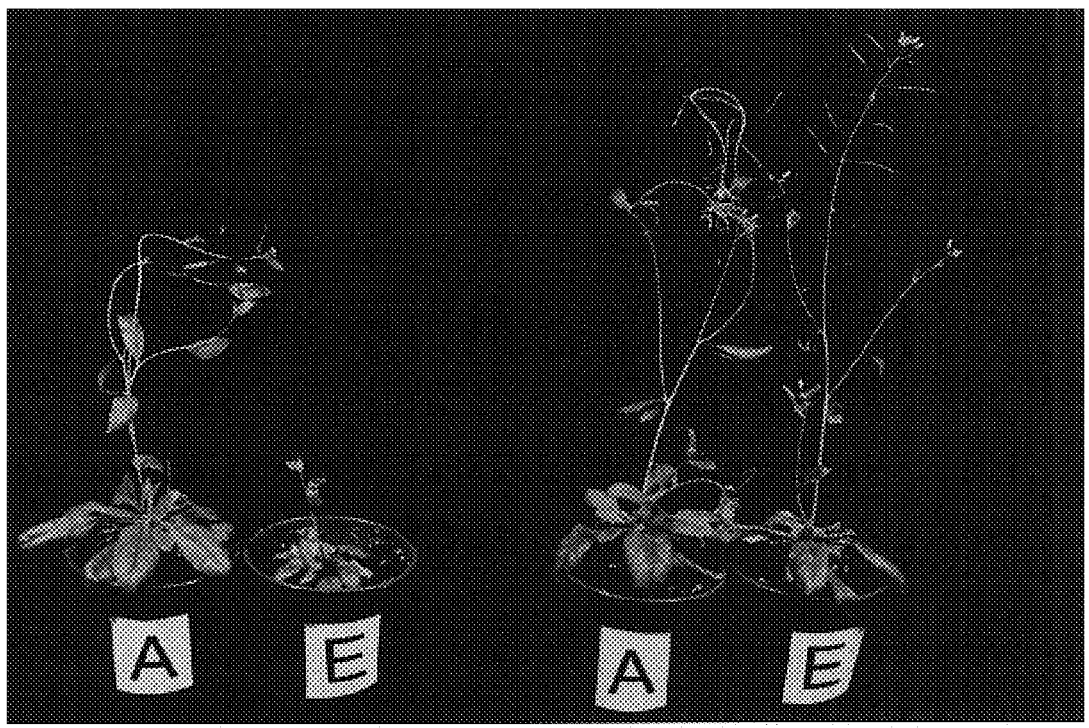
Figure 7F:
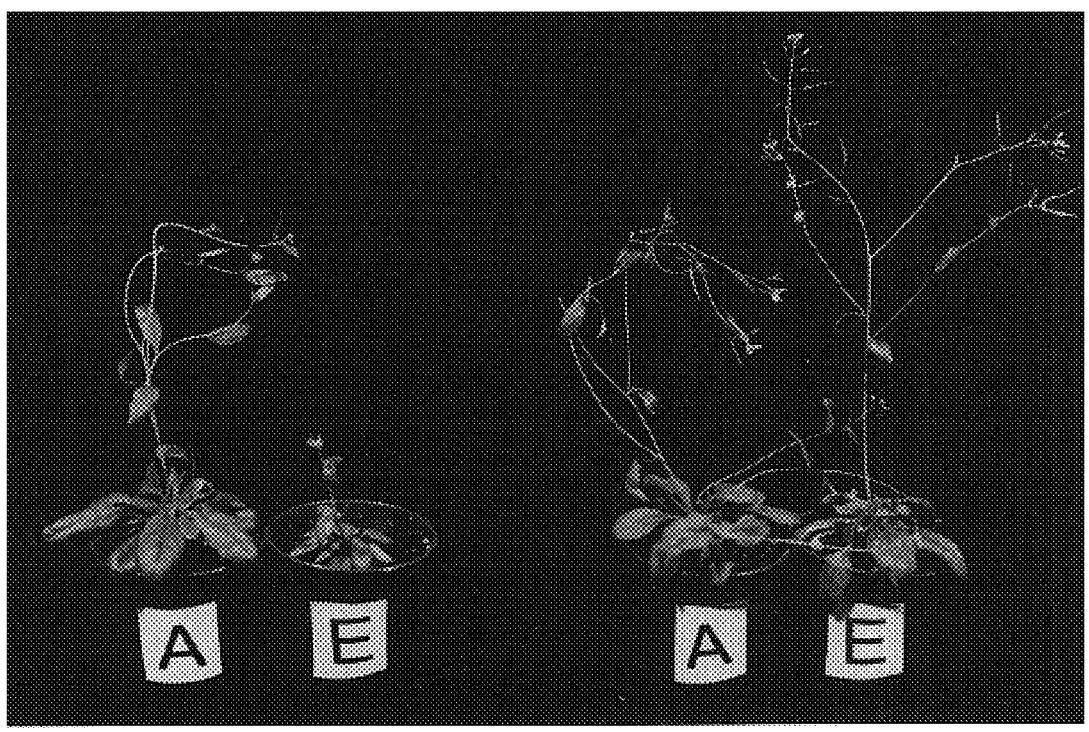
Figure 7G:

FIG. 6. RNA blot comparing transcript levels in *Arabidopsis thaliana* leaf tissue from wild type and different transgenic lines overexpressing AtNHX1. RNA was extracted from 4 week-old plants. Total RNA (30 μg per lane) was separated on a 1.0% agarose gel, transferred to a GeneScreen Plus membrane (Amersham) and hybridized to a radiolabelled AtNHX1 cDNA probe as described in Materials and Methods. An endogenous 2.1 kb transcript was detected in the transgenic lines as well as in wild type. An overexpressed. 1.8 kb transcript was only seen in the transgenic lines. The 1.8 kb transcript corresponds to the open reading frame coding for AtNHX1, lacking the 5'- and 3'-untranslated regions present in the original cDNA (2.1 kb). Ribosomal RNA (rRNA) was used to confirm equal loading of the gels, as seen by methylene-blue staining of the blot.

wt: wild-type; X1-2', X1-3' and X1-4': independent transgenic lines.

FIG. 7. Twenty 3-week old kanamycin-resistant *Arabidopsis thaliana* plants for each of the 3 independent transgenic lines (X1.2', X1.3' and X1.4') transformed with AtNHX1, as well as 20 wild-type plants of the same age were used for assessment of salt tolerance. Plants were watered with 25 ml of ⅛ strength MS salts (control solution) supplemented with different concentrations of NaCl. The following schedule was used for a total of 16 days, at which point pictures of representative plants were taken: a) wild-type: A=0 mM NaCl, B=50 mM NaCl, C=100 mM NaCl, D=150 mM NaCl, E=200 mM NaCl; b) X1.2' transgenic line: A=0 mM NaCl, B=50 mM NaCl, C=100 mM NaCl, D=150 mM NaCl, E=200 mM NaCl; c) X1.3' transgenic line; d) X1.4' transgenic line: A=0 mM NaCl, B=50 mM NaCl, C=100 mM NaCl, D=150 mM NaCl, E=200 mM NaCl; e) wild type: A=0 mM NaCl, E=200 mM NaCl vs. transgenic strain 2': A=0 mM NaCl, E=200 mM NaCl; f) wild type: A=0 mM NaCl, E=200 mM NaCl vs. transgenic strain 4': A=0 mM NaCl, E=200 mM NaCl; g) wild type: A=0 mM NaCl, E=200 mM NaCl vs. transgenic strain 2': A=0 mM NaCl, E=200 mM NaCl and transgenic strain 4': A=0 mM NaCl, E=200 mM NaCl.

Treatments:
A) watered with a control solution (⅛ MS strength solution, 0 mM NaCl) eight times (once every two days)
B) watered with a control solution supplemented with 50 mM NaCl eight times (once every two days)
C) watered twice (once every two days) with a control solution supplemented with 50 mM NaCl, then with a control solution supplemented with 100 mM NaCl six times (once every two days).
D) watered twice (once every two days) with a control solution supplemented with 50 mM NaCl, then with a control solution supplemented with 100 mM NaCl twice (once every two days) followed by a control solution supplemented with 150 mM NaCl four times (once every two days).
E) watered twice (once every two days) with a control solution supplemented with 50 mM NaCl, then with a control solution supplemented with 100 mM NaCl twice (once every two days) followed by a control solution supplemented with 150 mM NaCl twice (once every two days) and a control solution supplemented with 200 mM NaCl twice (once every two days).

FIG. 8. (a) shows SEQ ID NO:21 (b) shows SEQ ID NO:22 (c) shows SEQ ID NO:23 (d) shows SEQ ID NO:24 (e) shows SEQ ID NO:25 (f) shows SEQ ID NO:26 (g) shows SEQ ID NO:27 (h) shows SEQ ID NO:28.

In preferred embodiments, (a)–(h) show sequences from Table 2: (a) GenBank Accession No. 3850064 569 a.a.; (b) Genbank Accession No. 927695 633 a.a.; (c) GenBank Accession No. C91832 378 bp mRNA EST; (d) GenBank Accession No. C91861 268 bp mRNA EST; (e) GenBank Accession No. AU032544 380 bp mRNA EST; (f) GenBank Accession No. AA660573 596 bp mRNA EST; (g) GenBank Accession No. L44032 522 bp mRNA STS; (h) GenBank Accession No. T75860 (EST) 330 bp mRNA EST.

DETAILED DESCRIPTION OF THE INVENTION

Salt Tolerance Nucleic Acid Molecules and Polypeptides

The invention relates to nucleic acid molecules and polypeptides which increase salt tolerance in cells and plants. PNHX polypeptides are plant $Na^+/H^+$ transporter polypeptides that are capable of increasing and enhancing salt tolerance in a cell, preferably a plant cell. These transporters (also referred to as exchangers, antiports or antiporters) extrude monovalent cations (preferably potassium ions or lithium ions, most preferably sodium ions) out of the cytosol. The cations are preferably extruded into the vacuoles or extracellular space. The affinity for particular ions varies between transporters. The listed preferences refer to the cations that are most likely to be abundant in the cytosol and therefore most likely to be extruded. It is not necessarily a reflection of transporter affinity for particular cations. The PNHX nucleic acid molecules which encode PNHX polypeptides are particularly useful in producing transgenic plants which have increased salt tolerance compared to a wild type plant.

It will also be apparent that there are polypeptide and nucleic acid molecules from other organisms, such as yeast, microorganisms, fish, birds or mammals, that are similar to PNHX polypeptides and nucleic acid molecules. The entire group of $Na^+/H^+$ transporter polypeptides and nucleic acid molecules that are capable of increasing salt tolerance in a cell (including PNHX and AtNHX polypeptides and nucleic acid molecules) are collectively referred to as ("TNHX polypeptides" and "TNHX nucleic acid molecules"). TNHX polypeptides are $Na^+/H^+$ transporters that are capable of increasing salt tolerance in a cell, preferably a plant cell, because they extrude monovalent cations (preferably potassium ions or lithium ions, most preferably sodium ions) out of the cytosol.

The role of TNHX and PNHX nucleic acid molecules and polypeptides in maintaining salt tolerance was not shown before this invention. The ability of these compounds to increase salt tolerance of transgenic host cells (particularly plant cells) and transgenic plants compared to wild type cells and plants was unknown.

PNHX and TNHX polypeptides need not necessarily have the primary function of providing salt tolerance. All nucleotides and polypeptides which are suitable for use in the methods of the invention, such as the preparation of transgenic host cells or transgenic plants, are included within the scope of the invention. Genomic clones or cDNA clones are preferred for preparation of transgenic cells and plants.

In a preferred embodiment, the invention relates to cDNAs encoding $Na^+/H^+$ exchangers from *Arabidopsis thaliana*. The cDNA sequences and the corresponding amino acid sequences for AtNHX1, AtNHX2, AtNHX3 and AtNHX4 are presented in FIG. 1. AtNHX1 and AtNHX2 are homologs that are physically located at different places in the genome. The invention also includes splice variants of the nucleic acid molecules as well as polypeptides produced from the molecules. For example, AtNHX3 and AtNHX4 are homologs of AtNHX1 and AtNHX2. AtNHX3 and AtNHX4 are identical for a long sequence beginning at the N-terminus. This indicates that the difference in sequence at the C-terminus is due to alternative splicing of a nucleic acid molecule (also known as splicing variants). This allows a single nucleic acid molecule to produce varying polypeptides.

Characterization of Salt Tolerance Nucleic Acid Molecules and Polypeptides

The longest open reading frame of 1614 base pairs in AtNHX1 encodes a polypeptide of 538 amino acids with a predicted molecular weight ("MW") of about 60 Kda. A comparison of this full length cDNA with the *Arabidopsis* genome sequence (ATM021B04.4) revealed the presence of 13 introns and 14 exons. This polypeptide encoded by the open reading frame was about 19% larger than the sequence predicted by the *Arabidopsis* genomic sequence (A_TM021 B04.4). This sequence encodes the full length exchanger given that the cDNA region immediately upstream of the start codon contains predicted stop codons in all three reading frames. In addition, a transcript of approximately 2 kb, which corresponds roughly in size to the predicted mRNA for AtNHX1, was observed on RNA blots. Based on the amino acid sequence of AtNHX1, 12 transmembrane domains are predicted, a conserved amiloride-binding domain is present, and a relatively hydrophilic C-terminal region is also predicted. AtNHX1 shows some similarity at the amino acid level to $Na^+/H^+$ exchangers isolated from a variety of organisms ranging from yeast (about 27% identity) to humans (about 20%). A second salt tolerance cDNA and polypeptide, AtNHX2, was obtained from *Arabidopsis thaliana* (FIG. 1(b)). We characterized a third salt tolerance nucleic acid molecule, AtNHX3, by obtaining 5' and 3' cDNA and N-terminal and C-terminal sequences from *Arabidopsis thaliana* (FIG. 1(c)). In one variation, the invention includes DNA sequences (and the corresponding polypeptide) including at least one of the sequences shown in FIG. 1(c) in a nucleic acid molecule of preferably about: less than 1000 base pairs, less than 1250 base pairs, less than 1500 base pairs, less than 1750 base pairs, less than 2000 base pairs, less than 2250 base pairs, less than 2500 base pairs, less than 2750 base pairs or less than 3000 base pairs. We also identified the full AtNHX3 sequence (FIG. 1(d)). A fourth sequence, AtNHX4, was also identified (FIG. 1(e)).

The coding regions of the nucleic acid molecules are as follows:

TABLE 1

| Nucleic Acid Molecule | Start Nucleotide | End Nucleotide |
| --- | --- | --- |
| AtNHX1 | 286 | 1902 |
| AtNHX2 | 61 | 1707 |
| AtNHX3 | 67 | 1024 |
| AtNHX4 | 55 | 813 |

It will be apparent that these may be varied, for example, by shortening the 5' untranslated region or shortening the nucleic acid molecule so that the end nucleotide is in a different position.

The discussion of the nucleic acid molecules, sequence identity, hybridization and other aspects of nucleic acid molecules included within the scope of the invention is intended to be applicable to either the entire nucleic acid molecules in FIGS. 1(a), (b), (d) and (e) and the coding regions of these molecules, shown in Table 1. One may use the entire molecule in FIG. 1 or only the coding region. Other possible modifications to the sequence will also be apparent.

Southern Blot Analysis (FIG. 3) suggests that AtNHX1 is likely present as a single copy gene in *Arabidopsis*. A Northern blot (FIG. 4) showed that AtNHX polypeptide (particularly AtNHX1) was expressed in all tissues examined (root, shoot (shoot includes leaves and stems), flower, inflorescence stem).

Function of Salt Tolerance Nucleic Acid Molecules

The polypeptides of the invention allow the extrusion of monovalent cations (preferably potassium ions or lithium ions, most preferably sodium ions) from the cytosol, which in this application preferably refers to the transport and accumulation of sodium ions into the vacuoles or into the extracellular space (outside of the cell), thus providing the most important trait for salt tolerance in plants. Antiport polypeptides from organisms other than plants have shown different specificity for monovalent ions (e.g. D. G. Warnock, A. S. Pollock, "Sodium Proton Exchange in Epithelial Cells", pages 77–90, in S. Grinstein ed. *Sodium Proton Exchange*, (1987, CRC Press, USA).) TNHX and PNHX transporters will also show different specificity between transporters. The nucleic acid molecules of the invention allow the engineering of salt tolerant plants by transformation of crops with this nucleic acid molecule under the control of constitutively active promoters or under the control of conditionally-inducible promoters. The resulting expression or overexpression of these nucleic acid molecules confers increased salt tolerance in plants grown in soil, solid, semi-solid medium or hydroponically.

The PNHX Nucleic Acid Molecule and Polypeptide is Conserved in Plants

Sequence Identity

This is the first isolation of a nucleic acid molecule encoding a $Na^+/H^+$ exchanger from plant species. It is widely known amongst those skilled in the art that *Arabidopsis thaliana* is a model plant for many plant species. Nucleic acid sequences having sequence identity to the AtNHX sequences are found in other plants, in particular halophytes such as *Beta Vulgaris* and *Atriplex* (see Examples 2 and 7). Sequences from *Arabidopsis thaliana* and other plants are collectively referred to as "PNHX" nucleic acid sequences and polypeptides. We isolate PNHX nucleic acid molecules from plants having nucleic acid molecules that are similar to those in *Arabidopsis thaliana*, such as beet, tomato, rice, cucumber, radish and other plants as in Table 5 and using techniques described in this application. The invention includes methods of isolating these nucleic acid molecules and polypeptides as well as methods of using these nucleic acid molecules and polypeptides according to the methods described in this application, for example those used with respect to AtNHX.

Table 2 below shows several sequences with sequence identity and sequence similarity to the AtNHX polypeptides. Where polypeptides are shown, a suitable corresponding DNA encoding the polypeptide will be apparent. These sequences code for polypeptides similar to portions of AtNHX polypeptides. The sequences in Table 2 are useful to make probes to identity full length sequences or fragments (from the listed species or other species). One skilled in the art would be able to design a probe based on a polypeptide or peptide fragment. The invention includes nucleic acid molecules of about: 10 to 50 nucleotides, 50 to 200 nucleotides, 200 to 500 nucleotides, 500 to 1000 nucleotides, 1000 to 1500 nucleotides, 1500 to 1700 nucleotides, 1700 to 2000 nucleotides, 2000 to 2500 nucleotides or at least 2500 nucleotides and which include all or part of the sequences (or corresponding nucleic acid molecule) in Table 2. The invention also includes peptides and polypeptides of about: 10 to 50 amino acids, 50 to 200 amino acids, 200 to 500 amino acids, 500 to 750 amino acids or at least 750 amino acids which encode all or part of the polypeptides in Table 2 (wherein the polypeptide is produced according to a reading frame aligned with an AtNHX polypeptide). Possible modifications to these sequences will also be apparent. The polypeptide and nucleic acid molecules are also useful in research experiments or in bioinformatics to locate other sequences. The nucleic acid molecules and polypeptides preferably provide $Na^+/H^+$ transporter activity and are capable of moving monovalent cations from the cytosol of the cell into vacuoles or the extracellular space (in this application, extracellular space refers to the space outside a cell in an organism or the space outside a cultured cell).

TABLE 2

| Organism | GenBank Accession No. |
|---|---|
| Yeast (*S. pombe*) (FIG. 8(a)) | 3850064 |
| Yeast (*Saccharomyces cervisae*) (FIG. 8(b)) | 927695 |
| Rice EST (FIG. 8(c)) | C 91832 |
| Rice EST (FIG. 8(d)) | C 91861 |
| Rice EST (FIG. 8(e)) | AV032544 |
| *Medicago Trunculata* EST (FIG. 8(f)) | AA660573 |
| *Hordeum Vulgare* STS (FIG. 8g)) | L 44032 |

As shown in Table 3 below, many nucleic acid molecules identified in *Arabidopsis thaliana* have striking DNA sequence similarity to nucleic acid molecules encoding the homologous polypeptide in other plant species. Using the techniques described in this application and others known in the art, it will be apparent that the nucleic acid molecule encoding the homologous $Na^+/H^+$ exchanger in other plant species including, but not limited to plants of agricultural and commercial interest, will have DNA sequence identity (homology) at least about >17%, >20%, >25%, >35% to a DNA sequence shown in FIG. 1 or 5 (or a partial sequence thereof). Some plants species may have DNA with a sequence identity (homology) at least about: >50%, >60%, >70%, >80% or >90% more preferably at least about >95%, >99% or >99.5%, to a DNA sequence in FIG. 1 or 5 (or a partial sequence thereof). The invention also includes modified nucleic acid molecules from plants other than *Arabidopsis thaliana* which have sequence identity at least about: >17%, >20%, >25%, >35%, >50%, >60%, >70%, >80% or >90% more preferably at least about >95%, >99% or >99.5%, to an AtNHX sequence in FIG. 1 or 5 (or a partial sequence thereof). Modified nucleic acid molecules are discussed below. Preferably about 1, 2, 3, 4, 5, 6 to 10, 10 to 25, 26 to 50 or 51 to 100, or 101 to 250 nucleotides or amino acids are modified. Sequence identity is most preferably calculated as the number of identical amino acid residues expressed as a percentage of the length of the shorter of the two sequences in a pairwise alignment. The pairwise alignment is constructed preferably using the Clustal W program preferably using the following, parameter settings: fixed gap penalty=10, floating gap penalty=10, protein weight matrix=BLOSUM62. For example, if a nucleotide sequence (called "Sequence A") has 90% identity to a portion of the nucleotide sequence in FIG. 1(a), then Sequence A will be identical to the referenced portion of the nucleotide sequence in FIG. 8, except that Sequence A may include up to 10 point mutations, such as substitutions with other nucleotides, per each 100 nucleotides of the referenced portion of the nucleotide sequence in FIG. 8. Polypeptides having sequence identity may be similarly identified.

The invention also includes nucleic acid molecules encoding polypeptides having sequence similarity taking into account conservative amino acid substitutions. Sequence similarity (and preferred percentages) are discussed below.

It will be apparent that nucleic acid molecule encoding the homologous $Na^+/H^+$ exchanger in other species (preferably plants) including, but not limited to plants of agricultural and commercial interest, will hybridize to all or part of a sequence in FIG. 1 or 5 (or a partial sequence thereof) under low, moderate (also called intermediate conditions) or high stringency conditions. Preferred hybridization conditions are described below.

The invention includes the nucleic acid molecules from other plants as well as methods of obtaining the nucleic acid molecules by, for example, screening a cDNA library or other DNA collection with a probe of the invention (such as a probe comprising at least about: 10 or preferably at least 15 or 30 nucleotides of AtNHX1, AtNHX2, AtNHX3 or AtNHX4 or a sequence in FIG. 5) and detecting the presence of a TNHX or PNHX nucleic acid molecule. Another method involves comparing the AtNHX sequences (eg in FIG. 1 or 5) to other sequences, for example using bioinformatics techniques such as database searches or alignment strategies, and detecting the presence of a TNHX or PNHX nucleic acid molecule or polypeptide. The invention includes the nucleic acid molecule and/or polypeptide obtained according to the methods of the invention. The invention also includes methods of using the nucleic acid molecules, for example to make probes, in research experiments or to transform host cells or make transgenic plants. These methods are as described below.

The polypeptides encoded by the homologous TNHX or PNHX nucleic acid molecules in other species will have amino acid sequence identity. The preferred percentage of sequence identity for sequences of the invention includes sequences having identity of at least about: 30% to AtNHX1, 31% to AtNHX2, 36% to AtNHX3, and 36% to AtNHX4. Sequence identity may be at least about: >20%, >25%, >28%, >30%, >35%, >40%, >50% to an amino acid sequence shown in FIG. 1 or 5 (or a partial sequence thereof). Some polypeptides may have a sequence identity of at least about: >60%, >70%, >80% or >90%, more preferably at least about: >95%, >99% or >99.5% to an amino acid sequence in FIG. 1 or 5 (or a partial sequence thereof). Identity is calculated according to methods known in the art. Sequence identity is most preferably assessed by the Clustal W program. The invention also includes modified polypeptides from plants which have sequence identity at least about: >20%, >25%, >28%, >30%, >35%, >40%, >50%, >60%, >70%, >80% or >90% more preferably at least about >95%, >99% or >99.5%, to an AtNHX sequence in FIG. 1 or 5 (or a partial sequence thereof). Modified polypeptides molecules are discussed below. Preferably about: 1, 2, 3, 4, 5, 6 to 10, 10 to 25, 26 to 50 or 51 to 100, or 101 to 250 nucleotides or amino acids are modified.

TABLE 3

| | Polypeptide | DNA |
|---|---|---|
| Plant Vacuolar $H^+$-PPiase (vacuolar pyrophosphatase) | | |
| *Arabidopsis* (Accession #282878) | 100% | 100% |
| Beet (Accession #485742) | 88.7% | 72.8% |
| Tobacco (Accession #1076627) | 89.9% | 68.4% |
| Rice (Accession #1747296) | 85% | 70.4% |
| Tonoplast Intrinsic Polypeptide (water channel) | | |
| *Arabidopsis* (Accession #X63551) | 100% | 100% |
| *Curcubita* (Cucumber) (Accession #D45078) | 66.5% | 39.1% |
| *Raphanus* (radish) (Accession #D84669) | 56.7% | 37.4% |
| *Helianthus* (Accession #X95951) | 50.4% | 35.2% |
| High Affinity Ammonium Transporter | | |
| *Arabidopsis* (Accession #X75879) | 100% | 100% |
| Tomato (Accession #X95098) | 73.5% | 62.9% |
| Rice (Accession #AF001505) | 66.6% | 58.1% |

Nucleic Acid Molecules and Polypeptides Similar to AtNHX

Those skilled in the art will recognize that the nucleic acid molecule sequences in FIGS. 1(a), (b), (d) and (e) are not the only sequences which may be used to provide increased salt tolerance in plants. The genetic code is degenerate so other nucleic acid molecules which encode a polypeptide identical to an amino acid sequence in FIG. 1(a), (b), (d) or (e) may also be used. The sequence of the other nucleic acid molecules of this invention may also be varied without changing the polypeptide encoded by the sequence. Consequently, the nucleic acid molecule constructs described below and in the accompanying examples for the preferred nucleic acid molecules, vectors, and transformants of the invention are merely illustrative and are not intended to limit the scope of the invention.

The sequences of the invention can be prepared according to numerous techniques. The invention is not limited to any particular preparation means. For example, the nucleic acid molecules of the invention can be produced by cDNA cloning, genomic cloning, DNA synthesis, polymerase chain reaction (PCR) technology, or a combination of these approaches ((31) or Current Protocols in Molecular Biology (F. M. Ausbel et al., 1989).). Sequences may be synthesized using well known methods and equipment, such as automated synthesizers. Nucleic acid molecules may be amplified by the polymerase chain reaction. Polypeptides may, for example, be synthesized or produced recombinantly.

Sequence Identity

The invention includes modified nucleic acid molecules with a sequence identity at least about: >17%, >20%, >30%, >40%, >50%, >60%, >70%, >80% or >90% more preferably at least about >95%, >99% or >99.5%, to a DNA sequence in FIG. 1 or 5 (or a partial sequence thereof). Preferably about 1, 2, 3, 4, 5, 6 to 10, 10 to 25, 26 to 50 or 51 to 100, or 101 to 250 nucleotides or amino acids are modified. Identity is calculated according to methods known in the art. Sequence identity is most preferably assessed by the Clustal W program. For example, if a nucleotide sequence (called "Sequence A") has 90% identity to a portion of the nucleotide sequence in FIG. 1(a), then Sequence A will be identical to the referenced portion of the nucleotide sequence in FIG. 1, except that Sequence A may include up to 10 point mutations, such as deletions or substitutions with other nucleotides, per each 100 nucleotide of the referenced portion of the nucleotide sequence in FIG. 1. Nucleotide sequences functionally equivalent to the PNHX or AtNHX sequences can occur in a variety of forms as described below. Polypeptides having sequence identity may be similarly identified.

The polypeptides encoded by the homologous NHX, PHX $Na^+/H^+$ exchange nucleic acid molecule in other species will have amino acid sequence identity (also known as homology) at least about: >20%, >25%, >28%, >30%, >40% or >50% to an amino acid sequence shown in FIG. 1 or 5 (or a partial sequence thereof.) Some plants species may have polypeptides with a sequence identity (homology) of at least about: >60%, >70%, >80% or >90%, more preferably at least about: >95%, >99% or >99.5% to all or part of an amino acid sequence in FIG. 1 or 5 (or a partial sequence thereof. Identity is calculated according to methods known in the art. Sequence identity is most preferably assessed by the Clustal W program. Preferably about: 1, 2, 3, 4, 5, 6 to 10, 10 to 25, 26 to 50 or 51 to 100, or 101 to 250 nucleotides or amino acids are modified.

The invention includes nucleic acid molecules with mutations that cause an amino acid change in a portion of the polypeptide not involved in providing salt tolerance and ion transport or an amino acid change in a portion of the polypeptide involved in providing salt tolerance so that the mutation increases or decreases the activity of the polypeptide.

Hybridization

Other functional equivalent forms of the AtNHX nucleic acid molecules encoding nucleic acids can be isolated using conventional DNA—DNA or DNA-RNA hybridization techniques. These nucleic acid molecules and the AtNHX sequences can be modified without significantly affecting their activity.

The present invention also includes nucleic acid molecules that hybridize to one or more of the sequences in FIG. 1 or 5 (or a partial sequence thereof) or their complementary sequences, and that encode expression for peptides or polypeptides exhibiting substantially equivalent activity as that of an AtNHX polypeptide produced by the DNA in FIG. 1 or their variants. Such nucleic acid molecules preferably hybridize to the sequences under low, moderate (intermediate), or high stringency conditions. (see Sambrook et al. (Most recent edition) Molecular Cloning: A Laboratory Manual, Cold Spring Harbor Laboratory Press, Cold Spring Harbor, N.Y.). Preferable hybridization conditions are about those in Table 4.

As used herein the phrase "low stringency conditions" refers the following conditions and equivalents thereto: hybridization at 5×SSC, 2% SDS, and 100 µg/ml single stranded DNA at 40° C. for 17 hours followed by washing 2×SSC, 0.2% SDS, at 50° C. for thirty minutes.

As used the phrase "moderately stringent conditions" refers the following conditions and equivalents thereto: hybridization at 5×SSC, 2% SDS, and 100 µg/ml single stranded DNA at 50° C. for 17 hours, followed by washing in 0.1% SDS, at 50° C. for thirty minutes As used herein, the phrase "highly stringent conditions" refers the following conditions and equivalents thereto: hybridization at 5×SSC, 2% SDS, and 100 µg/ml single stranded DNA at 65° C. for 17 hours followed by washing in 0.1×SSC, 0.1% SDS, at 65° C. for thirty minutes.

The present invention also includes nucleic acid molecules from any source, whether modified or not, that hybridize to genomic DNA, cDNA, or synthetic DNA molecules that encode the amino acid sequence of an AtNHX polypeptide, or genetically degenerate forms, under salt and temperature conditions equivalent to those described in this application, and that code for a peptide, polypeptide or polypeptide that has $Na^+/H^+$ transporter activity. Preferably the polypeptide has the same or similar activity as that of an AtNHX polypeptide. The nucleic acid molecules may encode TNHX or PNHX polypeptides. A nucleic acid molecule described above is considered to be functionally equivalent to an AtNHX nucleic acid molecule (and thereby having $Na^+/H^+$ transporter activity) of the present invention if the polypeptide produced by the nucleic acid molecule displays the following characteristics: the polypeptide mediates the proton-dependent sodium transport and sodium-dependent proton transport in intact cells, isolated organelles and purified membrane vesicles. These sodium/proton movements should be higher (preferably at least about 50% higher and most preferably at least about 100% higher) than the proton movements observed in the presence of a background of potassium ions and/or other monovalent cations (i.e. rubidium, cesium, etc., but most preferably not lithium) (13, 14).

The invention also includes nucleic acid molecules and polypeptides having sequence similarity taking into account conservative amino acid substitutions. Sequence similarity (and preferred percentages) are discussed below.

Modifications to Nucleic Acid Molecule or Polypeptide Sequence

Changes in the nucleotide sequence which result in production of a chemically equivalent or chemically similar amino acid sequences are included within the scope of the invention. Variants of the polypeptides of the invention may occur naturally, for example, by mutation, or may be made, for example, with polypeptide engineering techniques such as site directed mutagenesis, which are well known in the art for substitution of amino acids. For example, a hydrophobic residue, such as glycine can be substituted for another hydrophobic residue such as alanine. An alanine residue may be substituted with a more hydrophobic residue such as leucine, valine or isoleucine. A negatively charged amino acid such as aspartic acid may be substituted for glutamic acid. A positively charged amino acid such as lysine may be substituted for another positively charged amino acid such as arginine.

Therefore, the invention includes polypeptides having conservative changes or substitutions in amino acid sequences. Conservative substitutions insert one or more amino acids which have similar chemical properties as the replaced amino acids. The invention includes sequences where conservative substitutions are made that do not destroy $Na^+/H^+$ transporter activity of the transporter polypeptide. The preferred percentage of sequence similarity for sequences of the invention includes sequences having at least about: 48% similarity to AtNHX1, 48% similarity to AtNHX2, 56% similarity to AtNHX3, and 56% similarity to AtNHX4. The similarity may also be at least about: 60% similarity, 75% similarity, 80% similarity, 90% similarity, 95% similarity, 97% similarity, 98% similarity, 99% similarity, or more preferably at least about 99.5% similarity, wherein the polypeptide $Na^+/H^+$ has transporter activity. The invention also includes nucleic acid molecules encoding polypeptides, with the polypeptides having at least about: at least about: 48% similarity to AtNHX1, 48% similarity to AtNHX2, 56% similarity to AtNHX3, and 56% similarity to AtNHX4. The similarity may also be at least about: 60% similarity, 75% similarity, 80% similarity, 90% similarity, 95% similarity, 97% similarity, 98% similarity, 99% similarity, or more preferably at least about 99.5% similarity, wherein the polypeptide $Na^+/H^+$ has transporter activity, to an amino acid sequence in FIG. 1 or 5 (or a partial sequence thereof) considering conservative amino acid changes, wherein the polypeptide has $Na^+/H^+$ transporter activity. Sequence similarity is preferably calculated as the number of similar amino acids in a pairwise alignment expressed as a percentage of the shorter of the two sequences in the alignment. The pairwise alignment is preferably constructed using the Clustal W program, using the following parameter settings: fixed gap penalty=10, floating gap penalty=10, protein weight matrix=BLOSUM62. Similar amino acids in a pairwise alignment are those pairs of amino acids which have positive alignment scores defined in the preferred protein weight matrix (BLOSUM62). The protein weight matrix BLOSUM62 is considered appropriate for the comparisons described here by those skilled in the art of bioinformatics. (The reference for the clustal w program (algorithm) is Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673–4680; and the reference for BLOSUM62 scoring matrix is Henikoff, S. and Henikoff, J. G. (1993) Performance evaluation of amino acid substitution matrices. Proteins, 7:49–61.)

Polypeptides comprising one or more d-amino acids are contemplated within the invention. Also contemplated are polypeptides where one or more amino acids are acetylated at the N-terminus. Those of skill in the art recognize that a variety of techniques are available for constructing polypeptide mimetics with the same or similar desired biological activity ($Na^+/H^+$ transporter activity) as the corresponding polypeptide compound of the invention but with more favorable activity than the polypeptide with respect to solubility, stability, and/or susceptibility to hydrolysis and proteolysis. See, for example, Morgan and Gainor, *Ann. Rep. Med. Chem.*, 24:243–252 (1989). Examples of polypeptide mimetics are described in U.S. Pat. No. 5,643,873. Other patents describing how to make and use mimetics include, for example in, U.S. Pat. No. 5,786,322, U.S. Pat. No. 5,767,075, U.S. Pat. No. 5,763,571, U.S. Pat. No. 5,753,226, U.S. Pat. No. 5,683,983, U.S. Pat. No. 5,677,280, U.S. Pat. No. 5,672,584, U.S. Pat. No. 5,668,110, U.S. Pat. No. 5,654,276, U.S. Pat. No. 5,643,873. Mimetics of the polypeptides of the invention may also be made according to other techniques known in the art. For example, by treating a polypeptide of the invention with an agent that chemically alters a side group by converting a hydrogen group to another group such as a hydroxy or amino group. Mimetics preferably include sequences that are either entirely made of amino acids or sequences that are hybrids including amino acids and modified amino acids or other organic molecules.

The invention also includes hybrid nucleic acid molecules and polypeptides, for example where a nucleotide sequence from one species of plant is combined with a nucleotide sequence from another sequence of plant, mammal or yeast to produce a fusion polypeptide. The invention includes a fusion protein having at least two components, wherein a first component of the fusion protein comprises a polypeptide of the invention, preferably a full length AtNHX polypeptide. The second component of the fusion protein preferably comprises a tag, for example GST, an epitope tag or an enzyme. The fusion protein may comprise lacZ.

The invention also includes polypeptide fragments of the polypeptides of the invention which may be used to confer salt tolerance if the fragments retain $Na^+/H^+$transporter activity. The invention also includes polypeptides fragments of the polypeptides of the invention which may be used as a research tool to characterize the polypeptide or its activity. Such polypeptides preferably consist of at least 5 amino acids. In preferred embodiments, they may consist of 6 to 10, 11 to 15, 16 to 25, 26 to 50, 51 to 75, 76 to 100 or 101 to 250 amino acids of the polypeptides of the invention (or longer amino acid sequences). The fragments preferably have sodium/proton transporter activity. Fragments may include sequences with one or more amino acids removed, for example, C-terminus amino acids in an AtNHX sequence.

The invention also includes a composition comprising all or part of an isolated TNHX or PNHX (preferably AtNHX) nucleic acid molecule of the invention and a carrier, preferably in a composition for plant transformation. The invention also includes a composition comprising an isolated TNHX or PNHX polypeptide (preferably AtNHX) and a carrier, preferably for studying polypeptide activity.

Recombinant Nucleic Acid Molecules

The invention also includes recombinant nucleic acid molecules comprising a nucleic acid molecule of the invention and a promoter sequence, operatively linked so that the promoter enhances transcription of the nucleic acid molecule in a host cell (the nucleic acid molecules of the invention may be used in an isolated native gene or a chimeric gene (for example, where a nucleic acid molecule coding region is connected to one or more heterologous sequences to form a gene). The promoter sequence is preferably a constitutive promoter sequence or an inducible promoter sequence, operatively linked so that the promoter enhances transcription of the DNA molecule in a host cell. The promoter may be of a type not naturally associated with the cell. Transcription is enhanced with promoters known in the art such as the "Super-promoter" (20) or the $^{35}$S promoter of cauliflower mosaic virus (21).

Inducible promoters are also used. These include:
a) drought- and ABA-inducible promoters which may include ABA-responsive elements (22,23)
b) heat shock-inducible promoters which may contain HSEs (heat shock elements) as well as CCAAT box sequences (24)
c) salt-inducible promoters which may include AT and PR elements (25)
d) Copper-inducible promoter that includes ACE1 binding sites (26)
e) steroid-inducible promoter that includes the glucocorticoid response element along with an expression vector coding for a mammalian steroid receptor (27).

In addition, tissue specific expression is achieved with the use of tissue-specific promoters such as, the Fd (Ferredoxin) promoter that mediates high levels of expression in green leaves (28) and peroxidase promoter for root-specific expression (29). These promoters vary in their transcription initiation rate and/or efficiency.

A recombinant nucleic acid molecule for conferring salt tolerance may also contain suitable transcriptional or translational regulatory elements. Suitable regulatory elements may be derived from a variety of sources, and they may be readily selected by one with ordinary skill in the art. Examples of regulatory elements include: a transcriptional promoter and enhancer or RNA polymerase binding sequence, a ribosomal binding sequence, including a translation initiation signal. Additionally, depending on the vector employed, other genetic elements, such as selectable markers, may be incorporated into the recombinant molecule. Markers facilitate the selection of a transformed host cell. Such markers include genes associated with temperature sensitivity, drug resistance, or enzymes associated with phenotypic characteristics of the host organisms.

Nucleic acid molecule expression levels are controlled with a transcription initiation region that regulates transcription of the nucleic acid molecule or nucleic acid molecule fragment of interest in a plant, bacterial or yeast cell. The transcription initiation region may be part of the construct or the expression vector. The transcription initiation domain or promoter includes an RNA polymerase binding site and an mRNA initiation site. Other regulatory regions that may be used include an enhancer domain and a termination region. The regulatory elements described above may be from animal, plant, yeast, bacterial, fungal, viral or other sources, including synthetically produced elements and mutated elements.

Methods of modifying DNA and polypeptides, preparing recombinant nucleic acid molecules and vectors, transformation of cells, expression of polypeptides are known in the art. For guidance, one may consult the following U.S. Pat. Nos. 5,840,537, 5,850,025, 5,858,719, 5,710,018, 5,792,851, 5,851,788, 5,759,788, 5,840,530, 5,789,202, 5,871,983, 5,821,096, 5,876,991, 5,422,108, 5,612,191, 5,804,693, 5,847,258, 5,880,328, 5,767,369, 5,756,684, 5,750,652, 5,824,864, 5,763,211, 5,767,375, or 5,750,848. Many of these patents also provide guidance with respect to experimental assays, probes and antibodies, transformation of host cells and regeneration of plants, which are described below. These patents, like all other patents, publications (such as articles and Genbank publications) in this application, are incorporated by reference in their entirety.

Host Cells Including a Salt Tolerance Nucleic Acid Molecule

In a preferred embodiment of the invention, a plant or yeast cell is transformed with a nucleic acid molecule of the invention or a fragment of a nucleic acid molecule and inserted in a vector.

Another embodiment of the invention relates to a method of transforming a host cell with a nucleic acid molecule of the invention or a fragment of a nucleic acid molecule, inserted in a vector. The invention also includes a vector comprising a nucleic acid molecule of the invention. The TNHX, PNHX and AtNHX nucleic acid molecules can be cloned into a variety of vectors by means that are well known in the art. The recombinant nucleic acid molecule may be inserted at a site in the vector created by restriction enzymes. A number of suitable vectors may be used, including cosmids, plasmids, bacteriophage, baculoviruses and viruses. Suitable vectors are capable of reproducing themselves and transforming a host cell. The invention also relates to a method of expressing polypeptides in the host cells. A nucleic acid molecule of the invention may be used to transform virtually any type of plant, including both monocots and dicots. The expression host may be any cell capable of expressing TNHX, PNHX, such as a cell selected from the group consisting of a seed (where appropriate), plant cell, bacterium, yeast, fungus, protozoa, algae, animal and animal cell.

Levels of nucleic acid molecule expression may be controlled with nucleic acid molecules or nucleic acid molecule fragments that code for anti-sense RNA inserted in the vectors described above.

*Agrobacterium tumefaciens*-mediated transformation, particle-bombardment-mediated transformation, direct uptake, microinjection, coprecipitation and electroporation-mediated nucleic acid molecule transfer are useful to transfer a $Na^+/H^+$ transporter nucleic acid molecule into seeds (where appropriate) or host cells, preferably plant cells, depending upon the plant species. The invention also includes a method for constructing a host cell capable of expressing a nucleic acid molecule of the invention, the method comprising introducing into said host cell a vector of the invention. The genome of the host cell may or may not also include a functional TNHX or PNHX gene. The invention also includes a method for expressing a TNHX or PNHX transporter polypeptide in the host cell or a plant, plant part, seed or plant cell of the invention, the method comprising culturing the host cell under conditions suitable for gene expression. The method preferably also includes recovering the expressed polypeptide from the culture.

The invention includes the host cell comprising the recombinant nucleic acid molecule and vector as well as progeny of the cell. Preferred host cells are fungal cells, yeast cells, bacterial cells, mammalian cells, bird cells, reptile cells, amphibious cells, microorganism cells and plant cells. Host cells may be cultured in conventional nutrient media. The media may be modified as appropriate for inducing promoters, amplifying genes or selecting transformants. The culture conditions, such as temperature, composition and pH will be apparent. After transformation, transformants may be identified on the basis of a selectable phenotype. A selectable phenotype can be conferred by a selectable marker in the vector.

Transgenic Plants and Seeds

Plant cells are useful to produce tissue cultures, seeds or whole plants. The invention includes a plant, plant part, seed, or progeny thereof including a host cell transformed with a PNHX nucleic acid molecule. The plant part is preferably a leaf, a stem, a flower, a root, a seed or a tuber.

The invention includes a transformed (transgenic) plant having increased salt tolerance, the transformed plant containing a nucleic acid molecule sequence encoding for $Na^+/H^+$ transporter polypeptide activity and the nucleic acid molecule sequence having been introduced into the plant by transformation under conditions whereby the transformed plant expresses a $Na^+/H^+$ transporter in active form.

The methods and reagents for producing mature plants from cells are known in the art. The invention includes a method of producing a genetically transformed plant which expresses PNHX or TNHX polypeptide by regenerating a genetically transformed plant from the plant cell, seed or plant part of the invention. The invention also includes the transgenic plant produced according to the method. Alternatively, a plant may be transformed with a vector of the invention.

The invention also includes a method of preparing a plant with increased salt tolerance, the method comprising transforming the plant with a nucleic acid molecule which encodes a TNHX transporter polypeptide, a PNHX transporter polypeptide or a polypeptide encoding a $Na^+/H^+$ transporter polypeptide capable of increasing salt tolerance in a cell, and recovering the transformed plant with increased salt tolerance. The invention also includes a method of preparing a plant with increased salt tolerance, the method comprising transforming a plant cell with a nucleic acid molecule which encodes a TNHX transporter polypeptide, a PNHX transporter polypeptide or a polypeptide encoding a Na+/H+ transporter polypeptide capable of increasing salt tolerance in a cell, and producing the transformed plant with increased salt tolerance.

Overexpression of $Na^+/H^+$ exchangers leads to an improved ability of the transgenic plants to uptake more monovalent cations from the growth media (soil) leading to an increased or enhanced tissue expansion. FIG. 7 shows that transformed plants have grown larger even where no NaCl is added to soil. Therefore, the invention also relates to methods of producing or growing plants with increased tissue expansion (this could be manifested as enhanced size, growth or growth potential and may appear as increased or enhanced root, crown, shoot, stem, leaf, flower size or abundance in comparison to a wild type plant). The methods of preparing plants that have increased tissue expansion are the same as the methods for preparing a plant with increased salt tolerance described in this application (or the methods are easily adapted, to the extent that there is a difference in the methods).

The plants whose cells may be transformed with a nucleic acid molecule of this invention and used to produce transgenic plants include, but are not limited to the following:
Target Plants:
Group I (Transformable Preferably via *Agrobacterium tumefaciens*)
*Arabidopsis*
Potato
Tomato
*Brassica*
Cotton
Sunflower
Strawberries
Spinach
Lettuce
Rice.
Group II (Transformable Preferably via Biolistic Particle Delivery Systems (Particle Bombardment)
Soybean
Rice
Corn
Wheat
Rye
Barley
*Atriplex*
Salicornia.

The nucleic acid molecule may also be used with other plants such as oat, barley, hops, sorgum, alfalfa, sunflower, alfalfa, beet, pepper, tobacco, melon, squash, pea, cacao, hemp, coffee plants and grape vines. Trees may also be transformed with the nucleic acid molecule. Such trees include, but are not limited to maple, birch, pine, oak and poplar. Decorative flowering plants such as carnations and roses may also be transformed with the nucleic acid molecule of the invention. Plants bearing nuts such as peanuts may also be transformed with the salt tolerance nucleic acid molecule. A list of preferable plants is in Table 5.

In a preferred embodiment of the invention, plant tissue cells or cultures which demonstrate salt tolerance are selected and plants which are salt tolerant are regenerated from these cultures. Methods of regeneration will be apparent to those skilled in the art (see Examples below, also). These plants may be reproduced, for example by cross pollination with a plant that is salt tolerant or a plant that is not salt tolerant. If the plants are self-pollinated, homozygous salt tolerant progeny may be identified from the seeds of these plants, for example by growing the seeds in a saline environment, using genetic markers or using an assay for salt tolerance. Seeds obtained from the mature plants resulting from these crossings may be planted, grown to sexual maturity and cross-pollinated or self-pollinated.

The nucleic acid molecule is also incorporated in some plant species by breeding methods such as back crossing to create plants homozygous for the salt resistance nucleic acid molecule.

A plant line homozygous for the salt tolerance nucleic acid molecule may be used as either a male or female parent in a cross with a plant line lacking the salt tolerance nucleic acid molecule to produce a hybrid plant line which is uniformly heterozygous for the nucleic acid molecule. Crosses between plant lines homozygous for the salt resistance nucleic acid molecule are used to generate hybrid seed homozygous for the resistance nucleic acid molecule.

The nucleic acid molecule of the invention may also be used as a marker in transformation experiments with plants. A salt sensitive plant may be transformed with a salt tolerance nucleic acid molecule and a nucleic acid molecule of interest which are linked. Plants transformed with the nucleic acid molecule of interest will display improved growth in a saline environment relative to the non-transformed plants.
Fragments/Probes Preferable fragments (fragments are also referred to as polypeptide fragments or peptide fragments) include 10 to 50, 50 to 100, 100 to 250, 250 to 500, 500 to 1000, 1000 to 1500, or 1500 or more nucleotides of a nucleic acid molecule of the invention. A fragment may be generated by removing a single nucleotide from a sequence in FIG. 1 or 5 (or a partial sequence thereof). Fragments may or may not have $Na^+/H^+$ transporter activity.

The nucleic acid molecules of the invention (including a fragment of a sequence in FIG. 1 or 5 (or a partial sequence thereof) (such as SEQ ID NO:1, SEQ ID NO:3, SEQ ID NO:5 or SEQ ID NO:7) can be used as probes to detect nucleic acid molecules according to techniques known in the art (for example, see U.S. Pat. Nos. 5,792,851 and 5,851,788). The probes may be used to detect nucleic acid molecules that encode polypeptides similar to the polypeptides of the invention. For example, a probe having at least about 10 bases will hybridize to similar sequences under stringent hybridization conditions (Sambrook et al. 1989, Molecular Cloning, A Laboratory Manual, Cold Spring Harbor).

The invention includes oligonucleotide probes made from the AtNHX sequences described in this application or other nucleotide sequences of the invention. The probes may be about 10 to 30 or 15 to 30 nucleotides in length and are preferably at least 30 or more nucleotides. A preferred probe is 5'-TTCTTCATATATCTTTTGCCACCC-3' SEQ ID NO:36 (coding for the amiloride binding domain) or at least about 10 or 15 nucleotides of this sequence. The invention also includes an oligonucleotide including at least 30 consecutive nucleotides of an AtNHX molecule in FIG. 1 or 5 (or a partial sequence thereof). The probes are useful to identify nucleic acids encoding AtNHX, polypeptides and proteins other than those described in the application, as well as peptides, polypeptides, and proteins have Na+/H+ transporter activity and preferably functionally equivalent to AtNHX. The oligonucleotide probes are capable of hybridizing to one or more of the sequences shown in FIG. 1 or 5 (or a partial sequence thereof) or the other sequences of the invention under low, moderate or high stringency hybridization conditions. A nucleotide sequence encoding a polypeptide of the invention may be isolated from other organisms by screening a library under low, moderate or high stringency hybridization conditions with a detectable probe (e.g. a labeled probe). The activity of the polypeptide encoded by the nucleotide sequence may be assessed by cloning and expression of the DNA. After the expression product is isolated, the polypeptide is assayed for Na+/H+ transporter activity as described in this application.

Functionally equivalent AtNHX, TNHX or PNHX nucleic acid molecules from other cells, or equivalent AtNHX, TNHX or PNHX-encoding cDNAs or synthetic DNAs, can also be isolated by amplification using Polymerase Chain Reaction (PCR) methods. Oligonucleotide primers, including degenerate primers, based on the amino acid sequence of the sequences in FIG. 1 or 5 (or a partial sequence therof) can be prepared and used in conjunction with PCR technology employing reverse transcriptase to amplify functionally equivalent DNAs from genomic or cDNA libraries of other organisms. Alternatively, the oligonucleotides, including degenerate nucleotides, can be used as probes to screen cDNA libraries.

Thus, the invention includes an oligonucleotide probe comprising all or part of a nucleic acid in FIG. 1 or 5 (or a partial sequence thereof), or a complementary strand thereof. The probe is preferably labeled with a detectable marker. The invention also includes an oligonucleotide comprising at least 10, 15 or 30 nucleotides capable of specifically hybridizing with a sequence of nucleic acids of the nucleotide sequence set forth in FIG. 1 or 5 (or a partial sequence thereof). The invention also includes a single strand DNA primer for amplification of PNHX nucleic acid, wherein the primer is selected from a nucleic acid sequence derived from a nucleic acid sequence in FIG. 1 or 5 (or a partial sequence thereof.

The invention also includes a method for identifying nucleic acid molecules encoding a TNHX, PNHX or AtNHX polypeptide. Techniques for performing the methods are described in, for example, U.S. Pat. Nos. 5,851,788 and 5,858,719. A preferred method includes contacting a sample containing nucleic acids with an oligonucleotide, wherein said contacting is effected under low, moderate or high stringency hybridization conditions, and identifying nucleic acids which hybridize thereto. Hybridization forms a hybridization complex. The presence of a complex correlates with the presence of a nucleic acid molecule encoding TNHX, plant PNHX polypeptide or AtNHX in the sample. In a preferred method, the nucleic acid molecules are amplified by the polymerase chain reaction prior to hybridization.

Kits

The invention also includes a kit for conferring increased salt tolerance to a plant or a host cell including a nucleic acid molecule of the invention (preferably in a composition to the invention) and preferably reagents for transforming the plant or host cell.

The invention also includes a kit for detecting the presence of a TNHX or a PNHX nucleic acid molecule, comprising at least one oligonucleotide of the invention. Kits may be prepared according to known techniques, for example, see U.S. Pat. Nos. 5,851,788 and 5,750,653.

Antibodies

The invention includes an isolated antibody immunoreactive with a polypeptide of the invention (see Example 1). The antibody may be labeled with a detectable marker or unlabeled. The antibody is preferably a monoclonal antibody or a polyclonal antibody. TNHX, PNHX or AtNHX antibodies can be employed to screen organisms containing TNHX, PNHX or AtNHX polypeptides. The antibodies are also valuable for immunopurification of polypeptides from crude extracts.

The isolated antibody is preferably specifically reactive with a TNHX or PNHX transporter, preferably an AtNHX transporter. The transporter is preferably encoded by a nucleic acid molecule in FIG. 1 (or molecules that hybridize to a molecule in FIG. 1 under low, moderate or high stringency hybridization conditions or molecules having at least about: 17%, at least 20%, at least 25%, or at least 35% sequence identity (or the other preferred percentages of identity or sequence similarity described above) to a molecule in FIG. 1 or 5 (or a partial sequence thereof. The transporter is preferably a polypeptide in FIG. 1 (or polypeptides having at least about: 28%, 35% sequence identity (or the other preferred percentages of identity or sequence similarity described above) to a polypeptide in FIG. 1 or 5 (or a partial sequence thereof). The antibody preferably does not cross-react with other transporter polypeptides. The antibody is preferably specifically reactive with a polypeptide having an amino acid sequence encoded by a nucleic acid molecule set forth in FIG. 1 or 5 (or a partial sequence thereof).

Examples of the preparation and use of antibodies are provided in U.S. Pat. Nos. 5,792,851 and 5,759,788. For other examples of methods of the preparation and uses of monoclonal antibodies, see U.S. Pat. Nos. 5,688,681, 5,688,657, 5,683,693, 5,667,781, 5,665,356, 5,591,628, 5,510,241, 5,503,987, 5,501,988, 5,500,345 and 5,496,705. Examples of the preparation and uses of polyclonal antibodies are disclosed in U.S. Pat. Nos. 5,512,282, 4,828,985, 5,225,331 and 5,124,147.

The invention also includes methods of using the antibodies. For example, the invention includes a method for detecting the presence of TNHX, PNHX or AtNHX transporter polypeptide, by: a) contacting a sample containing one or more polypeptides with an antibody of the invention under conditions suitable for the binding of the antibody to polypeptides with which it is specifically reactive; b) separating unbound polypeptides from the antibody; and c) detecting antibody which remains bound to one or more of the polypeptides in the sample.

Research Tool

Cell cultures, seeds, plants and plant parts transformed with a nucleic acid molecule of the invention are useful as research tools. For example, one may obtain a plant cell (or a cell line, such as an immortalized cell culture or a primary cell culture) that does not express AtNHX1, insert an AtNHX1 nucleic acid molecule in the cell, and assess the level of AtNHX1 expression and activity. Alternatively, PNHX nucleic acid molecules may be overexpressed in a plant that expresses a PNHX nucleic acid molecule. In another example, experimental groups of plants may be transformed with vectors containing different types of PNHX nucleic acid molecules (or PNHX nucleic acid molecules similar to PNHX or fragments of PNHX nucleic acid molecules) to assess the levels of protein produced, its functionality and the phenotype of the plants (for example, phenotype in saline soil). The polypeptides are also useful for in vitro analysis of TNHX, PNHX or AtNHX activity or structure. For example, the polypeptides produced can be used for microscopy or X-ray crystallography studies.

The TNHX, PNHX or AtNHX nucleic acid molecules and polypeptides are also useful in assays. Assays are useful for identification and development of compounds to inhibit and/or enhance polypeptide function directly. For example, they are useful in an assay for evaluating whether test compounds are capable of acting as antagonists for PNHX polypeptides by: (a) culturing cells containing: a nucleic acid molecule which expresses PNHX polypeptides (or polypeptides having PNHX or Na+/H+ activity) wherein the culturing is carried out in the presence of: increasing concentrations of at least one test compound whose ability to inhibit transport activity of PNHX polypeptide is sought to be determined, and a fixed concentration of salt; and (b) monitoring in the cells the level of salt transported out of the cytosol as a function of the concentration of the test compound, thereby indicating the ability of the test compound to inhibit PNHX transporter activity. Alternatively, the concentration of the test compound may be fixed and the concentration of salt may be increased.

Another experiment is an assay for evaluating whether test compounds are capable of acting as agonists for PNHX polypeptide characterized by being able to transport salt across a membrane, (or polypeptides having PNHX or Na+/H+ transporter activity) by (a) culturing cells containing: a nucleic acid molecule which expresses PNHX polypeptide or (or polypeptides having PNHX activity) thereof, wherein said culturing is carried out in the presence of: fixed concentrations of at least one test compound whose ability to increase or enhance salt transport activity of PNHX polypeptide is sought to be determined, and an increasing concentration of salt; and (b) monitoring in the cells the level of salt transported out of the cytosol as a function of the concentration of the test compound, thereby indicating the ability of the test compound compound to increase or enhance PNHX polypeptide activity. Alternatively, the concentration of the test compound may be fixed and the concentration of salt may be increased. Suitable assays may be adapted from, for example, U.S. Pat. No. 5,851,788. It is apparent that TNHX and AtNHX may also be used in assays.

Bioremediation

Soils containing excessive salt may be unable to grow plants in a manner suitable for agriculture. The invention includes a method for removing salt from a growth medium, comprising growing a plant transformed with a nucleic acid molecule of the invention and expressing a salt tolerance $Na^+/H^+$ transporter polypeptide in the growth medium for a time period sufficient for the plant root to uptake and accumulate salt in the root or shoot biomass. The growth medium may be a solid medium, semi-solid medium, liquid medium or a combination thereof. It may include soil, sand, sludge, compost, or artificial soil mix. The shoot (leaf or stem) or and root biomass may be harvested. Preferably, a sufficient portion of the shoot biomass is not harvested and is left in the growth media to permit continued plant growth.

Using Exogenous Agents in Combination with a Vector

The nucleic acid molecules of the invention may be used with other nucleic acid molecules that relate to salt tolerance, for example, osmoregulant genes. Host cells or plants may be transformed with these nucleic acid molecules. Osmoregulants are disclosed, for example, in U.S. Pat. Nos. 5,563,324 and 5,639, 950.

It will be clear to those skilled in the art that sequences in FIGS. 1(c) and 5(a) and (b) are also useful, for example in preparation of probes or as experimental tools or as antigens to which antibodies may be directed. The following Examples are intended to illustrate and assist in the further understanding of the invention. Particular materials employed, species, conditions and the like are not intended to limit the reasonable scope of the invention.

EXAMPLE 1

Preparation of Polyclonal and Monoclonal Antibodies.

Hydropathy profiles of the *Arabidopsis* $Na^+/H^+$ antiport revealed a relatively hydrophilic domain (at the C-terminus) with possible regulatory functions. The C-terminus was sub-cloned into the pGEX-2TK vector (Pharmacia) to allow the overexpression of the C-terminus polypeptide as a GST-fusion polypeptide in *E. Coli*. The fusion polypeptide was purified by glutathione-affinity chromatography and used as an antigen in rabbits to obtain polyclonal antibodies (30).

Monoclonal antibodies are prepared in mice hybridomas according to established techniques (30) using the C-terminus polypeptide as described above. Polyclonal and monoclonal antibodies raised against other regulatory regions of the *Arabidopsis* $Na^+/H^+$ antiport are also obtained as described above. The invention includes the antibodies and the hybridoma which secretes the monoclonal antibodies.

EXAMPLE 2

Identification of Homologous Nucleic Acid Molecules from Other Plant Species, Preferably Salt Tolerant Species.

Several experimental approaches are used to identify homologous nucleic acid molecules from salt tolerant species. a) We screen cDNA and genomic libraires from sugar beets (a moderate salt-tolerant crop, also known as red beet) under low-stringency conditions with an *Arabidopsis* $Na^+/H^+$ antiport cDNA as a probe (31); b) We apply PCR techniques using degenerate oligonucleotide primers designed according to the conserved regions of the *Arabidopsis* $Na^+/H^+$ antiport (32); c) We screen cDNA expression libraries from different plants (salt-tolerant and salt-sensitive) using antibodies raised against an *Arabidopsis* $Na^+/H^+$ antiport (31). We also use bioinformatics techniques to identify nucleic acid molecules. The invention includes methods of using such a nucleic acid molecule, for example to express a recombinant polypeptide in a transformed cell.

The techniques described above for isolating nucleic acid molecules from *Arabidopsis* and sugar beet are used to isolate a salt tolerance nucleic acid molecule from *Atriplex* and other plants.

EXAMPLE 3

Overexpression of the PNHX Transporter, Preferably *Arabidopsis* transporter (AtNHX).

The Na$^+$/H$^+$ antiport is expressed in *Arabidopsis* plants, although the wild type plants show impaired growth at NaCl concentrations higher than 75 mM. The Na$^+$/H$^+$ antiport is overexpressed in these plants in order to improve their tolerance to high salt concentrations. A full length cDNA (preferably coding for the AtNHX1 polypeptide (AtNHX2, AtNHX3 or AtNHX4) cloned from an *Arabidopsis thaliana* (Columbia) seedling cDNA library is ligated into a pBINS1 vector (33). This vector contains a constitutively strong promotor ("super-promotor' (20)). Also, T-DNA vectors (pBECKS) are used (34). Constructs containing the AtNHX1 cDNA with the full Na$^+$/H$^+$ antiport open reading frame in a sense orientation were selected by colony hybridization using the AtNHX1 as a probe and by restriction-digest analysis using BglII restriction endonuclease. These constructs are used to transform *Agrobacterium tumefaciens*, and these transformed *Agrobacterium tumefaciens* are used for transformation of *Arabidopsis* plants. The *Agrobacterium* for inoculation is grown at 28° C. in a medium containing 5 g/l Bacto Beef Extract, 5 g/l Bacto-Peptone, 1 g/l Bacto Yeast Extract, 240 mg MgSO$_4$ and 5 g/l sucrose. The pH will be adjusted to 7.2 with NaOH.

*Arabidopsis* seeds are washed and surface-sterilized in 5% (w/v) sodium hypochlorite containing 0.15% (v/v) Tween-20. The seeds are rinsed thoroughly with sterile distilled water. Seed aliquots are dispensed in flasks containing 45 ml of cocultivation medium (MS salts, 100 mM sucrose, 10 mg/l thiamine, 0.5 mg/l pyridoxine, 0.5 mg/l nicotinic acid, 100 mg/l inositol and the pH adjusted to 6.0 with KOH. The flasks are incubated at 22° C. under constant rotation (190 rpm) and constant light. After 10–18 h (time needed to break clumps of seeds) 5 ml of log phase of *Agrobacterium* (OD$_{600}$=0.75) carrying the AtNHX1 construct are added. Twenty-four hours following the inoculation, the seeds are dried by filtration and sown into pre-soaked vermiculite. The flats containing the seeds are irrigated as required with a half-Hoagland solution. The flats are covered with plastic to prevent desiccation and maintained at low artificial illumination. After 3 days the flats are transferred to the greenhouse (the plastic cover removed) under a 16/8 day/night cycle. Supplementary light is provided by high pressure sodium vapor lights. Seven weeks after sowing, the plants are dried thoroughly and the seeds (T2) harvested. Transformation efficiency is estimated by plating 100,000 seeds (approximately 2.5 g of seeds) on agar plates containing 50 mg/l kanamycin in a medium containing 1% (w/v) sucrose, 0.8 (w/v) agar, MS salts and a pH 6.0 adjusted with KOH. The plates are transferred to a growth room at 25° C. under continuous light. After 10 days the kanamycin-resistant seedlings are transferred to new growth medium for 2 weeks and then transferred to small pots containing vermiculite. At senescence (8 weeks) the seeds are collected from single plants (T3). These seeds are germinated and used to assess salt tolerance of the transgenic plants.

EXAMPLE 4
Overexpression of TNHX or PNHX in Other Plants.

In a preferred method, overexpression of PNHX, preferably AtNHX1, AtNHX2, AtNHX3 or AtNHX4, in a number of plants (potato, tomato, *brassica*, cotton, sunflower, strawberries, spinach, lettuce, rice, soybean, corn, wheat, rye, barley, *atriplex*, salicornia, and others) is achieved by *Agrobacterium tumefaciens*-based transformation and/or particle bombardment (AtNHX2, AtNHX3, AtNHX4 are also useful in this example). The full length cDNA (coding for the AtNHX1) is ligated into the pBINS1 vector or pBECKS (as described above) and these constructs are used to transform *Agrobacterium tumefaciens* strain LBA4404. *Agrobacterium* used for inoculation is grown as described above. Cultured cells (callus), leaf explants, shoot and root cultures are used as targets for transformation. The targeted tissues are co-cultivated with the bacteria for 1–2 days. Afterwards, the tissue is transferred to a growth media containing kanamycin. After one week the tissue is transferred to a regeneration medium containing MS salts, 1% sucrose, 2.5 mg/l 3-benzyladenine, 1 mg/A zeatin, 0.75% agar and kanamycin. Weekly transfers to fresh regeneration media are performed.

In another preferred embodiment, overexpression constructs carrying the AtNHX1 cDNA are introduced into an electro-competent *Agrobacterium tumefaciens* (LBA4404) by electroporation. The *Agrobacteria* are plated on LB plates containing 50 mg/L kanamycin and grown for ~2 days at 30 CC to select for bacteria carrying the overexpression constructs. One liter liquid LB+kanamycin (50 mg/L) is inoculated with a single *Agrobacterium* colony selected from the LB (kanamycin 50 mg/L) plates. The culture is grown to a minimum of OD=1 (600 nm) for 2–3 days. The *Agrobacteria* are then pelleted and resuspended in 1 L infiltration medium (IM −0.5XMS salts; 0.5 g/L MES; 5% sucrose; 0.03% Silwet L-77). Flowering *Arabidopsis* plants with primary bolts reaching ~15 cm are used for the transformation procedure (T1). Pots of *Arabidopsis* plants are dunked into the 1M solution containing the *Agrobacteria* and left submerged for 26 minutes. The same procedure can be repeated after 8–12 days on the same plants. Plants are allowed to senesce, the plants are dried thoroughly and the seeds harvested. Seeds are plated on agar plates containing 25 mg/L kanamycin in a medium containing MS salts, 0.8% (w/v) agar adjusted to pH 6.0 with KOH. The plates are transferred to a growth room at 25° C. under continuous light. After 10 days the kanamycin-resistant seedlings (T2) are transferred to small pots containing vermiculite. At senescence (~8 weeks) the seeds are collected from single plants and plated on agar plates containing MS salts and 25 mg/L kanamycin. After 10 days the kanamycin-resistant seedlings (T3) are transferred to small pots containing vermiculite. Seeds produced by these plants are germinated and used to assess salt tolerance of the transgenic plants. A biolistic particle delivery system (particle bombardment) is also used for the overexpression of NHX (AtNHX1, AtNHX2, AtNHX3 or AtNHX4 are useful for this example). Constructs made using a plasmid vector preferably carrying a constitutive promoter, the AtNHX1 open reading frame in a sense orientation and a NOS termination site are used. Plasmid DNA is precipitated into 1.25 mg of 1–2 μm gold particles using 25 μl of 2.5 M CaCl$_2$ and 10 μl of 0.1 M thiamine (free base). DNA-coated particles are washed with 125 μl of 100% ethanol and then resuspended in 30 μl ethanol. The samples are sonicated to obtain an efficient dispersion, and the samples are aliquoted to obtain delivery disks containing 3 μg of DNA each. Particle bombardment is optimized according to the specific tissue to be transformed. Tissue samples are placed in Petri dishes containing 4.5 g/l basal MS salts, 1 mg/l thiamine, 10 mg/l myoinositol, 30 g/l sucrose, 2.5 mg/l amphotericin and 10 mM K$_2$HPO$_4$ at pH 5.7. After bombardment the petri dishes are incubated for 18–24 hours. Tissue is regenerated in plates with growth media containing the selective marker. Rooting is initiated and transformed plants are grown under optimal growth conditions in growth chambers. After 2–4 weeks the seedlings are transferred to new growth medium for 2 weeks and then transferred to small pots containing vermiculite. At senescence the seeds are collected from single plants. These seeds are germinated and used to assess salt tolerance of the transgenic plants.

EXAMPLE 5

Overexpression of AtNHX1-Homologs in Other Plants.

Overexpression of AtNHX1-homologs from other plant species, preferably salt tolerant species (i.e., sugar beet) in other plants (potato, tomato, *brassica*, cotton, sunflower, strawberries, spinach, lettuce, rice, soybean, corn, wheat, rye, barley, *atriplex*, salicornia, and others) is achieved by *Agrobacterium tumefaciens*-based transformation and/or particle bombardment as described above (in Examples 3 and 4). Regeneration of the transformed plants is performed as described in Examples 3 and 4 (AtNHX2, AtNHX3 or AtNHX4).

EXAMPLE 6

Expression of PNHX, AtNHX1, AtNHX1 homologs and AtNHX1 derivatives in *Saccharomyces cerevisiae*.

Expression of TNHX or PNHX, preferably AtNHX1, AtNHX1 homologs (such as AtNHX2, AtNHX3, AtNHX4), and AtNHX1 derivatives in yeast is useful to assess and characterize the biochemical properties of the recombinant and native polypeptides. Expression in yeast also facilitates the study of interactions between AtNHX1, its homologs and derivatives with regulatory polypeptides. We have made conditional expression constructs by ligating the coding region of the AtNHX1 cDNA into two vectors, pYES2 (Invitrogen) and pYEP434 (35). Both constructs provide galactose-inducible expression, but pYES2 has a URA3 selectable marker while pYEP434 has LEU2 as a selectable marker. Transformation by lithium acetate (36), 1994), is followed by selection on solid media containing amino acids appropriate for the selection of cells containing the transformation vector. For integrative transformation, the YXplac series of vectors for integrative transformation are used (37).

EXAMPLE 7

Molecular Characterization and Functional Analysis of $Na^+/H^+$ Exchangers from *Arabidopsis* and Other Plants, Preferably Salt-Tolerant (Halophytes) Plants.

We do molecular and biochemical characterization of the different $Na^+/H^+$ exchangers from *Arabidopsis* and other plants, preferably salt tolerant plants (halophytes). We determine the expression patterns of the different *Arabidopsis* putative exchangers. Using Northern blot analysis with isoform-specific cDNA probes under high stringency conditions and standard molecular biology protocols, we determine the tissue-specificity, developmental and salt-inducibility gene expression profiles of each isoform.

We employ common molecular biology procedures to isolate $Na^+/H^+$ exchangers from other plants (Table 5), in particular halophytes (such as *Beta vulgaris, Atriplex, Messembryanthemum chrystalinum*, etc.). We designed degenerate oligonucleotide PCR primers, based upon highly conserved regions within $Na^+/H^+$ exchangers (one within the amiloride-binding domain, and another within a region about 200 amino acid residues further downstream) from *Arabidopsis*, yeast, mammals, and *C. elegans*, to generate a 600–1,000 bp DNA fragments by PCR. Sequencing of these products revealed significant homology to AtNHX1 and they are therefore being used as a probe to screen the different halophyte cDNA libraries to isolate the full-length cDNAs by standard methods. We use the nucleic acid molecules obtained in this procedure in methods of producing transgenic host cells and plants as described above.

We have subcloned unique regions from AtNHX1, AtNHX2 and AtNHX3 isoforms into a prokaryotic expression vector (pGEX2TK, Pharmacia) for the production of recombinant GST-fusion proteins that are being used for the generation of isoform-specific polyclonal antibodies in rabbits. Briefly, sequence-specific oligonucleotides, with 5' BamHI (sense strand) and 3' EcoRI (antisense strand) flanking restriction sites, were used for PCR-mediated amplification of the unique (partial) coding regions from each isoform, and the digested PCR products were ligated into EcoRI/BamHI-digested pGEX2TK vector. pGEX2TK plasmids containing the inserts corresponding to each AtNHX isoform were sequenced on both strands to verify the fidelity of the PCR reaction and were used for expression and purification of the recombinant GST-fusion proteins in *E. coli* (BL21 pLysS) as per manufacturers instructions (Pharmacia). We follow an identical procedure to that described above to produce recombinant halophyte-PNHX GST-fusion protein in *E. coli*. Antibodies against the fusion proteins are produced in rabbits by standard procedures and their isoform-specificity are confirmed by western blotting using the different GST-fusion proteins. The antibodies are used in conjunction with subcellular membrane fractions (prepared from sucrose density gradients) (15) from various *Arabidopsis* and other plant tissues, preferably halophyte tissues and western blots to determine the subcellular localization of each $Na^+/H^+$ exchanger isoform. These localization studies assign functions to the various isoforms.

EXAMPLE 8

Biochemical Characterization and Functional Analysis of $Na^+/H^+$ Exchangers from Arabidopsis and Other Plants, Preferably Salt-Tolerant (Halophytes) Plants.

Biochemical characterization of the $Na^+/H^+$ exchanger isoforms is performed in (i) heterologous eukaryotic expression systems (baculovirus expression system in Sf9 insect cells, transgenic yeast); and in (ii) transgenic plants.

The use of heterologous expression systems allows the fast characterization of the kinetic properties of each exchanger isoform ($K_m$, $V_{max}$, ion specificity). Baculovirus-infected Sf9 cells have proven to be a useful and adaptable system for high-level expression of correctly folded eukaryotic membrane proteins, thus they are an ideal tool for the study of membrane-bound proteins. The large size of the cells, combined with the relatively short time needed for the expression of the foreign plasma membrane-bound proteins (3–4 days) provides an excellent experimental system for the application of isotope exchange techniques. For expression in Sf9 insect cells, the Invitrogen baculovirus Sf9 insect cell system is used. Expression vector constructs (pBluBac4.5, Invitrogen) encoding full-length AtNHX exchanger proteins are prepared for each AtNHX and other PNHX isoforms using a PCR-based subcloning approach similar to that described above for the generation of GST-fusion proteins. Initially, the suitability of the insect cell expression system for uptake analysis is performed using a single AtNHX isoform. The other PNHX isoforms are studied in a similar manner. Cultures of Sf9 insect cells are infected with baculovirus containing expression vector constructs encoding the different PNHX isoforms. Infection and selection of transformants are performed as per manufacturer's instructions (Invitrogen). The isoform-specific antibodies described above aid in the assessment of recombinant protein expression and localization within the insect cells.

Equally important is the use of transgenic yeast as a tool for the expression of recombinant eukaryotic proteins, particularly because of post-translational modifications and targeting to endomembranes. In addition, functional complementation of yeast mutant strains with plant proteins is often possible. We have subcloned the AtNHX1 cDNA into a yeast expression vector (pYES2) using a PCR-based approach as described above. Yeast (strain w303a) have been transformed with this construct and expression of the recombinant plant protein is confirmed once the antiserum is available. In addition, salt-tolerance of transformed yeast is assessed for each AtNHX isoform by comparing growth rates at different NaCl concentrations. Methods for the isolation of transport-competent plasma membranes and tonoplast and the isolation of intact vacuoles are performed. The kinetics of $H^+/Na^+$ exchange is measured in intact insect cells and yeast, intact yeast vacuoles, and isolated plasma membranes and tonoplast vesicles according to known methods. $Na^+$ influx in intact cells is monitored by isotopic exchange using ($22Na^+$)Cl and fast-filtration techniques (17,i,ii). Kinetics of $H^+$-dependent $Na^+$ fluxes in vesicles is monitored by following the pH-dependent fluorescent quench of acridine dyes (13, 17).

The results of these kinetic characterization studies provides information about the ion specificity, affinity, and optimal activity conditions for each AtNHX isoform. We assign the activity of each isoform to the corresponding target membrane, and we also determine which of the isoforms have a higher affinity for sodium. We characterize the mechanisms of salt tolerance in general and tissue-specificity and developmental expression in particular.

In transgenic plants, expression of the different $Na^+/H^+$ antiports is verified with western blots using the isoform-specific antibodies described above. The kinetics of $H^+/Na^+$ exchange is measured in intact vacuoles, isolated plasma membranes and tonoplast vesicles (from roots and leaves) as described above.

EXAMPLE 9
Identification of Positive and Negative Regulators of $Na^+/H^+$ Antiport Activity.

Heterologous expression of plant transport molecules in *Saccharomyces cerevisiae* has been used successfully in recent years in numerous studies. The availability of yeast mutants with salt-sensitive phenotypes (generated by 'knock-outs' of sodium transport molecules such as $\Delta$ena1–4- the plasma membrane $Na^+$-ATPase pumps) makes it an especially suitable system for the study of sodium transport molecules. This heterologous expression facilitates kinetic studies of the antiport activity in yeast cells using radiolabelled $^{22}Na^+$.

Successful suppression of yeast mutants, incapable of sodium detoxification allows for the genetic identification of positive and negative regulators of these $Na^+/H^+$ antiports. Mutant yeast cells having a suppressed phenotype as a result of the expression of a plant $Na^+/H^+$ antiport are transformed with an Arabidopsis cDNA library for the purpose of identifying particular regulators of these antiport molecules. A phenotype of increased sodium tolerance in yeast identifies particular positive regulators of the antiport activity while negative regulators are identified by a phenotype of decreased sodium tolerance. These phenotypes depend on the co-expression of the particular cDNAs identified along with that of the $Na^+/H^+$ antiport under investigation. Identification of essential amino acid residues regulating the activity of $Na^+/H^+$ exchanger molecules is investigated by random mutagenesis of the antiport molecule which is achieved by PCR using a commercially available low fidelity Taq enzyme. The constructs generated are used in transforming sodium-related yeast mutants to identify particular $Na^+/H^+$ antiport residues that affect suppression of the mutant yeast phenotype. Both gain-of-function and loss-of-function mutations are examined and mapped to the particular mutant residue by sequencing. Gain-of-function mutations are of particular interest since they represent constitutive activation of the antiport activity allowing for increased sodium detoxification.

EXAMPLE 10
Transformation of *Arabidopsis thaliana* Using Overexpression of Different Putative Isoforms and Antiports from Other Plants, Preferably Salt Tolerant Plants and Evaluation of Salt-Tolerance.

*Arabidopsis* represents a readily transformable model organism with the particular advantage of having a short generation time. *Agrobacterium tumefaciens*-mediated genetic transformation is utilized for *Arabidopsis* (ecotype Columbia). Studies include the overexpression of PNHX transgenes in a wild-type background, combined overexpression of more than one PNHX transgene, and suppression of endogenous PNHX expression using antisense PNHX expression. Stable transformation of progeny is confirmed by Southern blotting. Overexpression of transgenes, or suppression of expression using antisense constructs, is confirmed by Northern and western blotting. In all cases, salt-tolerance of transgenic plants is compared to wild-type plants, and control plants transformed with empty transformation vectors. Separate transformations are performed on *Arabidopsis* plants using expression vector constructs for each of the different AtNHX isoforms. In addition, *Arabidopsis* plants are transformed with PNHX genes from other plants, preferably salt tolerant plants in order to assess the effect on salt tolerance of the expression of a $Na^+/H^+$ exchanger in a glycophytic plant.

For overexpression studies, full-length AtNHX1, AtNHX2, AtNHX3 and AtNHX4 cDNAs are subcloned in a sense orientation into the expression vector containing a "superpromoter" (20). A PCR based subcloning strategy is used for each AtNHX cDNA as described above for the production of NHXGST-fusion constructs. For the production of vector constructs containing PNHX cDNAs in an antisense orientation, oligonucleotides with SalI and SacI restriction sites flanking the C-terminal and N-terminal PNHX regions respectively, are used for PCR amplification. All plasmid constructs are sequenced on both strands to confirm the fidelity of the PCR amplification before transformation of *Agrobacterium tumefaciens* (strain LBA4404). For each PNHX-pBISN1 construct, approximately 1 L of *Agrobacterium* culture, grown under antibiotic selection at 28° C., is used for the transformation of *Arabidopsis*. Plants are ready for transformation when primary bolts are approximately 15 cm. About 2 flats of plants (~80 plants per flat) are used per transformation. A highly efficient, vacuum-less infiltration transformation method (iii) is used. Harvested *Agrobacterium* cultures are resuspended in an infiltration media containing a mild surfactant (Silwet L-77, Lehle Seeds), and each pot of *Arabidopsis* is simply submerged in the *Agrobacterium* for 2–6 minutes. Plants are thereafter drained, and returned to the growth chamber until the seeds are ready for harvesting (about 4 weeks). Seeds (T1 generation) are collected and after surface sterilization, are plated on sterile, selective media containing kanamycin, vernalized, and then grown under optimal conditions. Healthy seedlings showing kanamycin resistence after about 7 days are transplanted to soil and the presence of the transgene confirmed by Southern blotting. Seeds from T1 transformants (ie T2 generation) are harvested, sown, and T2 plants used for Northern and western blotting to determine the expression patterns of the transgenes and PNHX proteins. Representative transgenic lines (e.g. showing low, medium, or high transgene expression) is used for studies of salt-tolerance. A similar approach is used for transformation of *Arabidopsis* with the PNHXs from other plants.

Salt tolerance is assessed by measuring the growth rate of the plants at increasing salt concentrations. Plant biomass, root/shoot ratios, tissue ion content is measured. Root and hypocotyl growth rates is measured and correlated with tissue water content of plants growing at different NaCl concentrations.

EXAMPLE 11
Transformation of Crop Plants with *A. thaliana* and/or Other Exchangers Under Constitutive and Inducible Promoters and Evaluation of Salt-Tolerance.
a) *Agrobacterium tumefaciens*-Mediated Transformation of Crop Plants We assess whether or not homologues of the AtNHX genes exist in the plant of choice. We use degenerate oligonucleotide PCR-primers (as described for other plants) and a cDNA library to isolate the full-length cDNA. The high efficiency *Agrobacterium*-mediated transformation method developed specifically for *Brassica* by Moloney et al (iv) is used to introduce and overexpress foreign nucleic acid molecules and/or overexpress the endogenous PNHX nucleic acid molecule in the crop plant(s). This method takes advantage of the fact that cut cotyledonary petioles from, which are capable of undergoing organogenesis (ie generating explants), are very susceptible to *Agrobacterium* infection. Shortly after germination (~5 days) cotyledons are excised and imbedded into Murashige-Skoog medium (Gibco) enriched with benyzladenine. Expression vector constructs are prepared using a PCR-based subcloning approach as described above using the pCGN5059 binary plasmid (which employs the CaMV $^{35}$S promoter to drive constitutively high expression) engineered for gentamycin resistance (iv) and cDNAs of the various AtNHX clones and/or the halophyte PNHX clones, and the choosen plant PNHX clones. Excised cotyledons are infected with *Agrobacterium* cultures (strain EHA101), containing the vector construct of interest, by brief dipping and then co-cultivated with the *Agrobacterium* for a 72 h. Subsequently, cotyledons are transferred to regeneration medium containing gentamycin as the selective agent. After explant regeneration, and subculturing, on selective media (~4 weeks) explants are transferred to rooting medium and then into soil once a root mass has developed. Tissue samples are examined from growing plants to confirm transgene presence by Southern blotting as described above for the transformation of *Arabidopsis*. Transformed plants (T1 generation) are allowed to flower and set seed and these seeds are germinated (T2) under selective conditions and transformants used for expression analysis of the transgenes and evaluation of salt-tolerance as described above. Also, biochemical analysis of the plants is performed. These include, Na$^+$/K$^+$ ratios, sugar, amino acid and quaternary N-compounds. Salt-tolerance is also evaluated in fields trials.
b) Microprojectile Bombardment-Mediated Transformation of Crop Plants.

A microprojectile bombardment-mediated transformation of crop plants is used when *Agrobacterium tumefaciens*-mediated transformation is not successful. We assess whether or not homologues of the AtNHX genes exist in the plant of choice. We use degenerate oligonucleotide PCR-primers (as described above) and a cDNA library to isolate the full-length cDNA. Expression vector constructs, using the pBAR vector for high level expression of AtNHX or the halophyte PNHX or the endogenous PNHX from the plant of choice, are used in conjunction with the microprojectile bombardment system as described by Tomes et al. (v). Bombardment procedures is carried out in callus tissue. Plant calli are initiated by culturing immature embryos on Callus medium (vi). After about 2 weeks, friable calli that are growing rapidly are subcultured and grown for an additional 2 weeks and then used for transformation. Calli for transformation are transferred to fresh medium, incubated for 24 h and bombarded with tungsten microprojectiles carrying the pBARNHX vector construct. Bombardment conditions is performed according to manufacturers instructions. Calli that show visible growth 10 days after bombardment are transferred to selective media (containing either Bialaphos or Ignite) in order to identify putative transformants. The growth of transformed plant calli on this selective media is continued for 34 months. Each putative stable transgenic event becomes apparent as a mass of friable embyogenic callus growing in the presence of the selection agent. Stable transformation is verified by Southern blots. Selected calli are transferred onto a regeneration medium (v), kept in the dark at 28° C. for 7 days and then transferred to growth chambers under a 16-h photoperiod until green shoots appear. Plantlets (1–2 cm long) are transferred to individual tubes containing germination medium to allow continued development. At the three to four leaf stage, plants are transferred to soil and into the greenhouse. At the eight-leaf stage, these plants are sprayed with 1% (w/v) Ignite herbicide to detect the presence of the BAR gene. This herbicide kills those plants not carrying the BAR gene. Confirmed transgenic plants (T1) are allowed to mature, flower, set seed, and seeds used for the production of T2 plants. Transgenic T2 plants are used for the evaluation of salt-tolerance as described above. Transgenic T2 and T3 plants are used in field trials for the evaluation of salt tolerance.
Methods Cloning of the *Arabidopsis* Na$^+$/H$^+$ Antiport cDNA (AtNHX1)

The full-length cDNA of AtNHX1 was cloned by us from an *Arabidopisis thaliana* (Columbia) seedling cDNA library (38). The library was initially screened with an EST (GenBank # T75860; FIG. 8(*h*)) obtained from the *Arabidopsis* Biological Resource Center (ABRC) that showed homology to *Arabidopsis* genomic sequence (A-TM021B04.4). The invention includes nucleic acid molecules of between about: 500–1000, 1000–1500 1500–1600, 1600–1700, 1700–2000 or 2000–2500 or greater than 2500 nucleotides including the EST sequence (or a sequence having at least about: 35, 35, 55, 65, 75, 85, 90, 95, 99, 99.5 sequence identity to the EST sequence or the polypeptide encoded by the EST sequence) and which encodes a polypeptide that extrudes monovalent (preferably potassium ions or lithium ions, most preferably sodium ions) out of the cytosol for preparation of transgenic plants and host cells, and in the other methods of the invention described below. These sequences are useful in the methods of the invention described above (for example as a probe, research uses, hybridization). The *Arabidopsis* genomic sequence predicted a polypeptide of 457 amino acids. Plaques that hybridized with the labeled EST probe were subjected to a secondary screen using the PCR product from the nested amplification of a region coding for the N-terminal portion of the predicted polypeptide. The forward primer, based on the predicted start codon of the polypeptide (Primer-NT), 5-GCCATGTTGGATTCTCTAGTGTCG-3 SEQ ID NO:11 and the reverse primer, based on the stop codon predicted from the EST (Primer-CT), 5'-CCGAATTCTCAAAGCTTTTCTTCCACG-3' SEQ ID NO:12, were used to amplify a 1.7 kb product from the seedling library. This product was purified by agarose gel electrophoresis and used as the template for a second amplification using primer-NT and a reverse primer (primer-C) based on the genomic sequence, 5'-CGGAATTCACAGAAAAACACAGTGAGGAT-3' SEQ ID NO:13. The resulting 900 bp fragment served as the template for the probe used in the secondary screen. The pure plaques obtained in the secondary screen were tested by PCR using the primer-NT, primer CT combination. Three of the plaques, from which a 1.7 kb product was amplified, were selected for excision of the phagemid. Single colonies containing the excised phagemid were grown in liquid culture. Aliquots of each of these cultures were used as templates for the PCR amplification of the region bound by the library plasmid to the 5' side of the clone (T3 promoter) and the reverse primer C. In one clone, a 1.2 kb fragment was amplified, which implied that the clone had an upstream untranslated region of approximately 300 bp. This clone was selected for complete sequencing.

Cloning of the *Arabidopsis* AtNHX2 Na$^+$/H$^+$ antiport cDNA

The full-length AtNHX2 cDNA was cloned from an *Arabidopsis thaliana* (Columbia) seedling cDNA library. PCR primers were designed for the amplification of the AtNHX2 sequence based on a BAC DNA sequence (MTE17) with a predicted amino acid sequence showing homology to AtNHX1. The forward primer (X6F), 5'-CCTCAGGTGATACCAATCTCA-3' SEQ ID NO:32 and the reverse primer (X6REV), 5'-GATCCAATGTAACACCGGAG-3' SEQ ID NO:33 were used to amplify a 1.2 kb product from the seedling library by PCR. This product was purified by agarose gel electrophoresis and used as a probe in hybridization screening of the seedling cDNA library. Plaques that hybridized with the labeled probe were subjected to a secondary screen using the 1.2 kb PCR product as a probe. Pure plaques obtained in the secondary screen were tested by PCR using primer-X6F, primer-X6REV combination. Only one of the plaques had the 1.2 kb product amplified from it. This plaque was used for excision of the phagemid. This clone was used for complete sequencing.

Cloning of the *Arabidopsis* AtNHX3 and AtNHX4 Na$^+$/H$^+$ antiport cDNAs

Full length AtNHX3 and AtNHX4 cDNAs were cloned by us from an *Arabidopsis thaliana* (Columbia) seedling cDNA libraries (CD4-15 and CD4-16; *Arabidopsis* Stock Center, Columbus, Ohio). PCR primers were designed for the amplification of a genomic sequence based on a BAC DNA sequence (F20D21) with a predicted amino acid sequence showing homology to both AtNHX1 and AtNHX2. The forward primer (NHX7F), 5'-TTCGTTCTCGGCCATGTCC-3' SEQ ID NO:34 and the reverse primer (NHX7REV), 5'-CGGAGAGACCAACACCTTCTGC-3' SEQ ID NO:35 were used to amplify a 2.2 kb product using *Arabidopsis thaliana* (Columbia) genomic DNA as a template. This product was purified by agarose gel electrophoresis and used as a probe in hybridization screening of the seedling cDNA libraries. Plaques that hybridized with the labeled probe were subjected to a secondary screen using the 2.2 kb PCR product as a probe. Pure plaques were used as templates for the PCR amplification of the region bound by the library plasmid using the T3 and T7 promoter sequences as primers. Two independent clones (insert sizes of 1.7 kb and 2.1 kb) were selected for phagemid excision and complete sequencing.

Southern Blot Analysis

Genomic DNA was isolated from mature leaf tissue of *Arabidopsis thaliana* (Columbia). 10 ug of this genomic DNA was digested with ClaI, EcoRI, XbaI, or HindIII, fractionated on 0.7% agarose gel, and transferred to Hybond N$^+$ membrane (Amersham) according to manufacturers instructions. Overnight hybridization was performed at 65° C. in Amersham hybridization buffer with AtNHX1 cDNA fragments labeled with $^{32}$P by the random priming method. The final wash was in 0.1×SSPE, 0.1% SDS at 65° C. Hybridization signals were detected by autoradiography on BioMax hyperfilm (Kodak).

Northern Blot Analysis

*Arabidopsis thaliana* ecotype Columbia was grown either on vertical plates on medium containing 0.5×MS salts and 1% agar at 20–25° C. under continuous fluorescent light for 1.5 weeks or in soil at 20–25° C. under fluorescent light and incandescent light with a 14 hour photo period for 3–4 weeks. Total RNA was isolated from flower, leaf, and inflorescence stems of the mature plants and from root and shoot tissues of the vertically grown seedlings using TRI-ZOL reagent (GibcoBRL). 40 ug of RNA was electrophoresed and transferred to Hybond No membrane (Amersham) according to manufacturers instructions. Methylene blue was used to visualize the 26S and 18S ribosomal RNA for quantitation. The blotted RNA was hybridized and washed as described for the southern blot analysis.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

Generation of Transgenic *Arabidopsis* Plants Overexpression AtNHX1

An AtNHX1 PCR product was amplified using Vent DNA polymerase (New England Biolabs) with the following primers (SE-ATX1-SalI 5'-CGCGTCGACATGTTGGATTCTCTAGTGTCG-3' SEQ ID NO:37 and ATXCT2 5'-CCGAATTCTCAAAGCTTTTCTTCCACG-3' SEQ ID NO:12). This product was digested with SalI gel purified and used in a ligation reaction along with pBISNI prevously digested with SalI and SmaI and gel purified. The resulting vector pBISNI-AtNHX1 contained the AtNHX1 open reading frame in a sense orientation under the control of the super promoter.

Overexpression constructs carrying the AtNHX1 cDNA are introduced into an electro-competent *Agrobacterium tumefaciens* (LBA4404) by electroporation. The *Agrobacteria* are plated on LB plates containing 50 mg/L kanamycin and grown for ~2 days at 30° C. to select for bacteria carrying the overexpression constructs. One liter liquid LB+kanamycin (50 mg/L) is inoculated with a single *Agrobacterium* colony selected from the LB (kanamycin 50 mg/L) plates. The culture is grown to a minimum of OD=1 (600 nm) for 2–3 days. The *Agrobacteria* are then pelleted and resuspended in 1 L infiltration medium (IM –0.5×MS salts; 0.5 g/L MES; 5% sucrose; 0.03% Silwet L-77). Flowering *Arabidopsis* plants with primary bolts reaching ~15 cm are used for the transformation procedure (T1). Pots of *Arabidopsis* plants are dunked into the 1M solution containing the *Agrobacteria* and left submerged for 2–6 minutes. The same procedure can be repeated after 8–12 days on the same plants. Plants are allowed to senesce, the plants are dried thoroughly and the seeds harvested. Seeds are plated on agar plates containing 25 mg/L kanamycin in a medium containing MS salts, 0.8% (w/v) agar adjusted to pH 6.0 with KOH. The plates are transferred to a growth room at 25° C. under continuous light. After 10 days the kanamycin-resistant seedlings (T2) are transferred to small pots containing vermiculite. At senescence (~8 weeks) the seeds are collected from single plants and plated on agar plates containing MS salts and 25 mg/L kanamycin. After 10 days the kanamycin-resistant seedlings (T3) are transferred to small pots containing vermiculite. Seeds produced by these plants are germinated and used to assess salt tolerance of the transgenic plants.

Assessment of Salt Tolerance in Transgenic Plants

This procedure is described in the legend for FIG. 7.

The present invention has been described in detail and with particular reference to the preferred embodiments; however, it will be understood by one having ordinary skill in the art that changes can be made thereto without departing from the spirit and scope of the invention.

All articles, patents and other documents described in this application (including Genbank sequences and/or accession numbers), U.S. application No. 60/078,474 (filed Mar. 18, 1998), U.S. application No. 60/116,111 (filed Jan. 15, 1998) and U.S. Pat. Nos. 5,612,191, 5,763,211, 5,750,848 and 5,681,714, are incorporated by reference in their entirety to the same extent as if each individual publication, patent or document was specifically and individually indicated to be incorporated by reference in its entirety. They are also incorporated to the extent that they supplement, explain, provide a background for, or teach methodology, techniques and/or compositions employed herein.

The patent or application file contains at least one drawing executed in color. Copies of this patent or patent application publication with color drawing(s) will be provided by the Office upon request and payment of the necessary fee.

TABLE 4

| Hybridization | Wash |
|---|---|
| High stringency (very similar sequences) | |
| 55–65° C. | 60–65° C. |
| 5 × SSC | 0.1 × SSC |
| 2% SDS | 0.1% SDS |
| 100 µg/ml SSDNA | |
| Intermediate stringency (similar sequences) (Moderate stringency) | |
| 40–50° C. | 50–50° C. |
| 5 × SSC | 0.1 × SSC |
| 2% SDS | 0.1% SDS |
| 100 µg/ml SSDNA | |
| Low stringency (low similarity among sequences, i.e. many sequences similar) | |
| 30–40° C. | 40–50° C. |
| 5 × SSC | 2 × SSC |
| 2% SDS | 0.2% SDS |
| 100 µg/ml SSDNA | |

Abbreviations:
SSC = sodium chloride-sodium citrate buffer
SSDNA = single stranded DNA

TABLE 5

List of Plants

| | |
|---|---|
| Alfalfa | Melon |
| Almond | Mustard |
| Apple | Oak |
| Apricot | Oat |
| *Arabidopsis* | Olive |
| Artichoke | Onion |
| Atriplex | Orange |
| Avocado | Pea |
| Barley | Peach |
| Beet | Pear |
| Birch | Pepper |
| Brassica | Pine |
| Cabbage | Plum |
| Cacao | Poplar |
| Cantaloup/cantalope | Potato |
| Carnations | Prune |
| Castorbean | Radish |
| Caulifower | Rape |
| Celery | Rice |
| Clover | Roses |
| Coffee | Rye |
| Corn | Sorghum |
| Cotton | Soybean |
| Cucumber | Spinach |
| Garlic | Squash |
| Grape | Strawberries |
| Grapefruit | Sunflower |
| Hemp | Sweet corn |
| Hops | Tobacco |
| Lettuce | Tomato |
| Maple | Wheat |

REFERENCES (1) Rush, P W and Epstein, E (1981). J. Amer. Soc. Hort. Sci. 106, 699–704.
(2) Norlyn, J D (1980). In: Genetic Engineering of Osmoregulation (Eds. D W Rains, R C Valentine and A Hollaender) pp. 293–309. Plenum Press: New York.
(3) Tal, M (1985). Plant & Soil 89, 199–226.
(4) Flowers, T J and Yeo, A R (1995). Aust. J. Plant Physiol. 22, 875–884.
(5) Bonhert, H J and Jensen, R G (1996). Aust J. Plant Physiol. 23, 661–667.
(6) Tarcynski, M C, Jensen, R G & Bonhert, H J. (1995) Science 259, 508–510.
(7) Kishor et al. (1995). Plant Physiol. 108, 1387–1394.
(8) Ishitani, M, et al., (1995). Plant Mol. Biol. 27, 307–317
(9) Xu, et al. (1996) Plant Physiol. 110, 249–257.
(10) Wu, R and Ho, T H D. Patent # WO9713843.
(11) Jia, Z P, et al., (1992). EMBO J. 11, 1631–1640.
(12) Young, PG & Zheng, P. J. Patent #WO9106651.
(13) Blumwald, E & Poole, R. J. (1985) Plant Physiol. 78, 163–167.
(14) Blumwald, E et al., (1987). Plant Physiol. 85, 30–33.
(15) Blumwald, E & Poole, R. J. (1987) Plant Physiol. 83, 884–887.
(16) Barkla, B J, et al., (1990). Plant Physiol. 93, 924–930.
(17) Barkla, B. J. & Blumwald, E. (1991) Proc. Natl. Acad. Sci. USA 88, 11777–11181.
(18) Blumwald, E. & Gelli, A. (1997). Adv. Bat. Res. 25, 401–417.
(19) Thompson, J D et al., Nucleic Acid Res. 22:4673–4680.
(20) Ni et al., (1995) Plant Journal 7:661–676
(21) Shah et al., (1986) Science 233:478–481.
(22) Ono et al., (1996) Plant Physiol 112:483–491
(23) Abe et al., (1997) Plant Cell 9:1859–1868.
(24) Rieping M and Schoffl F (1992) Mol Gen Genet 231:226–2321.

(25) Raghothama et al., (1997) Plant Mol Biol 34:393–402).
(26) Mett et al., (1996) Transgenic Res 5:105–113.
(27) Schena et al., (1991) PNAS 88:10421–10425.
(28) Vorst et al. (1990) Plant Mol Biol 14:491–499.
(29) Wanapu & Shinmyo (1996) Ann. NY Acad. Sci. 782:107–114.
(30) Harlow E & Lane D (1988). Antibodies: a laboratory manual. Cold Spring Harbor Laboratory Press. New York.
(31) Sambrook, J, Fritsch, E. E. & Maniatis, T. (1989). Molecular Cloning: A laboratory manual. Cold Spring Harbor Laboratory Press. New York.
(32) Lee, C. C. & Caskey, T. in: PCR Protocols: A guide to Methods and Applications. Academic Press, Inc. San Diego. pp.46–53
(33) Narasimhulu, S B, et al., Plant Cell 8:873–886 (1996))
(34) McCormac A C. et al., (1997) Mol Biotechnol. 8:199–213.
(35) Ma H, et al., (1987) Gene 58:202–226
(36) Gietz R D & Woods, R A (1994). High efficiency transformation with lithium acetate. In Molecular Genetics of Yeast, A Practical Approach (J. Johnston, ed.) New York: IRL Press. pp.121–134.
(37) Gietz, R D & Sugino, A (1988), Gene 74: 527–534.
(38) Krieber et al. (1993) Cell 72:427–441.
(i) Blumwald, E. (1987). Physiol. Plant 69, 731–734.
(ii) Blumwald, E. & Poole, R. J. (1986). Plant Physiol. 80,727–731.
(iii) Clough, M. & Bent, A. (1997). *Arabidopsis* Meeting, Madison, Wis.,
(iv) Moloney, M. M., Walker, J. M., & Sharma, K. K. (1989). Plant Cell Rep. 8, 23B-242.
(v) Tomes, D. T., Ross, M. C., & Songstad, D. D. (1995). In: Plant Cell, Tissue and Organ Culture (O. L. Gamborg & G. C. Phillips, eds). Springer, New York. pp 197–213.
(vi) Amstrong, C. L., & Green, C. E. (1985). Planta 164, 207–214.

What is claimed is:

1. A transgenic plant comprising a construct comprising a plant promoter operably linked to a recombinant nucleic acid molecule encoding a polypeptide having Na+/H+ transporter activity that provides increased salt tolerance in a cell, wherein said nucleic acid molecule is selected from the group consisting of:

(a) the nucleic acid molecule shown in SEQ ID NO:1, or a complement thereof;

(b) a nucleic acid molecule encoding SEQ ID NO:2; and (c) a nucleic acid molecule encoding an amino acid sequence at least 95% identical to the amino acid sequence shown in SEQ ID NO:2.

2. The transgenic plant of claim 1, wherein the polypeptide having Na+/H+ transporter activity comprises an AtNHX transporter polypeptide.

3. The transgenic plant of claim 1, wherein the promoter is a constitutive promoter or an inducible promoter.

4. The transgenic plant of claim 1, wherein the polypeptide having Na+/H+ transporter activity extrudes monovalent cations into a vacuole of said plant.

5. An expression transgene comprising a recombinant nucleic acid molecule encoding a polypeptide having Na$^+$/H+ transporter activity that provides increased salt tolerance in a cell operably linked to a promoter selected from the group consisting of a super promoter, a $^{35}$S promoter of cauliflower mosaic virus, a drought-inducible promoter, an ABA-inducible promoter, a heat shock-inducible promoter, a salt-inducible promoter, a copper-inducible promoter, a steroid-inducible promoter and a tissue-specific promoter, wherein said nucleic acid molecule is selected from the group consisting of:

(a) The nucleic acid molecule shown in SEQ ID NO:1, or a complement thereof;

(b) a nucleic acid molecule encoding SEQ ID NO:2; and (c) a nucleic acid molecule encoding an amino acid sequence at least 95% identical to the amino acid sequence shown in SEQ ID NO:2.

6. A plant cell or a progeny thereof, wherein the plant cell, or the progeny thereof comprises the expression transgene of claim 5.

7. A plant, a plant part, a seed, a plant cell or a progeny thereof, wherein the plant, plant part, seed, plant cell, or progeny thereof comprises the expression transgene of claim 5.

8. The plant part of claim 7, comprising all or part of a leaf a flower, a stem, a root or a tuber.

9. The plant, plant part, seed or plant cell of claim 7, wherein the plant, plant part, seed or plant cell is of a species selected from the group consisting of alfalfa, almond, apple, apricot, *arabidopsis*, artichoke, *atriplex*, avocado, barley, beet, birch, *brassica*, cabbage, cacao, cantaloupe, carnations, castorbean, cauliflower, celery, clover, coffee, corn, cotton, cucumber, garlic, grape, grapefruit, hemp, hops, lettuce, maple, melon, mustard, oak, oat, olive, onion, orange, pea, peach, pear, pepper, pine, plum, poplar, potato, prune, radish, rape, rice, roses, rye, salicornia, sorghum, soybean, spinach, squash, strawberries, sunflower, sweet corn, tobacco, tomato and wheat.

10. The plant, plant part, seed or plant cell of claim 7, wherein the plant is a dicot plant.

11. The plant, plant part, seed or plant cell of claim 7, wherein the plant is a monocot plant.

12. A method for producing a recombinant plant cell that expresses a nucleic acid molecule, the method comprising introducing into a plant cell the expression transgene of claim 5.

13. A method of producing a genetically transformed plant which expresses PNHX transporter polypeptide, comprising regenerating a genetically transformed plant from the plant cell, seed or plant part of claim 7.

14. The method of claim 12, wherein the genome of the plant cell also comprises a functional PNHX gene.

15. The method of claim 12, wherein the genome of the plant cell does not comprise a functional PNHX gene.

16. A transgenic plant produced according to the method of claim 13.

17. A method for expressing a PNHX transporter polypeptide in the plant cell of claim 6, the method comprising culturing the plant cell under conditions suitable for gene expression, wherein the PNHX transporter polypeptide is expressed.

18. A method for producing a transgenic plant that expresses elevated levels of PNHX transporter polypeptide relative to a non-transgenic plant, comprising transforming a plant with the expression transgene of claim 5 such that the PNHX transporter polypeptide is expressed at elevated levels in the plant relative to a plant that has not been transformed with the expression transgene.

19. A method of producing a genetically transformed plant wherein the method comprises:
   (a) cloning or synthesizing a nucleic acid molecule encoding a polypeptide having Na+/H+ transporter activity that provides increased salt tolerance in a cell, wherein said nucleic acid molecule is selected from the group consisting of: (i) the nucleic acid molecule shown in SEQ ID NO:1, or a complement thereof; (ii) a nucleic acid molecule encoding SEQ ID NO:2; and (iii) a nucleic acid molecule encoding an amino acid sequence at least 95% identical to the amino acid sequence shown in SEQ ID NO:2, wherein said nucleic acid molecule encodes a polypeptide capable of providing salt tolerance to a plant;
   (b) inserting the nucleic acid molecule in a vector so that the nucleic acid molecule is operably linked to a promoter;
   (c) insert the vector into a plant cell or plant seed;
   (d) regenerating a plant from the plant cell or plant seed, wherein salt tolerance in the plant is increased compared to a wild type plant.

20. A transgenic plant produced according to the method of claim 19.

21. An isolated nucleic acid molecule encoding PNHX transporter polypeptide, wherein said polypeptide has Na+/H+ transporter activity that provides increased salt tolerance in a cell, wherein said nucleic acid comprises SEQ ID NO:1.

* * * * *

SEQUENCE LISTING

```
<160> NUMBER OF SEQ ID NOS: 37

<210> SEQ ID NO 1
<211> LENGTH: 2178
<212> TYPE: DNA
<213> ORGANISM: Arabidopsis thaliana
<220> FEATURE:
<221> NAME/KEY: CDS
<222> LOCATION: (286)..(1899)
<223> OTHER INFORMATION: Figure 1(a)

<400> SEQUENCE: 1
cctctctgtt tcgttcctcg tagacgaaga agaagaagaa tctcaggttt tagctttcga      60
agcttccaaa attttgaatt ttgatcttct gggctctttt gtaaatcaga ctgaagatat     120
ttagattacc cagaagttgt tcaaggaatg gtttcagtgg acagcacgga aagataaaag     180 agacttttt ttccagattt tgctgatcca aaatctgaat agttgttcat gttcttggat     240
caaatctgga aagaggaagt ttgttggatc tagaagaaga taaca atg ttg gat tct     297
                                                  Met Leu Asp Ser
                                                    1 cta gtg tcg aaa ctg cct tcg tta tcg aca tct gat cac gct tct gtg     345
Leu Val Ser Lys Leu Pro Ser Leu Ser Thr Ser Asp His Ala Ser Val
  5                  10                  15                  20 gtt gcg ttg aat ctc ttt gtt gca ctt ctt tgt gct tgt att gtt ctt     393
Val Ala Leu Asn Leu Phe Val Ala Leu Leu Cys Ala Cys Ile Val Leu
                 25                  30                  35 ggt cat ctt ttg gaa gag aat aga tgg atg aac gaa tcc atc acc gcc     441
Gly His Leu Leu Glu Glu Asn Arg Trp Met Asn Glu Ser Ile Thr Ala
             40                  45                  50 ttg ttg att ggg cta ggc act ggt gtt acc att ttg ttg att agt aaa     489
Leu Leu Ile Gly Leu Gly Thr Gly Val Thr Ile Leu Leu Ile Ser Lys
         55                  60                  65 gga aaa agc tcg cat ctt ctc gtc ttt agt gaa gat ctt ttc ttc ata     537
Gly Lys Ser Ser His Leu Leu Val Phe Ser Glu Asp Leu Phe Phe Ile
 70                  75                  80 tat ctt ttg cca ccc att ata ttc aat gca ggg ttt caa gta aaa aag     585
Tyr Leu Leu Pro Pro Ile Ile Phe Asn Ala Gly Phe Gln Val Lys Lys
 85                  90                  95                 100 aag cag ttt ttc cgc aat ttc gtg act att atg ctt ttt ggt gct gtt     633
Lys Gln Phe Phe Arg Asn Phe Val Thr Ile Met Leu Phe Gly Ala Val
                105                 110                 115
```

| | | |
|---|---|---|
| ggg act att att tct tgc aca atc ata tct cta ggt gta aca cag ttc<br>Gly Thr Ile Ile Ser Cys Thr Ile Ile Ser Leu Gly Val Thr Gln Phe<br>            120                    125                 130 | | 681 |
| ttt aag aag ttg gac att gga acc ttt gac ttg ggt gat tat ctt gct<br>Phe Lys Lys Leu Asp Ile Gly Thr Phe Asp Leu Gly Asp Tyr Leu Ala<br>            135                    140                 145 | | 729 |
| att ggt gcc ata ttt gct gca aca gat tca gta tgt aca ctg cag gtt<br>Ile Gly Ala Ile Phe Ala Ala Thr Asp Ser Val Cys Thr Leu Gln Val<br>150                    155                    160 | | 777 |
| ctg aat caa gac gag aca cct ttg ctt tac agt ctt gta ttc gga gag<br>Leu Asn Gln Asp Glu Thr Pro Leu Leu Tyr Ser Leu Val Phe Gly Glu<br>165                    170                    175               180 | | 825 |
| ggt gtt gtg aat gat gca acg tca gtt gtg gtc ttc aac gcg att cag<br>Gly Val Val Asn Asp Ala Thr Ser Val Val Val Phe Asn Ala Ile Gln<br>                    185                    190               195 | | 873 |
| agc ttt gat ctc act cac cta aac cac gaa gct gct ttt cat ctt ctt<br>Ser Phe Asp Leu Thr His Leu Asn His Glu Ala Ala Phe His Leu Leu<br>            200                    205                 210 | | 921 |
| gga aac ttc ttg tat ttg ttt ctc cta agt acc ttg ctt ggt gct gca<br>Gly Asn Phe Leu Tyr Leu Phe Leu Leu Ser Thr Leu Leu Gly Ala Ala<br>                    215                    220               225 | | 969 |
| acc ggt ctg ata agt gcg tat gtt atc aag aag cta tac ttt gga agg<br>Thr Gly Leu Ile Ser Ala Tyr Val Ile Lys Lys Leu Tyr Phe Gly Arg<br>230                    235                    240 | | 1017 |
| cac tca act gac cga gag gtt gcc ctt atg atg ctt atg gcg tat ctt<br>His Ser Thr Asp Arg Glu Val Ala Leu Met Met Leu Met Ala Tyr Leu<br>245                    250                    255               260 | | 1065 |
| tct tat atg ctt gct gag ctt ttc gac ttg agc ggt atc ctc act gtg<br>Ser Tyr Met Leu Ala Glu Leu Phe Asp Leu Ser Gly Ile Leu Thr Val<br>                    265                    270               275 | | 1113 |
| ttt ttc tgt ggt att gtg atg tcc cat tac aca tgg cac aat gta acg<br>Phe Phe Cys Gly Ile Val Met Ser His Tyr Thr Trp His Asn Val Thr<br>            280                    285                 290 | | 1161 |
| gag agc tca aga ata aca aca aag cat acc ttt gca act ttg tca ttt<br>Glu Ser Ser Arg Ile Thr Thr Lys His Thr Phe Ala Thr Leu Ser Phe<br>                    295                    300               305 | | 1209 |
| ctt gcg gag aca ttt att ttc ttg tat gtt gga atg gat gcc ttg gac<br>Leu Ala Glu Thr Phe Ile Phe Leu Tyr Val Gly Met Asp Ala Leu Asp<br>310                    315                    320 | | 1257 |
| att gac aag tgg aga tcc gtg agt gac aca ccg gga aca tcg atc gca<br>Ile Asp Lys Trp Arg Ser Val Ser Asp Thr Pro Gly Thr Ser Ile Ala<br>325                    330                    335               340 | | 1305 |
| gtg agc tca atc cta atg ggt ctg gtc atg gtt gga aga gca gcg ttc<br>Val Ser Ser Ile Leu Met Gly Leu Val Met Val Gly Arg Ala Ala Phe<br>                    345                    350               355 | | 1353 |
| gtc ttt ccg tta tcg ttt cta tct aac tta gcc aag aag aat caa agc<br>Val Phe Pro Leu Ser Phe Leu Ser Asn Leu Ala Lys Lys Asn Gln Ser<br>            360                    365                 370 | | 1401 |
| gag aaa atc aac ttt aac atg cag gtt gtg att tgg tgg tct ggt ctc<br>Glu Lys Ile Asn Phe Asn Met Gln Val Val Ile Trp Trp Ser Gly Leu<br>                    375                    380               385 | | 1449 |
| atg aga ggt gct gta tct atg gct ctt gca tac aac aag ttt aca agg<br>Met Arg Gly Ala Val Ser Met Ala Leu Ala Tyr Asn Lys Phe Thr Arg<br>390                    395                    400 | | 1497 |
| gcc ggg cac aca gat gta cgc ggg aat gca atc atg atc acg agt acg<br>Ala Gly His Thr Asp Val Arg Gly Asn Ala Ile Met Ile Thr Ser Thr<br>405                    410                    415               420 | | 1545 |
| ata act gtc tgt ctt ttt agc aca gtg gtg ttt ggt atg ctg acc aaa<br>Ile Thr Val Cys Leu Phe Ser Thr Val Val Phe Gly Met Leu Thr Lys | | 1593 |

-continued

```
                 425                 430                 435
cca ctc ata agc tac cta tta ccg cac cag aac gcc acc acg agc atg      1641
Pro Leu Ile Ser Tyr Leu Leu Pro His Gln Asn Ala Thr Thr Ser Met
            440                 445                 450 tta tct gat gac aac acc cca aaa tcc ata cat atc cct ttg ttg gac      1689
Leu Ser Asp Asp Asn Thr Pro Lys Ser Ile His Ile Pro Leu Leu Asp
            455                 460                 465 caa gac tcg ttc att gag cct tca ggg aac cac aat gtg cct cgg cct      1737
Gln Asp Ser Phe Ile Glu Pro Ser Gly Asn His Asn Val Pro Arg Pro
            470                 475                 480 gac agt ata cgt ggc ttc ttg aca cgg ccc act cga acc gtg cat tac      1785
Asp Ser Ile Arg Gly Phe Leu Thr Arg Pro Thr Arg Thr Val His Tyr
485                 490                 495                 500 tac tgg aga caa ttt gat gac tcc ttc atg cga ccc gtc ttt gga ggt      1833
Tyr Trp Arg Gln Phe Asp Asp Ser Phe Met Arg Pro Val Phe Gly Gly
                505                 510                 515 cgt ggc ttt gta ccc ttt gtt cca ggt tct cca act gag aga aac cct      1881
Arg Gly Phe Val Pro Phe Val Pro Gly Ser Pro Thr Glu Arg Asn Pro
            520                 525                 530 cct gat ctt agt aag gct tgagggtaac gtggaagaaa agctttgatt             1929
Pro Asp Leu Ser Lys Ala
            535 ttttttggta gaaagggtg attcaaatta tgcttttgtg taaattatcc atttgtaata     1989 ttgtttgtga ggacagaaat ctgtcctaac gttttgagag cagaaagcaa aacatggcaa    2049 ctttgaagtg tttgattgat gtatgtaatt atattcatat ttgttttgtt gtaacacaaa    2109 ctacacattt gtttatgttt tgaatttggt ttttgcttcg aaaaaaaaaa aaaaaaaaa     2169 aaaaaaaaa                                                            2178

<210> SEQ ID NO 2
<211> LENGTH: 538
<212> TYPE: PRT
<213> ORGANISM: Arabidopsis thaliana
<220> FEATURE:
<223> OTHER INFORMATION: Figure 1(a)

<400> SEQUENCE: 2

Met Leu Asp Ser Leu Val Ser Lys Leu Pro Ser Leu Ser Thr Ser Asp
 1               5                  10                  15

His Ala Ser Val Val Ala Leu Asn Leu Phe Val Ala Leu Leu Cys Ala
                20                  25                  30

Cys Ile Val Leu Gly His Leu Leu Glu Glu Asn Arg Trp Met Asn Glu
            35                  40                  45

Ser Ile Thr Ala Leu Leu Ile Gly Leu Gly Thr Gly Val Thr Ile Leu
        50                  55                  60

Leu Ile Ser Lys Gly Lys Ser Ser His Leu Leu Val Phe Ser Glu Asp
 65                  70                  75                  80

Leu Phe Phe Ile Tyr Leu Leu Pro Pro Ile Phe Asn Ala Gly Phe
                85                  90                  95

Gln Val Lys Lys Lys Gln Phe Phe Arg Asn Phe Val Thr Ile Met Leu
            100                 105                 110

Phe Gly Ala Val Gly Thr Ile Ile Ser Cys Thr Ile Ser Leu Gly
        115                 120                 125

Val Thr Gln Phe Phe Lys Lys Leu Asp Ile Gly Thr Phe Asp Leu Gly
130                 135                 140

Asp Tyr Leu Ala Ile Gly Ala Ile Phe Ala Ala Thr Asp Ser Val Cys
145                 150                 155                 160
```

-continued

```
Thr Leu Gln Val Leu Asn Gln Asp Glu Thr Pro Leu Leu Tyr Ser Leu
                165                 170                 175
Val Phe Gly Glu Gly Val Val Asn Asp Ala Thr Ser Val Val Val Phe
            180                 185                 190
Asn Ala Ile Gln Ser Phe Asp Leu Thr His Leu Asn His Glu Ala Ala
        195                 200                 205
Phe His Leu Leu Gly Asn Phe Leu Tyr Leu Phe Leu Leu Ser Thr Leu
    210                 215                 220
Leu Gly Ala Ala Thr Gly Leu Ile Ser Ala Tyr Val Ile Lys Lys Leu
225                 230                 235                 240
Tyr Phe Gly Arg His Ser Thr Asp Arg Glu Val Ala Leu Met Met Leu
                245                 250                 255
Met Ala Tyr Leu Ser Tyr Met Leu Ala Glu Leu Phe Asp Leu Ser Gly
            260                 265                 270
Ile Leu Thr Val Phe Phe Cys Gly Ile Val Met Ser His Tyr Thr Trp
        275                 280                 285
His Asn Val Thr Glu Ser Ser Arg Ile Thr Thr Lys His Thr Phe Ala
    290                 295                 300
Thr Leu Ser Phe Leu Ala Glu Thr Phe Ile Phe Leu Tyr Val Gly Met
305                 310                 315                 320
Asp Ala Leu Asp Ile Asp Lys Trp Arg Ser Val Ser Asp Thr Pro Gly
                325                 330                 335
Thr Ser Ile Ala Val Ser Ser Ile Leu Met Gly Leu Val Met Val Gly
            340                 345                 350
Arg Ala Ala Phe Val Phe Pro Leu Ser Phe Leu Ser Asn Leu Ala Lys
        355                 360                 365
Lys Asn Gln Ser Glu Lys Ile Asn Phe Asn Met Gln Val Val Ile Trp
    370                 375                 380
Trp Ser Gly Leu Met Arg Gly Ala Val Ser Met Ala Leu Ala Tyr Asn
385                 390                 395                 400
Lys Phe Thr Arg Ala Gly His Thr Asp Val Arg Gly Asn Ala Ile Met
                405                 410                 415
Ile Thr Ser Thr Ile Thr Val Cys Leu Phe Ser Thr Val Val Phe Gly
            420                 425                 430
Met Leu Thr Lys Pro Leu Ile Ser Tyr Leu Leu Pro His Gln Asn Ala
        435                 440                 445
Thr Thr Ser Met Leu Ser Asp Asp Asn Thr Pro Lys Ser Ile His Ile
    450                 455                 460
Pro Leu Leu Asp Gln Asp Ser Phe Ile Glu Pro Ser Gly Asn His Asn
465                 470                 475                 480
Val Pro Arg Pro Asp Ser Ile Arg Gly Phe Leu Thr Arg Pro Thr Arg
                485                 490                 495
Thr Val His Tyr Tyr Trp Arg Gln Phe Asp Asp Ser Phe Met Arg Pro
            500                 505                 510
Val Phe Gly Gly Arg Gly Phe Val Pro Phe Val Pro Gly Ser Pro Thr
        515                 520                 525
Glu Arg Asn Pro Pro Asp Leu Ser Lys Ala
    530                 535

<210> SEQ ID NO 3
<211> LENGTH: 1788
<212> TYPE: DNA
<213> ORGANISM: Arabidopsis thaliana
<220> FEATURE:
```

```
<221> NAME/KEY: CDS
<222> LOCATION: (61)..(1647)
<223> OTHER INFORMATION: Figure 1(b)

<400> SEQUENCE: 3
tcttcgtttg cgattggtgt tttcaaaatc gacgaaatcg aaaacattat cgagtgaaaa         60 atg agt atc gga tta aca gag ttt gtg acg aat aaa cta gca gct gag        108
Met Ser Ile Gly Leu Thr Glu Phe Val Thr Asn Lys Leu Ala Ala Glu
 1               5                  10                  15 cat cct cag gtg ata cca atc tca gtg ttc atc gcc att ctc tgt cta        156
His Pro Gln Val Ile Pro Ile Ser Val Phe Ile Ala Ile Leu Cys Leu
             20                  25                  30 tgt tta gtt atc ggc cac ttg ctt gaa gag aat cga tgg gtt aat gaa        204
Cys Leu Val Ile Gly His Leu Leu Glu Glu Asn Arg Trp Val Asn Glu
         35                  40                  45 tct att acc gcc att tta gta gga gca gca tca gga aca gtg atc tta        252
Ser Ile Thr Ala Ile Leu Val Gly Ala Ala Ser Gly Thr Val Ile Leu
     50                  55                  60 ctt att agt aaa gga aaa agt tca cat att ttg gtg ttt gat gaa gaa        300
Leu Ile Ser Lys Gly Lys Ser Ser His Ile Leu Val Phe Asp Glu Glu
 65                  70                  75                  80 ctc ttc ttc att tac ctt ctt cct cca ata atc ttc aat gct ggg ttc        348
Leu Phe Phe Ile Tyr Leu Leu Pro Pro Ile Ile Phe Asn Ala Gly Phe
                 85                  90                  95 caa gtt aag aaa aag aag ttt ttt cac aac ttt tta acc atc atg tcc        396
Gln Val Lys Lys Lys Lys Phe Phe His Asn Phe Leu Thr Ile Met Ser
            100                 105                 110 ttt ggt gtg att gga gtt ttc atc tcc act gtc att atc tcg ttt ggg        444
Phe Gly Val Ile Gly Val Phe Ile Ser Thr Val Ile Ile Ser Phe Gly
        115                 120                 125 act tgg tgg ctg ttt ccc aag ttg gga ttt aag ggg ttg agt gct aga        492
Thr Trp Trp Leu Phe Pro Lys Leu Gly Phe Lys Gly Leu Ser Ala Arg
    130                 135                 140 gac tat ctt gcc ata gga acg att ttc tca tca act gat act gtt tgc        540
Asp Tyr Leu Ala Ile Gly Thr Ile Phe Ser Ser Thr Asp Thr Val Cys
145                 150                 155                 160 act cta cag att ctc cat caa gat gaa aca cca ttg cta tac agc tta        588
Thr Leu Gln Ile Leu His Gln Asp Glu Thr Pro Leu Leu Tyr Ser Leu
                165                 170                 175 gtc ttt gga gaa gga gtg gtg aat gat gca acc tca gtt gta ctg ttc        636
Val Phe Gly Glu Gly Val Val Asn Asp Ala Thr Ser Val Val Leu Phe
            180                 185                 190 aac gcc gtg caa aag att caa ttt gaa agc cta acc ggt tgg acg gcg        684
Asn Ala Val Gln Lys Ile Gln Phe Glu Ser Leu Thr Gly Trp Thr Ala
        195                 200                 205 ctg caa gta ttt ggg aac ttt ttg tac ctc ttc tca aca agc aca ctt        732
Leu Gln Val Phe Gly Asn Phe Leu Tyr Leu Phe Ser Thr Ser Thr Leu
    210                 215                 220 ctc gga att ggt gtg ggg cta ata aca tct ttt gtt ctt aaa acc ttg        780
Leu Gly Ile Gly Val Gly Leu Ile Thr Ser Phe Val Leu Lys Thr Leu
225                 230                 235                 240 tat ttt gga aga cat tct act aca cgc gaa ctc gcc atc atg gtt cta        828
Tyr Phe Gly Arg His Ser Thr Thr Arg Glu Leu Ala Ile Met Val Leu
                245                 250                 255 atg gct tac ctt tca tat atg ttg gct gag ctc ttc tca tta agt gga        876
Met Ala Tyr Leu Ser Tyr Met Leu Ala Glu Leu Phe Ser Leu Ser Gly
            260                 265                 270 att ctt act gtt ttc ttc tgt ggt gtt tta atg tcg cat tat gca tca        924
Ile Leu Thr Val Phe Phe Cys Gly Val Leu Met Ser His Tyr Ala Ser
        275                 280                 285
```

-continued

```
tat aac gtg aca gag agc tca aga atc act tcc agg cat gta ttt gca      972
Tyr Asn Val Thr Glu Ser Ser Arg Ile Thr Ser Arg His Val Phe Ala
    290                 295                 300 atg ttg tcc ttt att gcg gag aca ttc ata ttt ctg tat gtt gga aca     1020
Met Leu Ser Phe Ile Ala Glu Thr Phe Ile Phe Leu Tyr Val Gly Thr
305                 310                 315                 320 gat gct ctt gat ttt aca aag tgg aag aca agc agc tta agc ttt ggg     1068
Asp Ala Leu Asp Phe Thr Lys Trp Lys Thr Ser Ser Leu Ser Phe Gly
                325                 330                 335 ggt act ctg ggt gtc tcc ggt gtc ata acc gca tta gta ttg ctt gga     1116
Gly Thr Leu Gly Val Ser Gly Val Ile Thr Ala Leu Val Leu Leu Gly
            340                 345                 350 cga gca gca ttt gtc ttt cca ctc tcg gtc tta aca aat ttc atg aac     1164
Arg Ala Ala Phe Val Phe Pro Leu Ser Val Leu Thr Asn Phe Met Asn
        355                 360                 365 agg cac act gaa aga aac gag tct atc aca ttt aag cat cag gtg atc     1212
Arg His Thr Glu Arg Asn Glu Ser Ile Thr Phe Lys His Gln Val Ile
    370                 375                 380 att tgg tgg gca ggt cta atg cga ggt gct gtc tca att gct ctg gct     1260
Ile Trp Trp Ala Gly Leu Met Arg Gly Ala Val Ser Ile Ala Leu Ala
385                 390                 395                 400 ttc aag cag ttc aca tac tcc ggt gtt aca ttg gat cct gtg aat gct     1308
Phe Lys Gln Phe Thr Tyr Ser Gly Val Thr Leu Asp Pro Val Asn Ala
                405                 410                 415 gcc atg gtc acc aac acc act atc gtt gtt ctc ttt act aca ctg gtc     1356
Ala Met Val Thr Asn Thr Thr Ile Val Val Leu Phe Thr Thr Leu Val
            420                 425                 430 ttt ggt ttc ctc aca aaa cca ctt gtg aat tat ctc ctt cct caa gat     1404
Phe Gly Phe Leu Thr Lys Pro Leu Val Asn Tyr Leu Leu Pro Gln Asp
        435                 440                 445 gca agt cac aac acc gga aat aga ggt aaa cgc act gag cca ggt tct     1452
Ala Ser His Asn Thr Gly Asn Arg Gly Lys Arg Thr Glu Pro Gly Ser
    450                 455                 460 ccg aaa gaa gat gcg aca ctt cct ctt ctt tcc ttt gac gag tct gct     1500
Pro Lys Glu Asp Ala Thr Leu Pro Leu Leu Ser Phe Asp Glu Ser Ala
465                 470                 475                 480 tcc acc aac ttc aat aga gct aga gat agt att tcc ctt ctg atg gaa     1548
Ser Thr Asn Phe Asn Arg Ala Arg Asp Ser Ile Ser Leu Leu Met Glu
                485                 490                 495 caa cct gtg tac acc atc cac cgc tac tgg aga aag ttt gac gac aca     1596
Gln Pro Val Tyr Thr Ile His Arg Tyr Trp Arg Lys Phe Asp Asp Thr
            500                 505                 510 tac atg agg cct atc ttc ggt gga cct cgt cga gaa aac caa cca gaa     1644
Tyr Met Arg Pro Ile Phe Gly Gly Pro Arg Arg Glu Asn Gln Pro Glu
        515                 520                 525 tgc tagaattgat ccgggttctc cgcggggaaa tcatgatgag ttagtttttt         1697
Cys ttatagtcaa gaaagtagga tagttggttt agctaaaaca gtttcttaaa gtttttgtta  1757
aatgtataca acaaggttct tctatatacg c                                  1788

<210> SEQ ID NO 4
<211> LENGTH: 529
<212> TYPE: PRT
<213> ORGANISM: Arabidopsis thaliana
<220> FEATURE:
<223> OTHER INFORMATION: Figure 1(b)

<400> SEQUENCE: 4

Met Ser Ile Gly Leu Thr Glu Phe Val Thr Asn Lys Leu Ala Ala Glu
```

```
  1               5                10               15
His Pro Gln Val Ile Pro Ile Ser Val Phe Ile Ala Ile Leu Cys Leu
                 20                25                30
Cys Leu Val Ile Gly His Leu Leu Glu Glu Asn Arg Trp Val Asn Glu
                 35                40                45
Ser Ile Thr Ala Ile Leu Val Gly Ala Ala Ser Gly Thr Val Ile Leu
                 50                55                60
Leu Ile Ser Lys Gly Lys Ser Ser His Ile Leu Val Phe Asp Glu Glu
 65                  70                75                80
Leu Phe Phe Ile Tyr Leu Leu Pro Pro Ile Ile Phe Asn Ala Gly Phe
                 85                90                95
Gln Val Lys Lys Lys Phe Phe His Asn Phe Leu Thr Ile Met Ser
                100               105               110
Phe Gly Val Ile Gly Val Phe Ile Ser Thr Val Ile Ile Ser Phe Gly
                115               120               125
Thr Trp Trp Leu Phe Pro Lys Leu Gly Phe Lys Gly Leu Ser Ala Arg
                130               135               140
Asp Tyr Leu Ala Ile Gly Thr Ile Phe Ser Ser Thr Asp Thr Val Cys
145                 150               155               160
Thr Leu Gln Ile Leu His Gln Asp Glu Thr Pro Leu Leu Tyr Ser Leu
                165               170               175
Val Phe Gly Glu Gly Val Val Asn Asp Ala Thr Ser Val Val Leu Phe
                180               185               190
Asn Ala Val Gln Lys Ile Gln Phe Glu Ser Leu Thr Gly Trp Thr Ala
                195               200               205
Leu Gln Val Phe Gly Asn Phe Leu Tyr Leu Phe Ser Thr Ser Thr Leu
                210               215               220
Leu Gly Ile Gly Val Gly Leu Ile Thr Ser Phe Val Leu Lys Thr Leu
225                 230               235               240
Tyr Phe Gly Arg His Ser Thr Thr Arg Glu Leu Ala Ile Met Val Leu
                245               250               255
Met Ala Tyr Leu Ser Tyr Met Leu Ala Glu Leu Phe Ser Leu Ser Gly
                260               265               270
Ile Leu Thr Val Phe Phe Cys Gly Val Leu Met Ser His Tyr Ala Ser
                275               280               285
Tyr Asn Val Thr Glu Ser Ser Arg Ile Thr Ser Arg His Val Phe Ala
                290               295               300
Met Leu Ser Phe Ile Ala Glu Thr Phe Ile Phe Leu Tyr Val Gly Thr
305                 310               315               320
Asp Ala Leu Asp Phe Thr Lys Trp Lys Thr Ser Ser Leu Ser Phe Gly
                325               330               335
Gly Thr Leu Gly Val Ser Gly Val Ile Thr Ala Leu Val Leu Leu Gly
                340               345               350
Arg Ala Ala Phe Val Phe Pro Leu Ser Val Leu Thr Asn Phe Met Asn
                355               360               365
Arg His Thr Glu Arg Asn Glu Ser Ile Thr Phe Lys His Gln Val Ile
                370               375               380
Ile Trp Trp Ala Gly Leu Met Arg Gly Ala Val Ser Ile Ala Leu Ala
385                 390               395               400
Phe Lys Gln Phe Thr Tyr Ser Gly Val Thr Leu Asp Pro Val Asn Ala
                405               410               415
Ala Met Val Thr Asn Thr Thr Ile Val Val Leu Phe Thr Thr Leu Val
                420               425               430
```

-continued

```
Phe Gly Phe Leu Thr Lys Pro Leu Val Asn Tyr Leu Leu Pro Gln Asp
        435                 440                 445

Ala Ser His Asn Thr Gly Asn Arg Gly Lys Arg Thr Glu Pro Gly Ser
    450                 455                 460

Pro Lys Glu Asp Ala Thr Leu Pro Leu Leu Ser Phe Asp Glu Ser Ala
465                 470                 475                 480

Ser Thr Asn Phe Asn Arg Ala Arg Asp Ser Ile Ser Leu Leu Met Glu
                485                 490                 495

Gln Pro Val Tyr Thr Ile His Arg Tyr Trp Arg Lys Phe Asp Asp Thr
            500                 505                 510

Tyr Met Arg Pro Ile Phe Gly Gly Pro Arg Arg Glu Asn Gln Pro Glu
            515                 520                 525

Cys
```

<210> SEQ ID NO 5
<211> LENGTH: 714
<212> TYPE: DNA
<213> ORGANISM: Arabidopsis thaliana
<220> FEATURE:
<221> NAME/KEY: CDS
<222> LOCATION: (55)..(612)
<223> OTHER INFORMATION: Figure 1(c)(i)

<400> SEQUENCE: 5

```
acaaaagctg gagctccacc gcggtggcgg ccgctctaga actagtggat cccc cgg       57
                                                            Arg
                                                             1 gct gca gga att cgc ggc cgc ctc ggc cat gtc ctc cgc cgt cat cga      105
Ala Ala Gly Ile Arg Gly Arg Leu Gly His Val Leu Arg Arg His Arg
        5                  10                  15 ttc cac tat ctt cct gaa gcc agc ggt tcg ctt ctc att ggt tta atc      153
Phe His Tyr Leu Pro Glu Ala Ser Gly Ser Leu Leu Ile Gly Leu Ile
     20                  25                  30 gtc ggt ata ctt gct aat atc tcc gat act gag act agc att agg acg      201
Val Gly Ile Leu Ala Asn Ile Ser Asp Thr Glu Thr Ser Ile Arg Thr
 35                  40                  45 tgg ttt aat ttc cac gaa gag ttc ttc ttc ttg ttt ttg ttg cct ccc      249
Trp Phe Asn Phe His Glu Glu Phe Phe Phe Leu Phe Leu Leu Pro Pro
 50                  55                  60                  65 atc ata ttc cag tca ggt ttc agt ctt caa cct aaa cca ttc ttt tct      297
Ile Ile Phe Gln Ser Gly Phe Ser Leu Gln Pro Lys Pro Phe Phe Ser
             70                  75                  80 aac ttt gga gcc att gtt acc ttt gct atc atc gga act ttt gtc gct      345
Asn Phe Gly Ala Ile Val Thr Phe Ala Ile Ile Gly Thr Phe Val Ala
         85                  90                  95 tca gtt gtt act ggt ggt ctg gtt tat ctt ggc ggc tct atg tat ctc      393
Ser Val Val Thr Gly Gly Leu Val Tyr Leu Gly Gly Ser Met Tyr Leu
        100                 105                 110 atg tat aaa ctt ccc ttt gtt gag tgt ctt atg ttt ggt gca ctt ata      441
Met Tyr Lys Leu Pro Phe Val Glu Cys Leu Met Phe Gly Ala Leu Ile
    115                 120                 125 tca gct acg gac cct gtc act gta ctc tct ata ttc cag gat gtg ggc      489
Ser Ala Thr Asp Pro Val Thr Val Leu Ser Ile Phe Gln Asp Val Gly
130                 135                 140                 145 acc gat gtt aac ctg tat gct ttg gtc ttt gga gaa tca gtt ctg aat      537
Thr Asp Val Asn Leu Tyr Ala Leu Val Phe Gly Glu Ser Val Leu Asn
                150                 155                 160 gat gct atg gca ata tca ttg tac aga aca atg tcc tta gta aac cgc      585
Asp Ala Met Ala Ile Ser Leu Tyr Arg Thr Met Ser Leu Val Asn Arg
```

```
                      165                 170                 175
cag tcc tcg tct ggg gaa cat ttt tca tggtggtgat caggtttttt          632
Gln Ser Ser Ser Gly Glu His Phe Ser
            180                 185 gagactttgc tggctcaatg tcgcagggt tggggttgga ttcacttcag cttaatatcc   692
tcctcgatcc tcctatttcc ta                                           714

<210> SEQ ID NO 6
<211> LENGTH: 186
<212> TYPE: PRT
<213> ORGANISM: Arabidopsis thaliana
<220> FEATURE:
<223> OTHER INFORMATION: Figure 1(c)(i)

<400> SEQUENCE: 6

Arg Ala Ala Gly Ile Arg Gly Arg Leu Gly His Val Leu Arg Arg His
1               5                   10                  15

Arg Phe His Tyr Leu Pro Glu Ala Ser Gly Ser Leu Leu Ile Gly Leu
            20                  25                  30

Ile Val Gly Ile Leu Ala Asn Ile Ser Asp Thr Glu Thr Ser Ile Arg
        35                  40                  45

Thr Trp Phe Asn Phe His Glu Glu Phe Phe Leu Phe Leu Leu Pro
    50                  55                  60

Pro Ile Ile Phe Gln Ser Gly Phe Ser Leu Gln Pro Lys Pro Phe Phe
65                  70                  75                  80

Ser Asn Phe Gly Ala Ile Val Thr Phe Ala Ile Ile Gly Thr Phe Val
                85                  90                  95

Ala Ser Val Val Thr Gly Gly Leu Val Tyr Leu Gly Gly Ser Met Tyr
            100                 105                 110

Leu Met Tyr Lys Leu Pro Phe Val Glu Cys Leu Met Phe Gly Ala Leu
        115                 120                 125

Ile Ser Ala Thr Asp Pro Val Thr Val Leu Ser Ile Phe Gln Asp Val
    130                 135                 140

Gly Thr Asp Val Asn Leu Tyr Ala Leu Val Phe Gly Glu Ser Val Leu
145                 150                 155                 160

Asn Asp Ala Met Ala Ile Ser Leu Tyr Arg Thr Met Ser Leu Val Asn
                165                 170                 175

Arg Gln Ser Ser Ser Gly Glu His Phe Ser
            180                 185

<210> SEQ ID NO 7
<211> LENGTH: 420
<212> TYPE: DNA
<213> ORGANISM: Arabidopsis thaliana
<220> FEATURE:
<221> NAME/KEY: CDS
<222> LOCATION: (52)..(393)
<223> OTHER INFORMATION: Figure 1(c)(ii)

<400> SEQUENCE: 7
ggacttcgag gggccatggca tttgcacttg cacttcaata cttcatgatc t acc aga   57
                                                          Thr Arg
                                                            1 ggt cac ggc cca atc atc ttt tac tgc acc aca act att gtt gtt gtc   105
Gly His Gly Pro Ile Ile Phe Tyr Cys Thr Thr Thr Ile Val Val Val
        5                   10                  15 acg gtt tta cta ata gga ggt tcg aca ggt aaa atg ttg gaa gct ttg   153
Thr Val Leu Leu Ile Gly Gly Ser Thr Gly Lys Met Leu Glu Ala Leu
        20                  25                  30
```

```
gaa gtt gta ggt gac gat ctt gat gac tcc atg tct gaa ggc ttt gaa    201
Glu Val Val Gly Asp Asp Leu Asp Asp Ser Met Ser Glu Gly Phe Glu
 35              40                  45                  50 gag agc gat cat cag tat gtc cct cct cct ttt agc att gga gct tca    249
Glu Ser Asp His Gln Tyr Val Pro Pro Pro Phe Ser Ile Gly Ala Ser
             55                  60                  65 tct gac gag gat aca tca tca tca gga agc agg ttc aag atg aag ctg    297
Ser Asp Glu Asp Thr Ser Ser Ser Gly Ser Arg Phe Lys Met Lys Leu
         70                  75                  80 aag gag ttt cac aaa acc act aca tca ttc acc gcg ttg gac aaa aac    345
Lys Glu Phe His Lys Thr Thr Thr Ser Phe Thr Ala Leu Asp Lys Asn
     85                  90                  95 ttt ctg act ccg ttc ttc aca act aat agt gga gat gga gat gga gat    393
Phe Leu Thr Pro Phe Phe Thr Thr Asn Ser Gly Asp Gly Asp Gly Asp
100                 105                 110 ggggagtagc atggaaaaga tgtgtat                                      420
```

```
<210> SEQ ID NO 8
<211> LENGTH: 114
<212> TYPE: PRT
<213> ORGANISM: Arabidopsis thaliana
<220> FEATURE:
<223> OTHER INFORMATION: Figure 1(c)(ii)

<400> SEQUENCE: 8

Thr Arg Gly His Gly Pro Ile Ile Phe Tyr Cys Thr Thr Thr Ile Val
 1               5                  10                  15

Val Val Thr Val Leu Leu Ile Gly Gly Ser Thr Gly Lys Met Leu Glu
             20                  25                  30

Ala Leu Glu Val Val Gly Asp Asp Leu Asp Asp Ser Met Ser Glu Gly
         35                  40                  45

Phe Glu Glu Ser Asp His Gln Tyr Val Pro Pro Pro Phe Ser Ile Gly
     50                  55                  60

Ala Ser Ser Asp Glu Asp Thr Ser Ser Ser Gly Ser Arg Phe Lys Met
 65                  70                  75                  80

Lys Leu Lys Glu Phe His Lys Thr Thr Thr Ser Phe Thr Ala Leu Asp
                 85                  90                  95

Lys Asn Phe Leu Thr Pro Phe Phe Thr Thr Asn Ser Gly Asp Gly Asp
            100                 105                 110

Gly Asp
```

```
<210> SEQ ID NO 9
<211> LENGTH: 2284
<212> TYPE: DNA
<213> ORGANISM: Arabidopsis thaliana
<220> FEATURE:
<223> OTHER INFORMATION: Figure 5(a) and (b)

<400> SEQUENCE: 9
ttcgcggccg cgtctctctc tatttccagt aaaaaatcga aatttcgtat aatttcctca     60
gtcccgtaat tttctccttt ttttttcttcc ccaattcctt caattttcga attcgcctct   120
ctgtttcgtt cctcgtagac gaagaagaag aagaatctca ggttttagct ttcgaagctt   180
ccaaaatttt gaattttgat cttctgggct cttttgtaaa tcagactgaa gatatttaga   240
ttacccagaa gttgttcaag gaatggtttc agtggacagc acggaaagat aaaagagact   300
tttttttcca gattttgctg atccaaaatc tgaatagttg ttcatgttct tggatcaaat   360
ctggaaagag gaagtttgtt ggatctagaa gaagataaca atgttggatt ctctagtgtc   420
```

-continued

```
gaaactgcct tcgttatcga catctgatca cgcttctgtg gttgcgttga atctctttgt      480
tgcacttctt tgtgcttgta ttgttcttgg tcatcttttg gaagagaata gatggatgaa      540
cgaatccatc accgccttgt tgattgggct aggcactggt gttaccattt tgttgattag      600
taaaggaaaa agctcgcatc ttctcgtctt tagtgaagat cttttcttca tatatctttt      660
gccacccatt atattcaatg cagggtttca agtaaaaaag aagcagtttt tccgcaattt      720
cgtgactatt atgctttttg gtgctgttgg gactattatt tcttgcacaa tcatatctct      780
aggtgtaaca cagttctttta agaagttgga cattggaacc tttgacttgg gtgattatct      840
tgctattggt gccatatttg ctgcaacaga ttcagtatgt acactgcagg ttctgaatca      900
agacgagaca cctttgcttt acagtcttgt attcggagag ggtgttgtga atgatgcaac      960
gtcagttgtg gtcttcaacg cgattcagag ctttgatctc actcacctaa accacgaagc    1020
tgcttttcat cttcttggaa acttcttgta ttttgtttctc ctaagtacct tgcttggtgc    1080
tgcaaccggt ctgataagtg cgtatgttat caagaagcta actttggaa ggcactcaac    1140
tgaccgagag gttgcccta tgatgcttat ggcgtatctt tcttatatgc ttgctgagct    1200
tttcgacttg agcggtatcc tcactgtgtt tttctgtggt attgtgatgt cccattacac    1260
atggcacaat gtaacggaga gctcaagaat aacaacaaag cataccttg caactttgtc    1320
atttcttgcg gagacatta ttttcttgta tgttggaatg gatgccttgg acattgacaa    1380
gtggagatcc gtgagtgaca caccgggaac atcgatcgca gtgagctcaa tcctaatggg    1440
tctggtcatg gttggaagag cagcgttcgt ctttccgtta tcgtttctat ctaacttagc    1500
caagaagaat caaagcgaga aaatcaactt taacatgcag gttgtgattt ggtggtctgg    1560
tctcatgaga ggtgctgtat ctatggctct tgcatacaac aagtttacaa gggccgggca    1620
cacagatgta cgcgggaatg caatcatgat cacgagtacg ataactgtct gtcttttag    1680
cacagtggtg tttggtatgc tgaccaaacc actcataagc tacctattac cgcaccagaa    1740
cgccaccacg agcatgttat ctgatgacaa caccccaaaa tccatacata tcctttgtt    1800
ggaccaagac tcgttcattg agccttcagg gaaccacaat gtgcctcggc ctgacagtat    1860
acgtggcttc ttgacacggc ccactcggaa ccgtgcatta ctaactggag acaatttgat    1920
gactcttttca tcgacccgt ctttggaggt cgtggcttg tacccttgt tccaggttct    1980
ccaactgaga gaaaccctcc tgatcttagt aaggcttgag ggtaacgtgg aagaaaagct    2040
ttgattttt ttggtagaaa agggtgattc aaattatgct tttgtgtaaa ttatccattt    2100
gtaatattgt ttgtgaggac agaaatctgt cctaacgttt tgagagcaga aagcaaaaca    2160
tggcaacttt gaagtgtttg attgatgtat gtaattatat tcatatttgt tttgttgtaa    2220
cacaaactac acatttgttt atgttttgaa tttggttttt gcttcgaaaa aaaaaaaaaa    2280
aaaa                                                                  2284
```

<210> SEQ ID NO 10
<211> LENGTH: 547
<212> TYPE: PRT
<213> ORGANISM: Arabidopsis thaliana
<220> FEATURE:
<223> OTHER INFORMATION: Figure 5(a)and (b)

<400> SEQUENCE: 10

```
Met Leu Asp Ser Leu Val Ser Lys Leu Pro Ser Leu Ser Thr Ser Asp
 1               5                  10                  15

His Ala Ser Val Val Ala Leu Asn Leu Phe Val Ala Leu Leu Cys Ala
```

-continued

```
                20                  25                  30
Cys Ile Val Leu Gly His Leu Leu Glu Glu Asn Arg Trp Met Asn Glu
             35                  40                  45
Ser Ile Thr Ala Leu Leu Ile Gly Leu Gly Thr Gly Val Thr Ile Leu
         50                  55                  60
Leu Ile Ser Lys Gly Lys Ser Ser His Leu Leu Val Phe Ser Glu Asp
 65                  70                  75                  80
Leu Phe Phe Ile Tyr Leu Leu Pro Pro Ile Ile Phe Asn Ala Gly Phe
                 85                  90                  95
Gln Val Lys Lys Gln Phe Phe Arg Asn Phe Val Thr Ile Met Leu
             100                 105                 110
Phe Gly Ala Val Gly Thr Ile Ile Ser Cys Thr Ile Ile Ser Leu Gly
             115                 120                 125
Val Thr Gln Phe Phe Lys Lys Leu Asp Ile Gly Thr Phe Asp Leu Gly
         130                 135                 140
Asp Tyr Leu Ala Ile Gly Ala Ile Phe Ala Ala Thr Asp Ser Val Cys
145                 150                 155                 160
Thr Leu Gln Val Leu Asn Gln Asp Glu Thr Pro Leu Leu Tyr Ser Leu
                 165                 170                 175
Val Phe Gly Glu Gly Val Val Asn Asp Ala Thr Ser Val Val Phe
             180                 185                 190
Asn Ala Ile Gln Ser Phe Asp Leu Thr His Leu Asn His Glu Ala Ala
             195                 200                 205
Phe His Leu Leu Gly Asn Phe Leu Tyr Leu Phe Leu Leu Ser Thr Leu
         210                 215                 220
Leu Gly Ala Ala Thr Gly Leu Ile Ser Ala Tyr Val Ile Lys Lys Leu
225                 230                 235                 240
Tyr Phe Gly Arg His Ser Thr Asp Arg Glu Val Ala Leu Met Met Leu
                 245                 250                 255
Met Ala Tyr Leu Ser Tyr Met Leu Ala Glu Leu Phe Asp Leu Ser Gly
             260                 265                 270
Ile Leu Thr Val Phe Phe Cys Gly Ile Val Met Ser His Tyr Thr Trp
         275                 280                 285
His Asn Val Thr Glu Ser Ser Arg Ile Thr Thr Lys His Thr Phe Ala
     290                 295                 300
Thr Leu Ser Phe Leu Ala Glu Thr Phe Ile Phe Leu Tyr Val Gly Met
305                 310                 315                 320
Asp Ala Leu Asp Ile Asp Lys Trp Arg Ser Val Ser Asp Thr Pro Gly
                 325                 330                 335
Thr Ser Ile Ala Val Ser Ser Ile Leu Met Gly Leu Val Met Val Gly
             340                 345                 350
Arg Ala Ala Phe Val Phe Pro Leu Ser Phe Leu Ser Asn Leu Ala Lys
         355                 360                 365
Lys Asn Gln Ser Glu Lys Ile Asn Phe Asn Met Gln Val Val Ile Trp
     370                 375                 380
Trp Ser Gly Leu Met Arg Gly Ala Val Ser Met Ala Leu Ala Tyr Asn
385                 390                 395                 400
Lys Phe Thr Arg Ala Gly His Thr Asp Val Arg Gly Asn Ala Ile Met
                 405                 410                 415
Ile Thr Ser Thr Ile Thr Val Cys Leu Phe Ser Thr Val Val Phe Gly
             420                 425                 430
Met Leu Thr Lys Pro Leu Ile Ser Tyr Leu Leu Pro His Gln Asn Ala
         435                 440                 445
```

```
Thr Thr Ser Met Leu Ser Asp Asp Asn Thr Pro Lys Ser Ile His Ile
    450                 455                 460

Pro Leu Leu Asp Gln Asp Ser Phe Ile Glu Pro Ser Gly Asn His Asn
465                 470                 475                 480

Val Pro Arg Pro Asp Ser Ile Arg Gly Phe Leu Thr Arg Pro Thr Arg
                485                 490                 495

Asn Arg Ala Leu Leu Thr Gly Asp Asn Leu Met Thr Leu Ser Cys Asp
            500                 505                 510

Pro Ser Leu Glu Val Val Ala Leu Tyr Pro Leu Phe Gln Val Leu Gln
        515                 520                 525

Leu Arg Glu Thr Leu Leu Ile Leu Val Arg Leu Gly Asn Val Glu
    530                 535                 540

Glu Lys Leu
545

<210> SEQ ID NO 11
<211> LENGTH: 24
<212> TYPE: DNA
<213> ORGANISM: Synthetic
<220> FEATURE:
<223> OTHER INFORMATION: Page 5 and 53 - Forward primer - Isolated
      oligonucleotide sequence

<400> SEQUENCE: 11
gccatgttgg attctctagt gtcg                                          24

<210> SEQ ID NO 12
<211> LENGTH: 27
<212> TYPE: DNA
<213> ORGANISM: Synthetic
<220> FEATURE:
<223> OTHER INFORMATION: Pages 5 and 53 -Reverse primer - isolated
      oligonucleotide

<400> SEQUENCE: 12
ccgaattctc aaagcttttc ttccacg                                       27

<210> SEQ ID NO 13
<211> LENGTH: 29
<212> TYPE: DNA
<213> ORGANISM: Synthetic
<220> FEATURE:
<223> OTHER INFORMATION: Pages 5 and 53 - Isolated oligonucleotide

<400> SEQUENCE: 13
cggaattcac agaaaaacac agtgaggat                                     29

<210> SEQ ID NO 14
<211> LENGTH: 24
<212> TYPE: DNA
<213> ORGANISM: Synthetic
<220> FEATURE:
<223> OTHER INFORMATION: Page 5 - Isolated oligonucleotide

<400> SEQUENCE: 14
gccatgttgg attctctagt gtcg                                          24

<210> SEQ ID NO 15
<211> LENGTH: 27
<212> TYPE: DNA
<213> ORGANISM: Synthetic
<220> FEATURE:
<223> OTHER INFORMATION: Page 5 - Isolated oligonucleotide
```

```
<400> SEQUENCE: 15
ccgaattctc aaagcttttc ttccacg                                        27

<210> SEQ ID NO 16
<211> LENGTH: 29
<212> TYPE: DNA
<213> ORGANISM: Synthetic
<220> FEATURE:
<223> OTHER INFORMATION: Page 5 - Isolated oligonucleotide

<400> SEQUENCE: 16
cggaattcac agaaaaacac agtgaggat                                      29

<210> SEQ ID NO 17
<211> LENGTH: 1683
<212> TYPE: DNA
<213> ORGANISM: Arabidopsis thaliana
<220> FEATURE:
<221> NAME/KEY: CDS
<222> LOCATION: (67)..(1041)
<223> OTHER INFORMATION: Figure 1(d)

<400> SEQUENCE: 17
cgccacgacc ctcagggcca ggttaagcag cagcaagcgg ccggcgttgg tatactgctt    60 cagatt atg atg ctc gtg ctt tcc ttc gtt ctc ggc cat gtc ctc cgc     108
       Met Met Leu Val Leu Ser Phe Val Leu Gly His Val Leu Arg
         1               5                  10 cgt cat cga ttc cac tat ctt cct gaa gcc agc ggt tcg ctt ctc att    156
Arg His Arg Phe His Tyr Leu Pro Glu Ala Ser Gly Ser Leu Leu Ile
 15                  20                  25                  30 ggt tta atc gtc ggt ata ctt gct aat atc tcc gat act gag act agc    204
Gly Leu Ile Val Gly Ile Leu Ala Asn Ile Ser Asp Thr Glu Thr Ser
                 35                  40                  45 att agg acg tgg ttt aat ttc cac gaa gag ttc ttc ttc ttg ttt ttg    252
Ile Arg Thr Trp Phe Asn Phe His Glu Glu Phe Phe Phe Leu Phe Leu
     50                  55                  60 ttg cct ccc atc ata ttc cag tca ggt ttc agt ctt caa cct aaa cca    300
Leu Pro Pro Ile Ile Phe Gln Ser Gly Phe Ser Leu Gln Pro Lys Pro
 65                  70                  75 ttc ttt tct aac ttt gga gcc att gtt acc ttt gct atc atc gga act    348
Phe Phe Ser Asn Phe Gly Ala Ile Val Thr Phe Ala Ile Ile Gly Thr
             80                  85                  90 ttt gtc gct tca gtt gtt act ggt ggt ctg gtt tat ctt ggc ggc tct    396
Phe Val Ala Ser Val Val Thr Gly Gly Leu Val Tyr Leu Gly Gly Ser
 95                 100                 105                 110 atg tat ctc atg tat aaa ctt ccc ttt gtt gag tgt ctt atg ttt ggt    444
Met Tyr Leu Met Tyr Lys Leu Pro Phe Val Glu Cys Leu Met Phe Gly
                115                 120                 125 gca ctt ata tca gct acg gac cct gtc act gta ctc tct ata ttc cag    492
Ala Leu Ile Ser Ala Thr Asp Pro Val Thr Val Leu Ser Ile Phe Gln
            130                 135                 140 gat gtg ggc acc gat gtt aac ctg tat gct ttg gtc ttt gga gaa tca    540
Asp Val Gly Thr Asp Val Asn Leu Tyr Ala Leu Val Phe Gly Glu Ser
145                 150                 155 gtt ctg aat gat gct atg gca ata tca ttg tac aga aca atg tcc tta    588
Val Leu Asn Asp Ala Met Ala Ile Ser Leu Tyr Arg Thr Met Ser Leu
            160                 165                 170 gta aac cgc cag tcc tcg tct ggg gaa cat ttt ttc atg gtg gtg atc    636
Val Asn Arg Gln Ser Ser Ser Gly Glu His Phe Phe Met Val Val Ile
175                 180                 185                 190
```

```
agg ttt ttt gag act ttt gct ggc tca atg tct gca ggg gtt ggg gtt      684
Arg Phe Phe Glu Thr Phe Ala Gly Ser Met Ser Ala Gly Val Gly Val
                195                 200                 205 gga ttc act tca gct tta ctc ttt aag tat gca gga ttg gac acc gag      732
Gly Phe Thr Ser Ala Leu Leu Phe Lys Tyr Ala Gly Leu Asp Thr Glu
            210                 215                 220 aat ctt cag aac ttg gag tgt tgt ctc ttt gta ctt ttc ccg tat ttt      780
Asn Leu Gln Asn Leu Glu Cys Cys Leu Phe Val Leu Phe Pro Tyr Phe
        225                 230                 235 tca tac atg ctt gca gaa ggt gtt ggt ctc tcc ggc att gtt tct ata      828
Ser Tyr Met Leu Ala Glu Gly Val Gly Leu Ser Gly Ile Val Ser Ile
    240                 245                 250 ctc ttc aca gga att gtt atg aag cgc tac act ttc tca aat ctc tca      876
Leu Phe Thr Gly Ile Val Met Lys Arg Tyr Thr Phe Ser Asn Leu Ser
255                 260                 265                 270 gaa gct tca cag agt ttc gta tct tct ttt ttt cac ttg ata tct tcg      924
Glu Ala Ser Gln Ser Phe Val Ser Ser Phe Phe His Leu Ile Ser Ser
                275                 280                 285 cta gca gaa act ttc acg ttc att tac atg gga ttt gat att gcc atg      972
Leu Ala Glu Thr Phe Thr Phe Ile Tyr Met Gly Phe Asp Ile Ala Met
            290                 295                 300 gag cag cat agc tgg tcc cat gtt ggg ttt atc ctt ttc tct att gta     1020
Glu Gln His Ser Trp Ser His Val Gly Phe Ile Leu Phe Ser Ile Val
        305                 310                 315 tcc tca ttt act gat cgt cag tgattgtatg cagtggctgt caatgtattt       1071
Ser Ser Phe Thr Asp Arg Gln
    320                 325 gggtgtgcat atttggtcaa cctatttaga caggagaacc agaagatacc tatgaagcac    1131
caaaaagccc tttggtatag tggacttcga ggggcaatgg catttgcact tgcacttcaa    1191
tcacttcatg atctaccaga gggtcacggc caaatcatct ttactgcaaa ccacaactat    1251
tgttgttgtc acggttttac taataggagg ttcgacaggt aaaatgttgg aagctttgga    1311
agttgtaggt gacgatcttg atgactccat gtctgaaggc tttgaagaga gcgatcatca    1371
gtatgtccct cctccttta gcattggagc ttcatctgac gaggatacat catcatcagg     1431
aagcaggttc aagatgaagc tgaaggagtt tcacaaaacc actacatcat tcaccgcgtt    1491
ggacaaaaac tttctgactc cgttcttcac aactaatagt ggagatggag atggagatgg    1551
ggagtagcat ggaaaagatg tgtatttgtg gtccaggcca agctataatt agagtacaca    1611
tatgtctatg taagattaac actggttgat tttacctctc gcaaaatgcc cactataaag    1671
ttgacgattt cc                                                        1683

<210> SEQ ID NO 18
<211> LENGTH: 325
<212> TYPE: PRT
<213> ORGANISM: Arabidopsis thaliana
<220> FEATURE:
<223> OTHER INFORMATION: Figure 1(d)

<400> SEQUENCE: 18

Met Met Leu Val Leu Ser Phe Val Leu Gly His Val Leu Arg Arg His
1               5                   10                  15

Arg Phe His Tyr Leu Pro Glu Ala Ser Gly Ser Leu Leu Ile Gly Leu
            20                  25                  30

Ile Val Gly Ile Leu Ala Asn Ile Ser Asp Thr Glu Thr Ser Ile Arg
        35                  40                  45

Thr Trp Phe Asn Phe His Glu Glu Phe Phe Leu Phe Leu Leu Pro
    50                  55                  60
```

```
Pro Ile Ile Phe Gln Ser Gly Phe Ser Leu Gln Pro Lys Pro Phe Phe
65                  70                  75                  80

Ser Asn Phe Gly Ala Ile Val Thr Phe Ala Ile Ile Gly Thr Phe Val
                85                  90                  95

Ala Ser Val Val Thr Gly Gly Leu Val Tyr Leu Gly Gly Ser Met Tyr
            100                 105                 110

Leu Met Tyr Lys Leu Pro Phe Val Glu Cys Leu Met Phe Gly Ala Leu
        115                 120                 125

Ile Ser Ala Thr Asp Pro Val Thr Val Leu Ser Ile Phe Gln Asp Val
    130                 135                 140

Gly Thr Asp Val Asn Leu Tyr Ala Leu Val Phe Gly Glu Ser Val Leu
145                 150                 155                 160

Asn Asp Ala Met Ala Ile Ser Leu Tyr Arg Thr Met Ser Leu Val Asn
                165                 170                 175

Arg Gln Ser Ser Ser Gly Glu His Phe Phe Met Val Val Ile Arg Phe
            180                 185                 190

Phe Glu Thr Phe Ala Gly Ser Met Ser Ala Gly Val Gly Val Gly Phe
        195                 200                 205

Thr Ser Ala Leu Leu Phe Lys Tyr Ala Gly Leu Asp Thr Glu Asn Leu
    210                 215                 220

Gln Asn Leu Glu Cys Cys Leu Phe Val Leu Phe Pro Tyr Phe Ser Tyr
225                 230                 235                 240

Met Leu Ala Glu Gly Val Gly Leu Ser Gly Ile Val Ser Ile Leu Phe
                245                 250                 255

Thr Gly Ile Val Met Lys Arg Tyr Thr Phe Ser Asn Leu Ser Glu Ala
            260                 265                 270

Ser Gln Ser Phe Val Ser Ser Phe His Leu Ile Ser Ser Leu Ala
        275                 280                 285

Glu Thr Phe Thr Phe Ile Tyr Met Gly Phe Asp Ile Ala Met Glu Gln
    290                 295                 300

His Ser Trp Ser His Val Gly Phe Ile Leu Phe Ser Ile Val Ser Ser
305                 310                 315                 320

Phe Thr Asp Arg Gln
                325

<210> SEQ ID NO 19
<211> LENGTH: 2122
<212> TYPE: DNA
<213> ORGANISM: Arabidopsis thaliana
<220> FEATURE:
<221> NAME/KEY: CDS
<222> LOCATION: (55)..(750)
<223> OTHER INFORMATION: Figure 1(e) AtNHX4 cDNA sequence

<400> SEQUENCE: 19
cagggccagg ttaagcagca gcaagcggcc ggcgttggta tactgcttca gatt atg        57
                                                            Met
                                                            1
atg ctc gtg ctt tcc ttc gtt ctc ggc cat gtc ctc cgc cgt cat cga       105
Met Leu Val Leu Ser Phe Val Leu Gly His Val Leu Arg Arg His Arg
        5                   10                  15 ttc cac tat ctt cct gaa gcc agc ggt tcg ctt ctc att ggt tta atc      153
Phe His Tyr Leu Pro Glu Ala Ser Gly Ser Leu Leu Ile Gly Leu Ile
            20                  25                  30 gtc ggt ata ctt gct aat atc tcc gat act gag act agc att agg acg      201
Val Gly Ile Leu Ala Asn Ile Ser Asp Thr Glu Thr Ser Ile Arg Thr
        35                  40                  45
```

-continued

| | |
|---|---|
| tgg ttt aat ttc cac gaa gag ttc ttc ttc ttg ttt ttg ttg cct ccc<br>Trp Phe Asn Phe His Glu Glu Phe Phe Phe Leu Phe Leu Leu Pro Pro<br>50                              55                       60                     65 | 249 |
| atc ata ttc cag tca ggt ttc agt ctt caa cct aaa cca ttc ttt tct<br>Ile Ile Phe Gln Ser Gly Phe Ser Leu Gln Pro Lys Pro Phe Phe Ser<br>                 70                       75                       80 | 297 |
| aac ttt gga gcc att gtt acc ttt gct atc atc gga act ttt gtc gct<br>Asn Phe Gly Ala Ile Val Thr Phe Ala Ile Ile Gly Thr Phe Val Ala<br>                85                      90                      95 | 345 |
| tca gtt gtt act ggt ggt ctg gtt tat ctt ggc ggc tct atg tat ctc<br>Ser Val Val Thr Gly Gly Leu Val Tyr Leu Gly Gly Ser Met Tyr Leu<br>               100                     105                    110 | 393 |
| atg tat aaa ctt ccc ttt gtt gag tgt ctt atg ttt ggt gca ctt ata<br>Met Tyr Lys Leu Pro Phe Val Glu Cys Leu Met Phe Gly Ala Leu Ile<br>115                         120                     125 | 441 |
| tca gct acg gac cct gtc act gta ctc tct ata ttc cag gat gtg ggc<br>Ser Ala Thr Asp Pro Val Thr Val Leu Ser Ile Phe Gln Asp Val Gly<br>130                        135                     140                   145 | 489 |
| acc gat gtt aac ctg tat gct ttg gtc ttt gga gaa tca gtt ctg aat<br>Thr Asp Val Asn Leu Tyr Ala Leu Val Phe Gly Glu Ser Val Leu Asn<br>               150                     155                    160 | 537 |
| gat gct atg gca ata tca ttg tac aga aca atg tcc tta gta aac cgc<br>Asp Ala Met Ala Ile Ser Leu Tyr Arg Thr Met Ser Leu Val Asn Arg<br>                165                   170                   175 | 585 |
| cag tcc tcg tct ggg gaa cat ttt ttc atg gtg gtg atc agg ttt ttt<br>Gln Ser Ser Ser Gly Glu His Phe Phe Met Val Val Ile Arg Phe Phe<br>               180                    185                    190 | 633 |
| gag act ttt gct ggc tca atg tct gca ggg gtt ggg gtt gga ttc act<br>Glu Thr Phe Ala Gly Ser Met Ser Ala Gly Val Gly Val Gly Phe Thr<br>195                         200                     205 | 681 |
| tca gct tta ata tcc ttc ctc gaa tcc tct att ttt ctt att aga tgt<br>Ser Ala Leu Ile Ser Phe Leu Glu Ser Ser Ile Phe Leu Ile Arg Cys<br>210                         215                     220                  225 | 729 |
| cac atg gcc aaa aat gta ttg taaaatctta actcagaaca cctctttaag<br>His Met Ala Lys Asn Val Leu<br>               230 | 780 |
| tatgcaggat tggacaccga gaatcttcag aacttggagt gttgtctctt tgtacttttc | 840 |
| ccgtattttt cgtaagtaga caaaacaact ctcctcctgt ctcttcgtat ttatgacaac | 900 |
| acttcttccc cctaatgtat tctggttatt ctgtaagata catgcttgca gaaggtgttg | 960 |
| gtctctccgg cattgtttct atactcttca caggaattgt aatcgccgag tcattgtagc | 1020 |
| ttttacatct tagttgatgt taatatcttg gaaagacata tttaggctgc ctaatatagt | 1080 |
| gctactgtag gttatgaagc gctacacttt ctcaaatctc tcagaagctt cacagagttt | 1140 |
| cgtatcttct ttttttcact tgatatcttc gctagcagaa actttcacgt tcatttacat | 1200 |
| gggatttgat attgccatgg agcagcatag ctggtcccat gttgggttta tccttttctc | 1260 |
| tattgtatcc tcatttactg atcgtcagtg attgtatgca gtgttagtca gtgttgtaaa | 1320 |
| tccttgactt taccttttgc ttctgcgttt catgactgac atcagttgtt tattggcgtg | 1380 |
| gctaggtgac taaatgcttt tttatcctgg ctgatcgctt cattatcacc atggttttcg | 1440 |
| attcggattt acctatatgt tctgcaatgc ttttctcacg cagggctgtc aatgtatttg | 1500 |
| ggtgtgcata tttggtcaac ctatttagac aggagaacca gaagatacct atgaagcacc | 1560 |
| aaaaagccct tggtatagt ggacttcgag gggcaatggc atttgcactt gcacttcaat | 1620 |
| cacttcatga tctaccagag ggtcacggcc aaatcatctt tactgcaacc acaactattg | 1680 |
| ttgttgtcac ggttttacta ataggaggtt cgacaggtaa aatgttggaa gctttggaag | 1740 |

-continued

```
ttgtaggtga cgatcttgat gactccatgt ctgaaggctt tgaagagagc gatcatcagt    1800
atgtccctcc tccttttagc attggagctt catctgacga ggatacatca tcatcaggaa    1860
gcaggttcaa gatgaagctg aaggagtttc acaaaaccac tacatcattc accgcgttgg    1920
acaaaaactt tctgactccg ttcttcacaa ctaatagtgg agatggagat ggagatgggg    1980
agtagcatgg aaaagatgtg tatttgtggt ccaggccaag ctataattag agtacacata    2040
tgtctatgta agattaacac tggttgattt tacctctcgc aaaatgccca ctataaagtt    2100
gacgatttcc aagacatttc ga                                             2122
```

<210> SEQ ID NO 20
<211> LENGTH: 232
<212> TYPE: PRT
<213> ORGANISM: Arabidopsis thaliana
<220> FEATURE:
<223> OTHER INFORMATION: Figure 1(e)

<400> SEQUENCE: 20

```
Met Met Leu Val Leu Ser Phe Val Leu Gly His Val Leu Arg Arg His
 1               5                  10                  15

Arg Phe His Tyr Leu Pro Glu Ala Ser Gly Ser Leu Leu Ile Gly Leu
                20                  25                  30

Ile Val Gly Ile Leu Ala Asn Ile Ser Asp Thr Glu Thr Ser Ile Arg
            35                  40                  45

Thr Trp Phe Asn Phe His Glu Glu Phe Phe Leu Phe Leu Leu Pro
        50                  55                  60

Pro Ile Ile Phe Gln Ser Gly Phe Ser Leu Gln Pro Lys Pro Phe Phe
65                  70                  75                  80

Ser Asn Phe Gly Ala Ile Val Thr Phe Ala Ile Ile Gly Thr Phe Val
                85                  90                  95

Ala Ser Val Val Thr Gly Gly Leu Val Tyr Leu Gly Ser Met Tyr
            100                 105                 110

Leu Met Tyr Lys Leu Pro Phe Val Glu Cys Leu Met Phe Gly Ala Leu
        115                 120                 125

Ile Ser Ala Thr Asp Pro Val Thr Val Leu Ser Ile Phe Gln Asp Val
    130                 135                 140

Gly Thr Asp Val Asn Leu Tyr Ala Leu Val Phe Gly Glu Ser Val Leu
145                 150                 155                 160

Asn Asp Ala Met Ala Ile Ser Leu Tyr Arg Thr Met Ser Leu Val Asn
                165                 170                 175

Arg Gln Ser Ser Ser Gly Glu His Phe Phe Met Val Val Ile Arg Phe
            180                 185                 190

Phe Glu Thr Phe Ala Gly Ser Met Ser Ala Gly Val Gly Val Gly Phe
        195                 200                 205

Thr Ser Ala Leu Ile Ser Phe Leu Glu Ser Ser Ile Phe Leu Ile Arg
    210                 215                 220

Cys His Met Ala Lys Asn Val Leu
225                 230
```

<210> SEQ ID NO 21
<211> LENGTH: 569
<212> TYPE: PRT
<213> ORGANISM: Schizosaccharomyces pombe
<220> FEATURE:
<223> OTHER INFORMATION: Figure 8(a)

<400> SEQUENCE: 21

```
Met Pro Asp Ser Lys His Trp Val Ile Leu Leu Phe Arg Arg Asp Gly
  1               5                  10                  15
Asp Asp Asp Asp Asp Gly Gln Asp Pro Ala Leu Gln Glu Leu Tyr
             20                  25                  30
Ser Ser Trp Ala Leu Phe Ile Leu Leu Val Leu Leu Ile Gly Ala Leu
         35                  40                  45
Leu Thr Ser Tyr Tyr Val Gln Ser Lys Lys Ile Arg Ala Ile His Glu
     50                  55                  60
Thr Val Ile Ser Val Phe Val Gly Met Val Val Gly Leu Ile Ile Arg
 65                  70                  75                  80
Val Ser Pro Gly Leu Ile Ile Gln Asn Met Val Ser Phe His Ser Thr
             85                  90                  95
Tyr Phe Phe Asn Val Leu Leu Pro Pro Ile Ile Leu Asn Ser Gly Tyr
                 100                 105                 110
Glu Leu His Gln Ser Asn Phe Phe Arg Asn Ile Gly Thr Ile Leu Thr
             115                 120                 125
Phe Ala Phe Ala Gly Thr Phe Ile Ser Ala Val Thr Leu Gly Val Leu
 130                 135                 140
Val Tyr Ile Phe Ser Phe Leu Asn Phe Glu Asn Leu Ser Met Thr Phe
145                 150                 155                 160
Val Glu Ala Leu Ser Met Gly Ala Thr Leu Ser Ala Thr Asp Pro Val
             165                 170                 175
Thr Val Leu Ala Ile Phe Asn Ser Tyr Lys Val Asp Gln Lys Leu Tyr
             180                 185                 190
Thr Ile Ile Phe Gly Glu Ser Ile Leu Asn Asp Ala Val Ala Ile Val
         195                 200                 205
Met Phe Glu Thr Leu Gln Gln Phe Gln Gly Lys Thr Leu His Phe Phe
 210                 215                 220
Thr Leu Phe Ser Gly Ile Gly Ile Phe Ile Thr Phe Phe Ile Ser
225                 230                 235                 240
Leu Leu Ile Gly Val Ser Ile Gly Leu Ile Thr Ala Leu Leu Leu Lys
             245                 250                 255
Tyr Ser Tyr Leu Arg Arg Tyr Pro Ser Ile Glu Ser Cys Ile Ile Leu
             260                 265                 270
Leu Met Ala Tyr Thr Ser Tyr Phe Phe Ser Asn Gly Cys His Met Ser
         275                 280                 285
Gly Val Val Ser Leu Leu Phe Cys Gly Ile Thr Leu Lys His Tyr Ala
         290                 295                 300
Phe Phe Asn Met Ser Tyr Lys Ala Lys Leu Ser Thr Lys Tyr Val Phe
305                 310                 315                 320
Arg Val Leu Ala Gln Leu Ser Glu Asn Phe Ile Phe Ile Tyr Leu Gly
             325                 330                 335
Met Ser Leu Phe Thr Gln Val Asp Leu Val Tyr Lys Pro Ile Phe Ile
         340                 345                 350
Leu Ile Thr Thr Val Ala Val Thr Ala Ser Arg Tyr Met Asn Val Phe
         355                 360                 365
Pro Leu Ser Asn Leu Leu Asn Lys Phe His Arg Gln Arg Asn Gly Asn
         370                 375                 380
Leu Ile Asp His Ile Pro Tyr Ser Tyr Gln Met Met Leu Phe Trp Ala
385                 390                 395                 400
Gly Leu Arg Gly Ala Val Gly Val Ala Leu Ala Ala Gly Phe Glu Gly
             405                 410                 415
```

-continued

```
Glu Asn Ala Gln Thr Leu Arg Ala Thr Thr Leu Val Val Val Leu
            420                 425                 430

Thr Leu Ile Ile Phe Gly Gly Thr Ala Arg Met Leu Glu Ile Leu
            435                 440                 445

His Ile Glu Thr Gly Val Ala Ala Asp Val Asp Ser Asp Thr Glu Ile
            450                 455                 460

Gly Met Leu Pro Trp Gln Gln Ser Pro Glu Phe Asp Leu Glu Asn Ser
465                 470                 475                 480

Ala Met Glu Leu Ser Asp Ala Ser Ala Glu Pro Val Val Val Asp Gln
                485                 490                 495

Gln Phe Thr Thr Glu His Phe Asp Glu Gly Asn Ile Ala Pro Thr Leu
            500                 505                 510

Ser Lys Lys Val Ser Ser Thr Phe Glu Gln Tyr Gln Arg Ala Ala Gly
            515                 520                 525

Ala Phe Asn Gln Phe Phe His Ser Ser Arg Asp Gln Ala Gln Trp
            530                 535                 540

Leu Thr Arg Phe Asp Glu Val Ile Lys Pro Val Leu Leu Glu Arg
545                 550                 555                 560

Asp Asn Leu Lys Asn Gly Thr Lys Lys
                565
```

<210> SEQ ID NO 22
<211> LENGTH: 633
<212> TYPE: PRT
<213> ORGANISM: Saccharomyces cerevisiae
<220> FEATURE:
<223> OTHER INFORMATION: Figure 8(b)

<400> SEQUENCE: 22

```
Met Leu Ser Lys Val Leu Leu Asn Ile Ala Phe Lys Val Leu Leu Thr
  1               5                  10                  15

Thr Ala Lys Arg Ala Val Asp Pro Asp Asp Asp Glu Leu Leu Pro
            20                  25                  30

Ser Pro Asp Leu Pro Gly Ser Asp Asp Pro Ile Ala Gly Asp Pro Asp
            35                  40                  45

Val Asp Leu Asn Pro Val Thr Glu Glu Met Phe Ser Ser Trp Ala Leu
        50                  55                  60

Phe Ile Met Leu Leu Leu Ile Ser Ala Leu Trp Ser Ser Tyr Tyr
 65                  70                  75                  80

Leu Thr Gln Lys Arg Ile Arg Ala Val His Glu Thr Val Leu Ser Ile
                85                  90                  95

Phe Tyr Gly Met Val Ile Gly Leu Ile Ile Arg Met Ser Pro Gly His
            100                 105                 110

Tyr Ile Gln Asp Thr Val Thr Phe Asn Ser Ser Tyr Phe Phe Asn Val
            115                 120                 125

Leu Leu Pro Pro Ile Ile Leu Asn Ser Gly Tyr Glu Leu Asn Gln Val
            130                 135                 140

Asn Phe Phe Asn Asn Met Leu Ser Ile Leu Ile Phe Ala Ile Pro Gly
145                 150                 155                 160

Thr Phe Ile Ser Ala Val Val Ile Gly Ile Ile Leu Tyr Ile Trp Thr
                165                 170                 175

Phe Leu Gly Leu Glu Ser Ile Asp Ile Ser Phe Ala Asp Ala Met Ser
            180                 185                 190

Val Gly Ala Thr Leu Ser Ala Thr Asp Pro Val Thr Ile Leu Ser Ile
            195                 200                 205
```

-continued

```
Phe Asn Ala Tyr Lys Val Asp Pro Lys Leu Tyr Thr Ile Ile Phe Gly
    210                 215                 220
Glu Ser Leu Leu Asn Asp Ala Ile Ser Ile Val Met Phe Glu Thr Cys
225                 230                 235                 240
Gln Lys Phe His Gly Gln Pro Ala Thr Phe Ser Ser Val Phe Glu Gly
                245                 250                 255
Ala Gly Leu Phe Leu Met Thr Phe Ser Val Ser Leu Leu Ile Gly Val
            260                 265                 270
Leu Ile Gly Ile Leu Val Ala Leu Leu Leu Lys His Thr His Ile Arg
        275                 280                 285
Arg Tyr Pro Gln Ile Glu Ser Cys Leu Ile Leu Leu Ile Ala Tyr Glu
    290                 295                 300
Ser Tyr Phe Phe Ser Asn Gly Cys His Met Ser Gly Ile Val Ser Leu
305                 310                 315                 320
Leu Phe Cys Gly Ile Thr Leu Lys His Tyr Ala Tyr Tyr Asn Met Ser
                325                 330                 335
Arg Arg Ser Gln Ile Thr Ile Lys Tyr Ile Phe Gln Leu Leu Ala Arg
            340                 345                 350
Leu Ser Glu Asn Phe Ile Phe Ile Tyr Leu Gly Leu Glu Leu Phe Thr
        355                 360                 365
Glu Val Glu Leu Val Tyr Lys Pro Leu Leu Ile Ile Val Ala Ala Ile
    370                 375                 380
Ser Ile Cys Val Ala Arg Trp Cys Ala Val Phe Pro Leu Ser Gln Phe
385                 390                 395                 400
Val Asn Trp Ile Tyr Arg Val Lys Thr Ile Arg Ser Met Ser Gly Ile
                405                 410                 415
Thr Gly Glu Asn Ile Ser Val Pro Asp Glu Ile Pro Tyr Asn Tyr Gln
            420                 425                 430
Met Met Thr Phe Trp Ala Gly Leu Arg Gly Ala Val Gly Val Ala Leu
        435                 440                 445
Ala Leu Gly Ile Gln Gly Glu Tyr Lys Phe Thr Leu Leu Ala Thr Val
    450                 455                 460
Leu Val Val Val Val Leu Thr Val Ile Ile Phe Gly Gly Thr Thr Ala
465                 470                 475                 480
Gly Met Leu Glu Val Leu Asn Ile Lys Thr Gly Cys Ile Ser Glu Glu
                485                 490                 495
Asp Thr Ser Asp Asp Glu Phe Asp Ile Glu Ala Pro Arg Ala Ile Asn
            500                 505                 510
Leu Leu Asn Gly Ser Ser Ile Gln Thr Asp Leu Gly Pro Tyr Ser Asp
        515                 520                 525
Asn Asn Ser Pro Asp Ile Ser Ile Asp Gln Phe Ala Val Ser Ser Asn
    530                 535                 540
Lys Asn Leu Pro Asn Asn Ile Ser Thr Gly Gly Asn Thr Phe Gly
545                 550                 555                 560
Gly Leu Asn Glu Thr Glu Asn Thr Ser Pro Asn Pro Ala Arg Ser Ser
                565                 570                 575
Met Asp Lys Arg Asn Leu Arg Asp Lys Leu Gly Thr Ile Phe Asn Ser
            580                 585                 590
Asp Ser Gln Trp Phe Gln Asn Phe Asp Glu Gln Val Leu Lys Pro Val
        595                 600                 605
Phe Leu Asp Asn Val Ser Pro Ser Leu Gln Asp Ser Ala Thr Gln Ser
    610                 615                 620
Pro Ala Asp Phe Ser Ser Gln Asn His
```

```
625           630
```

<210> SEQ ID NO 23
<211> LENGTH: 378
<212> TYPE: DNA
<213> ORGANISM: Oryza sativa
<220> FEATURE:
<223> OTHER INFORMATION: Figure 8(c); n=unkown

<400> SEQUENCE: 23

| caagaagcta tacattggaa ggcattctac tgaccgtgag gttgcccctta tgatgctcat | 60 |
| ggcttacctt tcatatatgc tggctgagtt gctagatttg agcggcattc tcaccgtatt | 120 |
| cttctgtggt attgtaatgt cacattacac ttggcataac gtcacagaga gttcaagagt | 180 |
| tacaacaaag cacgcatttg caactctgtc cttcattgct gagacttttc tcttcctgta | 240 |
| tgttgggatg gatgcattgg atattgaaaa atgggagntt nccagtgaca gacctggnaa | 300 |
| atccattngg gtaagctcaa ttttgctagg gattggttcc tgattggaag ngctgctttt | 360 |
| gnaattcccc tggtggtc | 378 |

<210> SEQ ID NO 24
<211> LENGTH: 268
<212> TYPE: DNA
<213> ORGANISM: Oryza sativa
<220> FEATURE:
<223> OTHER INFORMATION: Figure 8 (d); n=unknown

<400> SEQUENCE: 24

| gtttggtaat tggaggaggt ggagtaatgg agctcgggtt ggggatgggg atggggctgg | 60 |
| gcgacccgnc tgcggactac ggctcgatcg cggcggtggg gatgttcgtg gcgctcatct | 120 |
| gcgtctgcat cgtcgtcggc cacctcctcg aggagagccg atggatgaac gagtccatca | 180 |
| ccgcgctaat catcggggttg ggtacttgga ggagtgnttt tgnatggtgt cgagctggaa | 240 |
| gcactcggna tactggtgtt cagcgagg | 268 |

<210> SEQ ID NO 25
<211> LENGTH: 380
<212> TYPE: DNA
<213> ORGANISM: Oryza sativa
<220> FEATURE:
<223> OTHER INFORMATION: Figure 8(e); n=unknown

<400> SEQUENCE: 25

| acattccctg aaagnactgc tggacntttg agggctcgga tgcctgtaga tccaggactc | 60 |
| aaaggatgnt gagctagagg ttgttgggat ggtgaagttt gcttaccaag ggccatttac | 120 |
| attgtctggc atcaaactat gcccagccac tgatggcacg gctcagttta atgaggctgg | 180 |
| ccacaccttc tccagtggga gttatctgtg catctaattg gtaccttctt tgtattgtag | 240 |
| ttgttacttt acccttgatt tgttcggttt gcttctaaag caggttgtga aattcctatt | 300 |
| gtatgtngtg acgcttgttt gttttttgag gctggaaatt acatcatgtt tttgatttgt | 360 |
| ctattaaaaa aaaaaaaaaa | 380 |

<210> SEQ ID NO 26
<211> LENGTH: 596
<212> TYPE: DNA
<213> ORGANISM: Medicago truncatula
<220> FEATURE:
<223> OTHER INFORMATION: Figure 8(f); n=unknown

<400> SEQUENCE: 26

```
gtcaaaactc atccctcctc ttccatttgc atattcttct ttatcatctt ttcttcccta      60
aattagagtc tatccttccg cccatagtct ttgacaccct tttcaaaatt ctagaacaag     120
aattttattc ttcatatata tatatatata tatccaatta accatctcaa tctcatattc     180 acatataccct cataaaccat ccataacatc cttaaaaacc ctctaagccc tttcaaactt     240
tgatttgtaa ttgtttctct tataagtctt aacctgcaca aatcaatttt aatttcttat     300
gttcatatag ttatgaatga ttgaaaaaaa cacaaatgac tccagttatc tgtgagatct     360
ctatgataaa ctctactctc cagacgcagg acacatttag ttcaatcttt ctctgttgtt     420
ttcctctact ggttctatat tttctcatga attattaatt aatcctatat tctttctttt     480
caatacaaat ttagtttcat taattctatc aacataatca attaaactac atagttagaa     540
aaatagtact attaccacga tcactcaaag tttttttagtt tttaacaaac antctg        596
```

<210> SEQ ID NO 27
<211> LENGTH: 522
<212> TYPE: DNA
<213> ORGANISM: Hordeum vulgare
<220> FEATURE:
<223> OTHER INFORMATION: Figure 8(g); n=unknown

<400> SEQUENCE: 27

```
atttacatgg ttataccagt tatcttgagc acttatgcat catccagtga tcagttttgc      60
ttccattcag actgatgggt ctggcagaag taatgtattc tggtggactt acatctatca     120
gcgatgatga aacttgatga tcagttttttt tagttgaaaa attctgcaag aacagctact     180
taatgctcta ttgtgtatcg caggcacaca tcagctgctg atgtctgcta tacttctgta     240
ctctcactat agctcatcta tgacgtctag acatgctagc gtatgtgtan nnnacatcgc     300
gctagtatgt atactctcac atcatatgct actgttctat atagaactat gtgatagcta     360
ctgctatact gctgtcatac agagtcccgt taatatcaat gctattttgc tttcctcaaa     420
gaaaaaagga aatgactttc cttttgatta tatatttgat ccaggttttc ggcttgctga     480
ctaagcctct gattaatctc ctcgtcccac caagacctgg ca                       522
```

<210> SEQ ID NO 28
<211> LENGTH: 330
<212> TYPE: DNA
<213> ORGANISM: Arabidopsis thaliana
<220> FEATURE:
<223> OTHER INFORMATION: Figure 8(h); n=unknown

<400> SEQUENCE: 28

```
tttccgttat cgtttctatc taacttagcc aagaagaatc aaagcgagaa aatcaacttt      60
aacatgcagg ttgtgatttg gtggtctggt ctcatgagag gtgctgtatc tatggctctt     120
gcatacaaca agtttacaag ggccgggcac acagatgtac gngggaatgc aatcatgatc     180
acgngtacgn taactgtctg tnttttttagc acagtggtgt ttggtatgct gaccaaacca     240
ntcataagct acctatttac cgnaccanga accgtcatca acgnggcatg tttatcttgn     300
attncaaata acccnaanaa tccnatacca                                      330
```

<210> SEQ ID NO 29
<211> LENGTH: 633
<212> TYPE: PRT
<213> ORGANISM: Saccharomyces cerevisiae
<220> FEATURE:
<223> OTHER INFORMATION: Figure 2(a)

<400> SEQUENCE: 29

```
Met Leu Ser Lys Val Leu Leu Asn Ile Ala Phe Lys Val Leu Leu Thr
  1               5                  10                  15

Thr Ala Lys Arg Ala Val Asp Pro Asp Asp Asp Glu Leu Leu Pro
             20                  25                  30

Ser Pro Asp Leu Pro Gly Ser Asp Asp Pro Ile Ala Gly Asp Pro Asp
             35                  40                  45

Val Asp Leu Asn Pro Val Thr Glu Glu Met Phe Ser Ser Trp Ala Leu
     50                  55                  60

Phe Ile Met Leu Leu Leu Ile Ser Ala Leu Trp Ser Ser Tyr Tyr
 65                  70                  75                  80

Leu Thr Gln Lys Arg Ile Arg Ala Val His Glu Thr Val Leu Ser Ile
                 85                  90                  95

Phe Tyr Gly Met Val Ile Gly Leu Ile Ile Arg Met Ser Pro Gly His
                100                 105                 110

Tyr Ile Gln Asp Thr Val Thr Phe Asn Ser Ser Tyr Phe Phe Asn Val
                115                 120                 125

Leu Leu Pro Pro Ile Ile Leu Asn Ser Gly Tyr Glu Leu Asn Gln Val
            130                 135                 140

Asn Phe Phe Asn Asn Met Leu Ser Ile Leu Ile Phe Ala Ile Pro Gly
145                 150                 155                 160

Thr Phe Ile Ser Ala Val Val Ile Gly Ile Ile Leu Tyr Ile Trp Thr
                165                 170                 175

Phe Leu Gly Leu Glu Ser Ile Asp Ile Ser Phe Ala Asp Ala Met Ser
                180                 185                 190

Val Gly Ala Thr Leu Ser Ala Thr Asp Pro Val Thr Ile Leu Ser Ile
                195                 200                 205

Phe Asn Ala Tyr Lys Val Asp Pro Lys Leu Tyr Thr Ile Ile Phe Gly
            210                 215                 220

Glu Ser Leu Leu Asn Asp Ala Ile Ser Ile Val Met Phe Glu Thr Cys
225                 230                 235                 240

Gln Lys Phe His Gly Gln Pro Ala Thr Phe Ser Ser Val Phe Glu Gly
                245                 250                 255

Ala Gly Leu Phe Leu Met Thr Phe Ser Val Ser Leu Leu Ile Gly Val
                260                 265                 270

Leu Ile Gly Ile Leu Val Ala Leu Leu Lys His Thr His Ile Arg
            275                 280                 285

Arg Tyr Pro Gln Ile Glu Ser Cys Leu Ile Leu Ile Ala Tyr Glu
            290                 295                 300

Ser Tyr Phe Phe Ser Asn Gly Cys His Met Ser Gly Ile Val Ser Leu
305                 310                 315                 320

Leu Phe Cys Gly Ile Thr Leu Lys His Tyr Ala Tyr Tyr Asn Met Ser
                325                 330                 335

Arg Arg Ser Gln Ile Thr Ile Lys Tyr Ile Phe Gln Leu Leu Ala Arg
            340                 345                 350

Leu Ser Glu Asn Phe Ile Phe Ile Tyr Leu Gly Leu Glu Leu Phe Thr
            355                 360                 365

Glu Val Glu Leu Val Tyr Lys Pro Leu Leu Ile Ile Val Ala Ala Ile
            370                 375                 380

Ser Ile Cys Val Ala Arg Trp Cys Ala Val Phe Pro Leu Ser Gln Phe
385                 390                 395                 400

Val Asn Trp Ile Tyr Arg Val Lys Thr Ile Arg Ser Met Ser Gly Ile
                405                 410                 415
```

```
Thr Gly Glu Asn Ile Ser Val Pro Asp Glu Ile Pro Tyr Asn Tyr Gln
            420                 425                 430

Met Met Thr Phe Trp Ala Gly Leu Arg Gly Ala Val Gly Val Ala Leu
            435                 440                 445

Ala Leu Gly Ile Gln Gly Glu Tyr Lys Phe Thr Leu Leu Ala Thr Val
        450                 455                 460

Leu Val Val Val Leu Thr Val Ile Phe Gly Gly Thr Thr Ala
465                 470                 475                 480

Gly Met Leu Glu Val Leu Asn Ile Lys Thr Gly Cys Ile Ser Glu Glu
                485                 490                 495

Asp Thr Ser Asp Asp Glu Phe Asp Ile Glu Ala Pro Arg Ala Ile Asn
            500                 505                 510

Leu Leu Asn Gly Ser Ser Ile Gln Thr Asp Leu Gly Pro Tyr Ser Asp
            515                 520                 525

Asn Asn Ser Pro Asp Ile Ser Ile Asp Gln Phe Ala Val Ser Ser Asn
530                 535                 540

Lys Asn Leu Pro Asn Asn Ile Ser Thr Gly Gly Asn Thr Phe Gly
545                 550                 555                 560

Gly Leu Asn Glu Thr Glu Asn Thr Ser Pro Asn Pro Ala Arg Ser Ser
            565                 570                 575

Met Asp Lys Arg Asn Leu Arg Asp Lys Leu Gly Thr Ile Phe Asn Ser
            580                 585                 590

Asp Ser Gln Trp Phe Gln Asn Phe Asp Glu Gln Val Leu Lys Pro Val
            595                 600                 605

Phe Leu Asp Asn Val Ser Pro Ser Leu Gln Asp Ser Ala Thr Gln Ser
        610                 615                 620

Pro Ala Asp Phe Ser Ser Gln Asn His
625                 630

<210> SEQ ID NO 30
<211> LENGTH: 669
<212> TYPE: PRT
<213> ORGANISM: Homo sapiens
<220> FEATURE:
<223> OTHER INFORMATION: Figure 2(a) HsNHE6 Na+/H+ exchanger (GenBank
      Accession No. 2944237)

<400> SEQUENCE: 30

Met Ala Arg Arg Gly Trp Arg Arg Ala Pro Leu Arg Gly Val Gly
1               5                   10                  15

Ser Ser Pro Arg Ala Arg Arg Leu Met Arg Pro Leu Trp Leu Leu Leu
            20                  25                  30

Ala Val Gly Val Phe Asp Trp Ala Gly Ala Ser Asp Gly Gly Gly Gly
        35                  40                  45

Glu Ala Arg Ala Met Asp Glu Glu Ile Val Ser Glu Lys Gln Ala Glu
    50                  55                  60

Glu Ser His Arg Gln Asp Ser Ala Asn Leu Leu Ile Phe Ile Leu Leu
65                  70                  75                  80

Leu Thr Leu Thr Ile Leu Thr Ile Trp Leu Phe Lys His Arg Arg Ala
                85                  90                  95

Arg Phe Leu His Glu Thr Gly Leu Ala Met Ile Tyr Gly Leu Leu Val
            100                 105                 110

Gly Leu Val Leu Arg Tyr Gly Ile His Val Pro Ser Asp Val Asn Asn
        115                 120                 125

Val Thr Leu Ser Cys Glu Val Gln Ser Ser Pro Thr Thr Leu Leu Val
```

-continued

```
            130                 135                 140
Thr Phe Asp Pro Glu Val Phe Phe Asn Ile Leu Leu Pro Pro Ile Ile
145                 150                 155                 160
Phe Tyr Ala Gly Tyr Ser Leu Lys Arg Arg His Phe Phe Arg Asn Leu
                165                 170                 175
Gly Ser Ile Leu Ala Tyr Ala Phe Leu Gly Thr Ala Ile Ser Cys Phe
                180                 185                 190
Val Ile Gly Ser Ile Met Tyr Gly Cys Val Thr Leu Met Lys Val Thr
                195                 200                 205
Gly Gln Leu Ala Gly Asp Phe Tyr Phe Thr Asp Cys Leu Leu Phe Gly
    210                 215                 220
Ala Ile Val Ser Ala Thr Asp Pro Val Thr Val Leu Ala Ile Phe His
225                 230                 235                 240
Glu Leu Gln Val Asp Val Glu Leu Tyr Ala Leu Leu Phe Gly Glu Ser
                245                 250                 255
Val Leu Asn Asp Ala Val Ala Ile Val Leu Ser Ser Ser Ile Val Ala
                260                 265                 270
Tyr Gln Pro Ala Gly Asp Asn Ser His Thr Phe Asp Val Thr Ala Met
                275                 280                 285
Phe Lys Ser Ile Gly Ile Phe Leu Gly Ile Phe Ser Gly Ser Phe Ala
    290                 295                 300
Met Gly Ala Ala Thr Gly Val Val Thr Ala Leu Val Thr Lys Phe Thr
305                 310                 315                 320
Lys Leu Arg Glu Phe Gln Leu Leu Glu Thr Gly Leu Phe Phe Leu Met
                325                 330                 335
Ser Trp Ser Thr Phe Leu Leu Ala Glu Ala Trp Gly Phe Thr Gly Val
                340                 345                 350
Val Ala Val Leu Phe Cys Gly Ile Thr Gln Ala His Tyr Thr Tyr Asn
                355                 360                 365
Asn Leu Ser Thr Glu Ser Gln His Arg Thr Lys Gln Leu Phe Glu Leu
    370                 375                 380
Leu Asn Phe Leu Ala Glu Asn Phe Ile Phe Ser Tyr Met Gly Leu Thr
385                 390                 395                 400
Leu Phe Thr Phe Gln Asn His Val Phe Asn Pro Thr Phe Val Val Gly
                405                 410                 415
Ala Phe Val Ala Ile Phe Leu Gly Arg Ala Ala Asn Ile Tyr Pro Leu
                420                 425                 430
Ser Leu Leu Leu Asn Leu Gly Arg Arg Ser Lys Ile Gly Ser Asn Phe
                435                 440                 445
Gln His Met Met Met Phe Ala Gly Leu Arg Gly Ala Met Ala Phe Ala
    450                 455                 460
Leu Ala Ile Arg Asp Thr Ala Thr Tyr Ala Arg Gln Met Met Phe Ser
465                 470                 475                 480
Thr Thr Leu Leu Ile Val Phe Phe Thr Val Trp Val Phe Gly Gly Gly
                485                 490                 495
Thr Thr Ala Met Leu Ser Cys Leu His Ile Arg Val Gly Val Asp Ser
                500                 505                 510
Asp Gln Glu His Leu Gly Val Pro Glu Asn Glu Arg Arg Thr Thr Lys
                515                 520                 525
Ala Glu Ser Ala Trp Leu Phe Arg Met Trp Tyr Asn Phe Asp His Asn
    530                 535                 540
Tyr Leu Lys Pro Leu Leu Thr His Ser Gly Pro Pro Leu Thr Thr Thr
545                 550                 555                 560
```

-continued

```
Leu Pro Ala Cys Cys Gly Pro Ile Ala Arg Cys Leu Thr Ser Pro Gln
                565                 570                 575

Ala Tyr Glu Asn Gln Glu Gln Leu Lys Asp Asp Ser Asp Leu Ile
            580                 585                 590

Leu Asn Asp Gly Asp Ile Ser Leu Thr Tyr Gly Asp Ser Thr Val Asn
            595                 600                 605

Thr Glu Pro Ala Thr Ser Ser Ala Pro Arg Arg Phe Met Gly Asn Ser
            610                 615                 620

Ser Glu Asp Ala Leu Asp Arg Glu Leu Ala Phe Gly Asp His Glu Leu
625                 630                 635                 640

Val Ile Arg Gly Thr Arg Leu Val Leu Pro Met Asp Asp Ser Glu Pro
                645                 650                 655

Pro Leu Asn Leu Leu Asp Asn Thr Arg His Gly Pro Ala
                660                 665

<210> SEQ ID NO 31
<211> LENGTH: 541
<212> TYPE: PRT
<213> ORGANISM: C. elegans
<220> FEATURE:
<223> OTHER INFORMATION: Figure 2(a) CeNHE1 (GenBank Accession No.
      3877723)

<400> SEQUENCE: 31

Met Lys Val Glu Ser Leu Phe Phe Met Ser Gln Thr Phe Asp Val Ile
 1               5                  10                  15

Thr Lys Asn Lys Thr Ile Val Lys Glu Pro Pro Asp Tyr Leu Met Leu
                20                  25                  30

Glu Val Lys Pro Glu Gly Gly Ser Arg Val Ser Phe His Tyr Glu Leu
            35                  40                  45

Ile Glu Gly Phe Phe Ala Asp Lys Arg Lys Ile Glu Gln Gln Ile
     50                  55                  60

Glu Gln Lys Ser Val Phe Ser Pro Glu Val Phe Phe Asn Met Leu Ile
65                  70                  75                  80

Pro Pro Ile Ile Phe Asn Ala Gly Tyr Ser Leu Lys Lys Arg His Phe
                85                  90                  95

Phe Arg Asn Ile Gly Ser Ile Leu Ala Ile Val Phe Ile Gly Thr Thr
            100                 105                 110

Ile Ser Cys Phe Gly Thr Gly Cys Leu Met Phe Val Phe Thr Ser Ile
        115                 120                 125

Phe Gln Met Gly Tyr Ser Phe Lys Glu Leu Leu Phe Phe Gly Ala Leu
    130                 135                 140

Ile Ser Ala Thr Asp Pro Val Thr Ile Ile Ser Val Phe Asn Asp Met
145                 150                 155                 160

Asn Val Glu Ala Asp Leu Phe Ala Leu Ile Phe Gly Glu Ser Ala Leu
                165                 170                 175

Asn Asp Ala Val Ala Ile Val Leu Ser Glu Val Ile Glu Asn Phe Ser
            180                 185                 190

Thr Ser Ser Glu Ala Ile Thr Leu Gln Asp Phe Gly Ser Ala Ile Ala
        195                 200                 205

Gly Phe Ala Gly Val Phe Phe Gly Ser Leu Met Leu Gly Phe Met Ile
    210                 215                 220

Gly Cys Met Asn Ala Phe Leu Thr Lys Met Thr Leu Ile Ser Glu His
225                 230                 235                 240

Ala Leu Leu Glu Ser Ser Leu Phe Val Leu Ile Ser Tyr Ile Ser Phe
```

```
                    245                 250                 255
Leu Val Ala Glu Val Cys Gly Leu Thr Gly Ile Val Ser Val Leu Phe
            260                 265                 270

Cys Gly Ile Ala Gln Ala His Tyr Thr Tyr Asn Asn Leu Ser Asp Glu
        275                 280                 285

Ser Gln Ser Asn Thr Lys His Phe Phe His Met Val Ser Phe Ile Met
    290                 295                 300

Glu Ser Phe Ile Phe Cys Tyr Ile Gly Val Ser Val Phe Val Thr Asn
305                 310                 315                 320

Asn Gln Arg Trp Ser Phe Ser Phe Leu Leu Phe Ser Leu Ile Ser Ile
                325                 330                 335

Thr Ala Ser Arg Ala Leu Phe Val Tyr Pro Leu Ser Trp Leu Leu Asn
            340                 345                 350

Ile Arg Arg Arg Pro Lys Ile Pro Lys Arg Tyr Gln His Met Ile Leu
        355                 360                 365

Phe Ala Gly Leu Arg Gly Ala Met Ala Phe Ala Leu Ala Gly Arg Asn
    370                 375                 380

Thr Ser Thr Glu Asn Arg Gln Met Ile Phe Ala Thr Thr Thr Ala Val
385                 390                 395                 400

Val Ile Val Thr Val Leu Val Asn Gly Gly Leu Thr Ser Trp Met Ile
                405                 410                 415

Asp Tyr Leu Gln Ile Lys His Gly Lys Asp Ala Ile Glu Glu Gly Gln
            420                 425                 430

Arg Leu Glu Asn Ser Met Ser Ser Pro Ala Asp Gln His Ser Asp
        435                 440                 445

Leu Asp Glu Ser Val Pro Val Thr Met Ser Pro Gly Leu Asn Pro Trp
    450                 455                 460

Asp Lys Ala Phe Leu Pro Arg Lys Trp Tyr His Phe Asp Ala Arg Trp
465                 470                 475                 480

Gln Leu Leu Lys Leu Val Phe Gln Phe His Glu Thr Ser Thr Asp Pro
                485                 490                 495

Cys Asp Ala Ile Phe Gly Thr Asn Thr Pro Thr Val Leu Ser Ser Ile
            500                 505                 510

Asp Phe Leu Val Asp Phe Lys Pro Ser Thr Arg Val Arg Gln Cys Arg
        515                 520                 525

Ala Leu Gln Tyr Asn Cys Thr Ile Arg Asp Ser Ile Asp
    530                 535                 540

<210> SEQ ID NO 32
<211> LENGTH: 21
<212> TYPE: DNA
<213> ORGANISM: Synthetic
<220> FEATURE:
<223> OTHER INFORMATION: Page 54 -  PCR forward  primer (X6F)

<400> SEQUENCE: 32
cctcaggtga taccaatctc a                                            21

<210> SEQ ID NO 33
<211> LENGTH: 20
<212> TYPE: DNA
<213> ORGANISM: Synthetic
<220> FEATURE:
<223> OTHER INFORMATION: Page 54 -  PCR reverse primer (X6REV)

<400> SEQUENCE: 33
gatccaatgt aacaccggag                                              20
```

```
<210> SEQ ID NO 34
<211> LENGTH: 19
<212> TYPE: DNA
<213> ORGANISM: Synthetic
<220> FEATURE:
<223> OTHER INFORMATION: Page 54 -  PCR forward primer (NHX7F)

<400> SEQUENCE: 34
ttcgttctcg gccatgtcc                                                19

<210> SEQ ID NO 35
<211> LENGTH: 22
<212> TYPE: DNA
<213> ORGANISM: Synthetic
<220> FEATURE:
<223> OTHER INFORMATION: Page 54 - PCR reverse primer (NHX7REV)

<400> SEQUENCE: 35
cggagagacc aacaccttct gc                                            22

<210> SEQ ID NO 36
<211> LENGTH: 24
<212> TYPE: DNA
<213> ORGANISM: Synthetic
<220> FEATURE:
<223> OTHER INFORMATION: Page 37 - preferred oligonucleotide probe

<400> SEQUENCE: 36
ttcttcatat atcttttgcc accc                                          24

<210> SEQ ID NO 37
<211> LENGTH: 30
<212> TYPE: DNA
<213> ORGANISM: Synthetic
<220> FEATURE:
<223> OTHER INFORMATION: Page 55 - Primer

<400> SEQUENCE: 37
cgcgtcgaca tgttggattc tctagtgtcg                                    30
```